United States Patent
Butziger et al.

(10) Patent No.: US 11,229,781 B2
(45) Date of Patent: *Jan. 25, 2022

(54) MEDICAL ACCESS PORTS, TRANSFER DEVICES AND METHODS OF USE THEREOF

(71) Applicant: Versago Vascular Access, Inc., West Bridgewater, MA (US)

(72) Inventors: John M. Butziger, East Greenwich, RI (US); Steven J. Tallarida, Mansfield, MA (US); Ronald P. Murphy, Norton, MA (US)

(73) Assignee: VERSAGO VASCULAR ACCESS, INC., West Bridgewater, MA (US)

( * ) Notice: Subject to any disclaimer, the term of this patent is extended or adjusted under 35 U.S.C. 154(b) by 73 days.

This patent is subject to a terminal disclaimer.

(21) Appl. No.: 16/364,555

(22) Filed: Mar. 26, 2019

(65) Prior Publication Data

US 2019/0351209 A1  Nov. 21, 2019

Related U.S. Application Data

(63) Continuation of application No. 15/210,268, filed on Jul. 14, 2016, now Pat. No. 10,238,851.

(Continued)

(51) Int. Cl.
*A61M 39/02* (2006.01)
*A61M 5/158* (2006.01)
(Continued)

(52) U.S. Cl.
CPC ........ *A61M 39/0208* (2013.01); *A61M 39/02* (2013.01); *A61M 1/3653* (2013.01);
(Continued)

(58) Field of Classification Search
CPC .. A61M 39/02; A61M 39/0208; A61M 39/04; A61M 2039/0202; A61M 2039/0205; A61M 2205/04
See application file for complete search history.

(56) References Cited

U.S. PATENT DOCUMENTS

| 975,285 A | 11/1910 | Lymburner |
| 3,757,585 A | 9/1973 | Heller et al. |

(Continued)

FOREIGN PATENT DOCUMENTS

| AU | 2016294584 | 1/2018 |
| AU | 2015364382 | 7/2020 |

(Continued)

OTHER PUBLICATIONS

Notice of Allowance dated May 12, 2020, issued in U.S. Appl. No. 15/835,858, 9 pages.

(Continued)

*Primary Examiner* — Shefali D Patel
(74) *Attorney, Agent, or Firm* — Grossman, Tucker, Perreault & Pfleger, PLLC

(57) ABSTRACT

A medical system, comprising an implantable access port including an implantable access port body and at least one implantable access port needle; wherein the at least one needle is concealable inside the access port body in a concealed position and is exposable outside the access port body in an exposed position; wherein the at least one needle is arranged within the access port body to penetrate outwardly through skin of a subject from within the subject when the access port is implanted in the subject; a transfer device coupled to the at least one needle of the access port, the transfer device configured to transfer a fluid to and/or from the access port; and wherein the transfer device is configured to form a closed system with the access port, wherein the transfer device includes a fluid flow passage (Continued)

configured to transfer the fluid to and/or from the access port.

20 Claims, 26 Drawing Sheets

Related U.S. Application Data

(60) Provisional application No. 62/192,386, filed on Jul. 14, 2015.

(51) Int. Cl.
*A61M 1/36* (2006.01)
*A61M 5/142* (2006.01)
*A61M 5/14* (2006.01)

(52) U.S. Cl.
CPC ............ *A61M 1/3659* (2014.02); *A61M 5/14* (2013.01); *A61M 5/158* (2013.01); *A61M 2005/14284* (2013.01); *A61M 2005/1587* (2013.01); *A61M 2039/0202* (2013.01); *A61M 2039/0205* (2013.01); *A61M 2039/0241* (2013.01); *A61M 2205/04* (2013.01)

(56) References Cited

U.S. PATENT DOCUMENTS

| | | |
|---|---|---|
| 3,819,282 A | 6/1974 | Schultz |
| 4,096,896 A | 6/1978 | Engel |
| 4,181,132 A | 1/1980 | Parks |
| 4,190,040 A | 2/1980 | Schulte |
| 4,228,802 A | 10/1980 | Trott |
| 4,445,896 A | 5/1984 | Gianturco |
| 4,543,088 A | 9/1985 | Bootman et al. |
| 4,576,595 A | 3/1986 | Aas et al. |
| 4,673,394 A | 6/1987 | Fenton, Jr. et al. |
| 4,676,782 A | 6/1987 | Yamamoto et al. |
| 4,692,146 A | 9/1987 | Hilger |
| 4,710,167 A | 12/1987 | Lazorthes |
| 4,760,837 A | 8/1988 | Petit |
| 4,760,844 A | 8/1988 | Kyle |
| 4,781,680 A | 11/1988 | Redmond et al. |
| 4,802,885 A | 2/1989 | Weeks et al. |
| 4,840,615 A | 6/1989 | Hancock et al. |
| 4,892,518 A | 1/1990 | Cupp et al. |
| 4,904,241 A | 2/1990 | Bark |
| 4,919,653 A | 4/1990 | Martinez et al. |
| 4,929,236 A | 5/1990 | Sampson |
| 5,003,657 A | 4/1991 | Boiteau et al. |
| 5,006,115 A | 4/1991 | McDonald |
| 5,013,316 A | 5/1991 | Goble et al. |
| 5,041,098 A | 8/1991 | Loiterman et al. |
| 5,057,084 A | 10/1991 | Ensminger et al. |
| 5,084,015 A | 1/1992 | Moriuchi |
| 5,120,221 A | 6/1992 | Orenstein et al. |
| 5,137,529 A | 8/1992 | Watson et al. |
| 5,180,365 A | 1/1993 | Ensminger et al. |
| 5,203,771 A * | 4/1993 | Melker ................. A61M 39/04 600/577 |
| 5,213,574 A | 5/1993 | Fucker |
| 5,215,530 A | 6/1993 | Hogan |
| 5,217,462 A | 6/1993 | Asnis et al. |
| 5,234,406 A | 8/1993 | Drasner et al. |
| 5,281,199 A | 1/1994 | Ensminger et al. |
| 5,295,658 A | 3/1994 | Atkinson et al. |
| 5,306,255 A | 4/1994 | Haindl |
| 5,318,545 A | 6/1994 | Fucker |
| 5,332,398 A | 7/1994 | Miller et al. |
| 5,337,756 A | 8/1994 | Barbier et al. |
| 5,338,398 A | 8/1994 | Szwejkowski et al. |
| 5,350,360 A | 9/1994 | Ensminger et al. |
| 5,352,204 A | 10/1994 | Ensminger |
| 5,360,407 A | 11/1994 | Leonard |
| 5,387,192 A | 2/1995 | Glantz et al. |
| 5,391,801 A | 2/1995 | Sato et al. |
| 5,399,168 A | 3/1995 | Wadsworth, Jr. et al. |
| 5,417,656 A | 5/1995 | Ensminger et al. |
| 5,423,334 A | 6/1995 | Jordan |
| 5,476,460 A | 12/1995 | Montalvo |
| 5,498,265 A | 3/1996 | Asnis et al. |
| 5,520,643 A | 5/1996 | Ensminger et al. |
| 5,522,817 A | 6/1996 | Sander et al. |
| 5,527,278 A | 6/1996 | Ensminger et al. |
| 5,556,381 A | 9/1996 | Ensminger et al. |
| 5,558,641 A | 9/1996 | Glantz et al. |
| 5,562,617 A | 10/1996 | Finch, Jr. et al. |
| 5,562,618 A | 10/1996 | Cai et al. |
| 5,613,945 A | 3/1997 | Cai et al. |
| 5,637,088 A * | 6/1997 | Wenner ............ A61M 39/0208 604/93.01 |
| 5,643,267 A | 7/1997 | Hitomi et al. |
| 5,647,855 A | 7/1997 | Trooskin |
| 5,695,490 A | 12/1997 | Flaherty et al. |
| 5,702,413 A | 12/1997 | Lafontaine |
| 5,704,915 A | 1/1998 | Melsky et al. |
| 5,718,682 A | 2/1998 | Fucker |
| 5,718,692 A | 2/1998 | Schon et al. |
| 5,792,104 A | 8/1998 | Speckman et al. |
| 5,792,123 A | 8/1998 | Ensminger |
| 5,797,879 A | 8/1998 | DeCampli |
| 5,833,654 A | 11/1998 | Powers et al. |
| 5,836,935 A | 11/1998 | Ashton et al. |
| 5,843,069 A | 12/1998 | Butler et al. |
| 5,848,989 A | 12/1998 | Villani |
| 5,928,236 A | 7/1999 | Augagneur et al. |
| 5,931,801 A | 8/1999 | Burbank et al. |
| 5,951,512 A | 9/1999 | Dalton |
| 5,954,691 A | 9/1999 | Prosl |
| 5,989,206 A | 11/1999 | Prosl et al. |
| 6,007,516 A | 12/1999 | Burbank et al. |
| 6,030,397 A | 2/2000 | Monetti et al. |
| 6,039,712 A | 3/2000 | Fogarty et al. |
| 6,045,573 A | 4/2000 | Wenstrom, Jr. et al. |
| 6,048,343 A | 4/2000 | Mathis et al. |
| 6,056,751 A | 5/2000 | Fenton, Jr. |
| 6,113,572 A | 9/2000 | Gailey et al. |
| 6,139,565 A | 10/2000 | Stone et al. |
| 6,190,352 B1 | 2/2001 | Haarala et al. |
| 6,213,973 B1 | 4/2001 | Eliasen et al. |
| 6,413,260 B1 | 7/2002 | Berrevoets et al. |
| 6,478,783 B1 | 11/2002 | Moorehead |
| 6,527,754 B1 | 3/2003 | Tallarida et al. |
| 6,607,504 B2 | 8/2003 | Haarala et al. |
| 6,655,240 B1 | 12/2003 | DeVecchis et al. |
| 6,699,331 B1 | 3/2004 | Kritzler |
| 6,962,577 B2 | 11/2005 | Tallarida et al. |
| 6,981,977 B2 | 1/2006 | Herweck et al. |
| 7,056,316 B1 | 6/2006 | Burbank et al. |
| 7,131,962 B1 | 11/2006 | Estabrook et al. |
| 7,172,574 B2 | 2/2007 | Lundgren et al. |
| 7,272,997 B1 | 9/2007 | Lee et al. |
| 7,351,233 B2 | 4/2008 | Parks |
| 7,452,354 B2 | 11/2008 | Bright et al. |
| 7,618,462 B2 | 11/2009 | Ek |
| 7,713,251 B2 | 5/2010 | Tallarida et al. |
| 7,727,235 B2 | 6/2010 | Contiliano et al. |
| 7,803,143 B2 | 9/2010 | Tallarida et al. |
| 7,811,266 B2 | 10/2010 | Eliasen |
| 7,824,365 B2 | 11/2010 | Haarala et al. |
| 7,959,615 B2 | 6/2011 | Stats et al. |
| 8,182,453 B2 | 5/2012 | Eliasen |
| 8,377,034 B2 | 2/2013 | Tallarida et al. |
| 8,409,153 B2 | 4/2013 | Tallarida et al. |
| 8,529,525 B2 | 9/2013 | Gerber et al. |
| 8,641,676 B2 | 2/2014 | Butts et al. |
| 8,656,929 B2 | 2/2014 | Miller et al. |
| 8,721,620 B2 | 5/2014 | Imran |
| 9,060,809 B2 | 6/2015 | Tipirneni et al. |
| 9,295,773 B2 | 3/2016 | Prosl et al. |
| 9,480,831 B2 | 11/2016 | Tallarida et al. |
| 9,597,783 B2 | 3/2017 | Zhang |
| 9,764,124 B2 | 9/2017 | Tallarida et al. |

(56) References Cited

U.S. PATENT DOCUMENTS

| | | | |
|---|---|---|---|
| 10,238,851 B2 | 3/2019 | Butziger et al. | |
| 10,300,262 B2 | 5/2019 | Tallarida et al. | |
| 10,369,345 B2 | 8/2019 | Tallarida et al. | |
| 10,512,734 B2 | 12/2019 | Tallarida et al. | |
| 10,835,728 B2 | 11/2020 | Tallarida et al. | |
| 10,905,866 B2 | 2/2021 | Tallarida et al. | |
| 2001/0016713 A1* | 8/2001 | Takagi | A61M 25/0631 604/198 |
| 2001/0037094 A1 | 11/2001 | Adaniya et al. | |
| 2002/0095122 A1 | 7/2002 | Shaffer | |
| 2002/0198527 A1 | 12/2002 | Muckter | |
| 2003/0109837 A1 | 6/2003 | McBride-Sakal | |
| 2004/0092875 A1 | 5/2004 | Kochamba | |
| 2004/0097830 A1 | 5/2004 | Cooke et al. | |
| 2004/0097930 A1 | 5/2004 | Justis et al. | |
| 2004/0097941 A1 | 5/2004 | Weiner et al. | |
| 2004/0147929 A1 | 7/2004 | Biedermann et al. | |
| 2004/0158207 A1 | 8/2004 | Hunn et al. | |
| 2004/0181150 A1 | 9/2004 | Evans et al. | |
| 2005/0014993 A1 | 1/2005 | Mische | |
| 2005/0015048 A1 | 1/2005 | Chiu et al. | |
| 2005/0085778 A1 | 4/2005 | Parks | |
| 2005/0124980 A1 | 6/2005 | Sanders | |
| 2005/0143735 A1 | 6/2005 | Kyle | |
| 2005/0154373 A1 | 7/2005 | Deutsch | |
| 2005/0165431 A1 | 7/2005 | Krivoruchko | |
| 2005/0171493 A1 | 8/2005 | Nicholls | |
| 2005/0209619 A1 | 9/2005 | Johnson et al. | |
| 2005/0267421 A1 | 12/2005 | Wing | |
| 2006/0004325 A1 | 1/2006 | Hamatake et al. | |
| 2006/0142705 A1 | 6/2006 | Halili | |
| 2006/0178648 A1 | 8/2006 | Barron et al. | |
| 2006/0224129 A1 | 10/2006 | Beasley et al. | |
| 2006/0264988 A1 | 11/2006 | Boyle | |
| 2006/0276749 A1 | 12/2006 | Selmon et al. | |
| 2007/0078432 A1 | 4/2007 | Halseth et al. | |
| 2007/0100302 A1 | 5/2007 | Dicarlo et al. | |
| 2007/0233019 A1 | 10/2007 | Forsell | |
| 2007/0265595 A1 | 11/2007 | Miyamoto et al. | |
| 2008/0039820 A1 | 2/2008 | Sommers et al. | |
| 2008/0114308 A1 | 5/2008 | di Palma et al. | |
| 2008/0243106 A1 | 10/2008 | Coe et al. | |
| 2008/0262475 A1 | 10/2008 | Preinitz | |
| 2010/0249491 A1 | 9/2010 | Farnan et al. | |
| 2011/0137288 A1* | 6/2011 | Tallarida | A61M 39/0208 604/513 |
| 2011/0152901 A1 | 6/2011 | Woodruff et al. | |
| 2011/0160699 A1 | 6/2011 | Imran | |
| 2011/0264058 A1 | 10/2011 | Linden et al. | |
| 2011/0282285 A1 | 11/2011 | Blanchard et al. | |
| 2011/0295206 A1 | 12/2011 | Gurley | |
| 2011/0301652 A1 | 12/2011 | Reed et al. | |
| 2011/0311602 A1 | 12/2011 | Mills et al. | |
| 2012/0035585 A1 | 2/2012 | Kurrus et al. | |
| 2012/0053514 A1 | 3/2012 | Robinson et al. | |
| 2012/0136247 A1 | 5/2012 | Pillai | |
| 2012/0136366 A1 | 5/2012 | Pillai | |
| 2012/0209180 A1 | 8/2012 | Gray et al. | |
| 2012/0232501 A1 | 9/2012 | Eliasen | |
| 2013/0081728 A1 | 4/2013 | Alsaffar | |
| 2013/0116666 A1 | 5/2013 | Shih et al. | |
| 2013/0218103 A1 | 8/2013 | Tallarida et al. | |
| 2013/0226101 A1 | 8/2013 | Westcott | |
| 2013/0231637 A1 | 9/2013 | Tallarida et al. | |
| 2013/0274814 A1 | 10/2013 | Weiner et al. | |
| 2014/0102445 A1 | 4/2014 | Clement et al. | |
| 2014/0142418 A1 | 5/2014 | Gurley et al. | |
| 2014/0188179 A1 | 7/2014 | McCormick | |
| 2014/0257165 A1 | 9/2014 | Shechtman et al. | |
| 2014/0277191 A1 | 9/2014 | Evans et al. | |
| 2015/0051584 A1 | 2/2015 | Korkuch et al. | |
| 2015/0182727 A1 | 7/2015 | Gurley et al. | |
| 2015/0273201 A1 | 10/2015 | Tallarida et al. | |
| 2016/0175560 A1 | 6/2016 | Tallarida et al. | |
| 2016/0175575 A1 | 6/2016 | Tallarida et al. | |
| 2016/0263352 A1 | 9/2016 | Gurley | |
| 2017/0000995 A1 | 1/2017 | Tallarida et al. | |
| 2017/0014611 A1 | 1/2017 | Butziger et al. | |
| 2017/0173273 A1 | 6/2017 | Tallarida et al. | |
| 2017/0246427 A1 | 8/2017 | Gurley | |
| 2017/0340814 A1 | 11/2017 | Miesel et al. | |
| 2018/0104465 A1 | 4/2018 | Tallarida et al. | |
| 2019/0192769 A1 | 6/2019 | Tallarida et al. | |
| 2019/0209808 A1 | 7/2019 | Gurley et al. | |
| 2020/0238021 A1 | 7/2020 | Tallarida et al. | |

FOREIGN PATENT DOCUMENTS

| | | | |
|---|---|---|---|
| AU | 2015364276 | 8/2020 | |
| EP | 1680174 | 7/2006 | |
| EP | 2403431 | 1/2012 | |
| EP | 3233175 | 5/2018 | |
| EP | 3322460 | 5/2018 | |
| EP | 3125970 | 5/2020 | |
| GB | 2502291 | 11/2013 | |
| JP | 55-065009 | 5/1980 | |
| JP | 5506591 | 9/1993 | |
| JP | 8500031 | 1/1996 | |
| JP | 9-509852 | 10/1997 | |
| JP | 2002119462 | 4/2002 | |
| JP | 2002523131 | 7/2002 | |
| JP | 2004167005 | 6/2004 | |
| JP | 2004535234 | 11/2004 | |
| JP | 2005522280 | 7/2005 | |
| JP | 2008100084 | 5/2008 | |
| JP | 2009-273598 | 11/2009 | |
| JP | 2011120737 | 6/2011 | |
| JP | 6837971 | 2/2021 | |
| WO | 9701370 | 1/1997 | |
| WO | 00/78231 | 12/2000 | |
| WO | 0078231 | 12/2000 | |
| WO | 2005025665 | 3/2005 | |
| WO | 2005/094702 | 10/2005 | |
| WO | 2007051563 | 5/2007 | |
| WO | 2008126966 | 10/2008 | |
| WO | WO-2008126966 A1 * | 10/2008 | ........ A61M 39/0208 |
| WO | 2009/148587 | 12/2009 | |
| WO | 2011035387 | 3/2011 | |
| WO | 2015153611 | 10/2015 | |
| WO | 2015153976 | 10/2015 | |
| WO | 2016/100868 | 6/2016 | |
| WO | 2016/100945 | 6/2016 | |
| WO | 2019126306 | 6/2019 | |

OTHER PUBLICATIONS

Examination Report dated May 20, 2020, issued in European Patent Application No. 15 772 648.0, 4 pages.

Office Action dated Jun. 2, 2020, issued in Japanese Patent Application No. 2017-532627, 6 pages.

Office Action dated Jun. 18, 2020, issued in Japanese Patent Application No. 2017-565905, 11 pages.

PCT International Search Report dated Nov. 21, 2001 issued in PCT Application No. PCT/US01/13749, 4 pages.

PCT Written Opinion dated Dec. 19, 2002 issued in PCT Application PCT/US01/13749, 5 pages.

PCT Preliminary Examination Report dated May 28, 2003 issued in PCT Application PCT/US01/13749, 2 pages.

European Examination Report dated Jul. 30, 2003 issued in European Patent Application No. 99 964 086.5, 5 pages.

U.S. Office Action dated Aug. 27, 2003 issued in U.S. Appl. No. 09/842,458, 8 pages.

U.S. Office Action dated Dec. 23, 2003 issued in U.S. Appl. No. 09/842,458, 7 pages.

European Examination Report dated Mar. 9, 2004 issued in European Patent Application No. 99 964 086.5, 4 pages.

U.S. Notice of Allowance dated Oct. 15, 2004 issued in U.S. Appl. No. 09/842,458, 7 pages.

Australian Examination Report dated Jan. 21, 2005 issued in Australian Patent Application No. 2001257388, 2 pages.

(56) References Cited

OTHER PUBLICATIONS

U.S. Notice of Allowance dated Feb. 24, 2005 issued in U.S. Appl. No. 09/842,458, 6 pages.
European Examination Report dated Mar. 1, 2005 issued in European Patent Application No. 99 964 086.5, 4 pages.
European Examination Report dated Mar. 30, 2005 issued in European Patent Application No. 99 964 086.5, 3 pages.
European Decision to Refuse dated Dec. 15, 2005 issued in European Patent Application No. 99 964 086.5, 9 pages.
U.S. Office Action dated Feb. 14, 2007 issued in U.S. Appl. No. 10/890,909, 12 pages.
U.S. Office Action dated Apr. 11, 2007 issued in U.S. Appl. No. 10/931,890, 7 pages.
U.S. Office Action dated Sep. 13, 2007 issued in U.S. Appl. No. 10/890,909, 11 pages.
U.S. Office Action dated Sep. 13, 2007 issued in U.S. Appl. No. 10/931,890, 7 pages.
Canadian Office Action dated Oct. 16, 2007 issued in Canadian Patent Application No. 2,407,643, 2 pages.
U.S. Office Action dated Feb. 21, 2008 issued in U.S. Appl. No. 11/269,098, 19 pages.
U.S. Office Action dated Jun. 9, 2008 issued in U.S. Appl. No. 10/931,890, 10 pages.
U.S. Office Action dated Oct. 30, 2008 issued in U.S. Appl. No. 11/269,098, 12 pages.
U.S. Office Action dated Dec. 23, 2008 issued in U.S. Appl. No. 10/931,890, 9 pages.
U.S. Office Action dated Jun. 4, 2009 issued in U.S. Appl. No. 11/269,098, 11 pages.
Supplemental European Search Report dated Jun. 10, 2009 issued in European Patent Application No. 01 930 898.0, 4 pages.
U.S. Office Action dated Aug. 3, 2009 issued in U.S. Appl. No. 10/931,890, 10 pages.
European Examination Report dated Oct. 2, 2009 issued in European Patent Application No. 01 930 898.0, 4 pages.
U.S. Office Action dated Mar. 3, 2010 issued in U.S. Appl. No. 11/269,098, 15 pages.
U.S. Office Action dated Feb. 17, 2011 issued in U.S. Appl. No. 12/902,839, 17 pages.
U.S. Office Action dated Oct. 17, 2011 issued in U.S. Appl. No. 12/902,839, 11 pages.
Notice of Allowance dated Feb. 1, 2012 issued in U.S. Appl. No. 12/902,839, 7 pages.
European Office Action dated Oct. 23, 2012 issued in European Patent Application No. 01 930 898.0, 4 pages.
U.S. Office Action dated Feb. 28, 2007 issued in U.S. Appl. No. 10/374,000, 8 pages.
U.S. Office Action dated Aug. 28, 2007 issued in U.S. Appl. No. 10/374,000, 8 pages.
U.S. Office Action dated Mar. 20, 2008 issued in U.S. Appl. No. 10/374,000, 7 pages.
U.S. Office Action dated Sep. 30, 2008 issued in U.S. Appl. No. 10/374,000, 8 pages.
U.S. Office Action dated May 20, 2009 issued in U.S. Appl. No. 10/374,000, 10 pages.
Access technologies, The V-A-Pu . . . Vascular Access and Beyond, downloaded from internet Jul. 28, 2009, http://www.norfolkaccess.com/VAPs.html, 4 pages.
SyncMedical, Innovative Surgical Devices, Primo Port Products, downloaded from internet Jul. 28, 2009, http://www.syncmedical.com/primo-port, 2 pages.
Corrected Notice of Allowability dated Jul. 12, 2016, issued in U.S. Appl. No. 13/770,732, 6 pages.
Corrected Notice of Allowability dated Aug. 2, 2016, issued in U.S. Appl. No. 13/770,732, 6 pages.
International Search Report and Written Opinion dated Oct. 7, 2016, issued in PCT International Patent Application No. PCT/US2016/042272, 11 pages.
International Preliminary Report on Patentability dated Oct. 13, 2016, issued in PCT International Patent Application No. PCT/US2015/023590, 9 pages.
International Preliminary Report on Patentability dated Oct. 13, 2016, issued in PCT International Patent Application No. PCT/US2015/024256, 8 pages.
U.S. Office Action dated Oct. 23, 2014 issued in U.S. Appl. No. 13/477,997, 14 pages.
U.S. Office Action dated Dec. 2, 2014, issued in U.S. Appl. No. 13/770,732, 15 pages.
U.S. Office Action dated Jun. 10, 2015, issued in U.S. Appl. No. 13/770,732, 14 pages.
International Search Report and Written Opinion dated Jul. 2, 2015, issued in PCT Patent Application No. PCT/US2015/023590, 11 pages.
International Search Report and Written Opinion dated Jul. 10, 2015, issued in PCT Patent Application No. PCT/US2015/024256, 10 pages.
U.S. Office Action dated Aug. 10, 2015, issued in U.S. Appl. No. 14/231,392, 24 pages.
U.S. Office Action dated Jan. 15, 2016, issued in U.S. Appl. No. 13/770,732, 23 pages.
Decision to Grant dated Feb. 4, 2020, issued in Japanese Patent Application No. 2017-532615, 4 pages. English language summary provided.
Examination Report dated Mar. 23, 2020, issued in Australian Patent Application No. 2016294584, 6 pages.
Office Action dated Mar. 27, 2020, issued in U.S. Appl. No. 14/974,851, 12 pages.
Office Action dated Mar. 27, 2020, issued in U.S. Appl. No. 14/975,638, 12 pages.
Notice of Acceptance dated Apr. 20, 2020, issued in Australian Patent Application No. 2015364276, 4 pages.
International Search Report and Written Opinion dated Feb. 26, 2016, issued in PCT Patent Application Serial No. PCT/US2015/066934, 11 pages.
International Search Report and Written Opinion dated Mar. 7, 2016, issued in PCT Patent Application Serial No. PCT/US2015/066778, 9 pages.
Final Office Action dated Mar. 22, 2016, issued in U.S. Appl. No. 14/231,392, 22 pages.
Notice of Allowance dated Jun. 15, 2016, issued in U.S. Appl. No. 13/770,732, 9 pages.
U.S. Office Action dated Nov. 30, 2016, issued in U.S. Appl. No. 14/231,392, 6 pages.
Office Action dated Aug. 31, 2017, issued in U.S. Appl. No. 14/974,851, 12 pages.
Search Report dated Nov. 8, 2017, issued in European Patent Application No. 15773029.2, 8 pages.
European Extended Search Report dated Nov. 27, 2017, issued in European Patent Application No. 15772648.0, 7 pages.
Office Action dated Nov. 30, 2017, issued in U.S. Appl. No. 15/210,268, 15 pages.
Preliminary Report on Patentability dated Jan. 25, 2018, issued in PCT Patent Application No. PCT/US2016/042272, 9 pages.
Office Action dated Feb. 26, 2018, issued in U.S. Appl. No. 14/974,851, 12 pages.
Office Action dated Mar. 27, 2018, issued in U.S. Appl. No. 14/975,638, 8 pages.
Office Action dated Jun. 27, 2018, issued in U.S. Appl. No. 15/300,625, 14 pages.
Extended Search Report dated Jul. 4, 2018, issued in European Patent Application No. 15871254.7, 5 pages.
Partial Supplementary Search Report dated Aug. 2, 2018, issued in European Patent Application No. 15871198.6, 13 pages.
Office Action dated Aug. 29, 2018, issued in U.S. Appl. No. 15/267,537, 8 pages.
Notice of Allowance dated Sep. 12, 2018, issued in U.S. Appl. No. 15/210,268, 12 pages.
Intent to Grant dated Oct. 4, 2018, issued in European Patent Application No. 15871254.7, 7 pages.
Office Action dated Oct. 17, 2018, issued in U.S. Appl. No. 15/301,498, 14 pages.

(56) References Cited

OTHER PUBLICATIONS

Notice of Allowance dated Oct. 30, 2018, issued in U.S. Appl. No. 15/210,268, 11 pages.
Office Action dated Nov. 30, 2018, issued in European Patent Application No. 15 772 648.0, 4 pages.
Office Action dated Dec. 10, 2018, issued in U.S. Appl. No. 14/975,638, 16 pages.
Office Action dated Dec. 25, 2018, issued in Japanese Patent Application No. 2017-503790, 12 pages. English language machine translation provided.
Office Action dated Jan. 7, 2019, issued in U.S. Appl. No. 14/974,851, 12 pages.
Examination Report dated Jan. 10, 2019, issued in Australian Patent Application No. 2015240953, 5 pages.
Notice of Allowance dated Jan. 10, 2019, issued in U.S. Appl. No. 15/267,537, 8 pages.
Extended Search Report dated Dec. 12, 2018, issued in European Patent Application No. 15871198.6, 15 pages.
Examination Report dated Jan. 16, 2019, issued in Australian Patent Application No. 2015240568, 5 pages.
Decision to Grant dated Feb. 5, 2019, issued in Japanese Patent Application No. 2017-503777, 4 pages.
Office Action dated Feb. 6, 2019, issued in U.S. Appl. No. 15/301,498, 10 pages.
Extended Search Report dated Mar. 1, 2019, issued in European Patent Application No. 16825172.6, 7 pages.
Notice of Allowance dated Mar. 18, 2019, issued in U.S. Appl. No. 15/300,625, 8 pages.
International Search Report and Written Opinion dated Mar. 21, 2019, issued in PCT International Patent Application No. PCT/US2018/066472, 9 pages.
Office Action dated Jun. 13, 2019, issued in U.S. Appl. No. 14/974,851, 11 pages.
Notice of Allowance dated Jul. 3, 2019, issued in Australian Patent Application No. 2015240953, 4 pages.
Notice of Allowance dated Aug. 8, 2019, issued in Australian Patent Application No. 2015240568, 4 pages.
Examination Report dated Aug. 14, 2019, issued in Australian Patent Application No. 2015364276, 4 pages.
Examination Report dated Aug. 21, 2019, issued in Australian Patent Application No. 2015364382, 5 pages.
Notice of Allowance dated Aug. 27, 2019, issued in U.S. Appl. No. 15/301,498, 10 pages.
Office Action dated Sep. 18, 2019, issued in U.S. Appl. No. 14/975,638, 15 pages.
Office Action dated Oct. 1, 2019, issued in Japanese Patent Application No. 2017-532627, 9 pages.
Office Action dated Oct. 1, 2019, issued in Japanese Patent Application No. 2017-532615, 5 pages.
Office Action dated Nov. 26, 2019, issued in U.S. Appl. No. 15/835,858, 15 pages.
Intent to Grant dated Dec. 10, 2019, issued in European Patent Application No. 15 773 029.2, 6 pages.
Notice of Allowance dated Mar. 17, 2021, issued in U.S. Appl. No. 16/225,598, 8 pages.
Notice of Allowance dated Oct. 1, 2020, issued in U.S. Appl. No. 14/975,638, 12 pages.
Office Action dated Nov. 3, 2020, issued in U.S. Appl. No. 14/974,851, 13 pages.
Office Action dated Apr. 16, 2021, issued in Canadian Patent Application No. 2,944,434, 5 pages.
Decision to Grant dated Apr. 1, 2021, issued in Japanese Patent Application No. 2017-565905, 6 pages.
Intent to Grant dated Apr. 12, 2021, issued in European Patent Application No. 15772648.0, 7 pages.

* cited by examiner

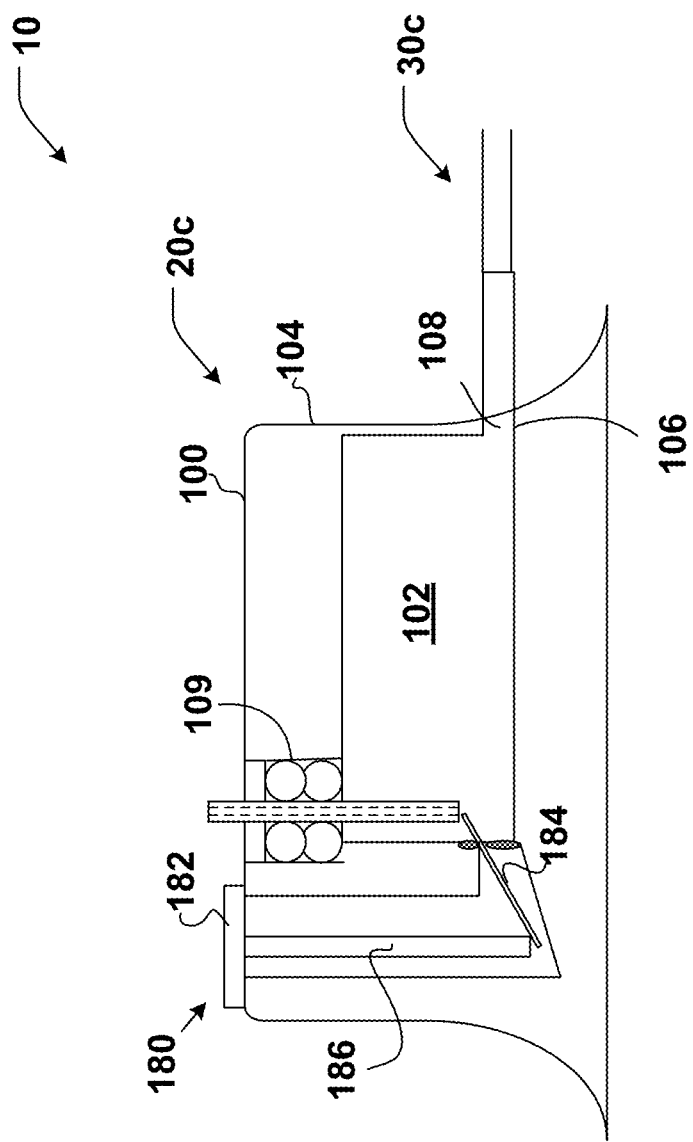

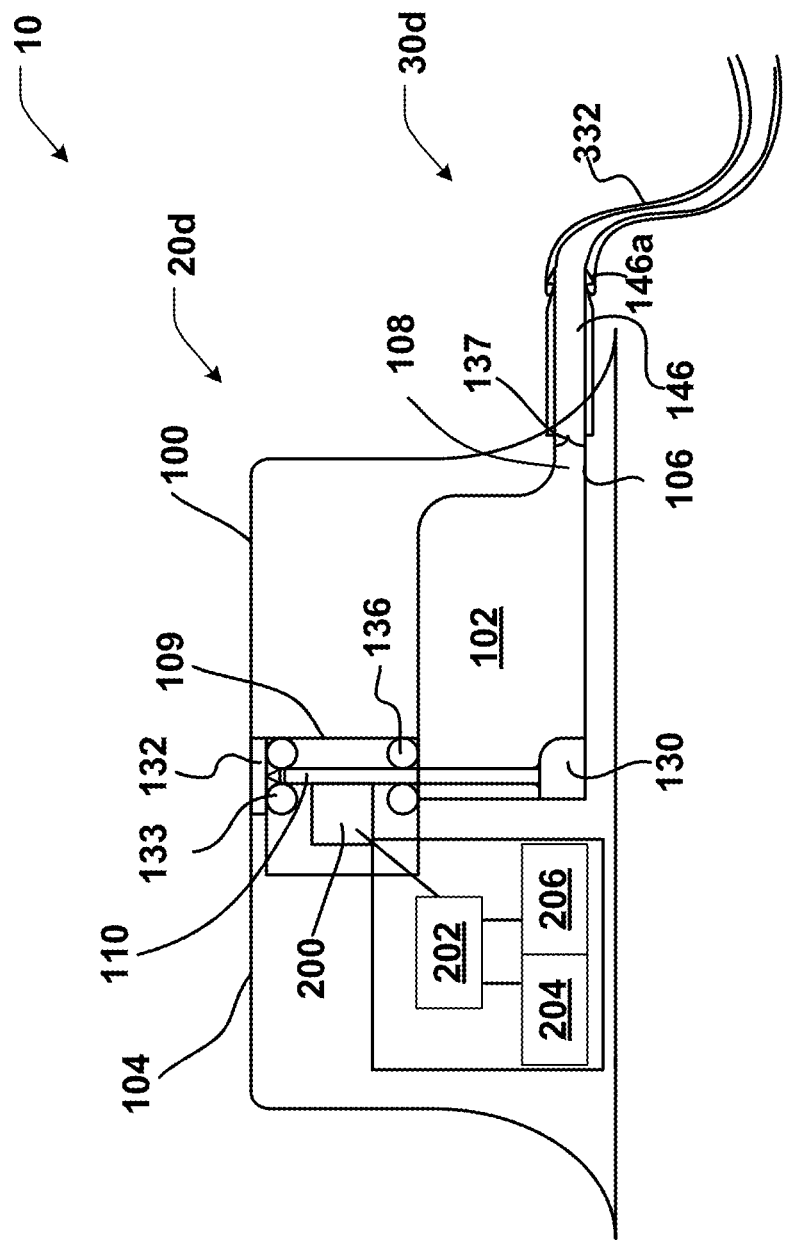

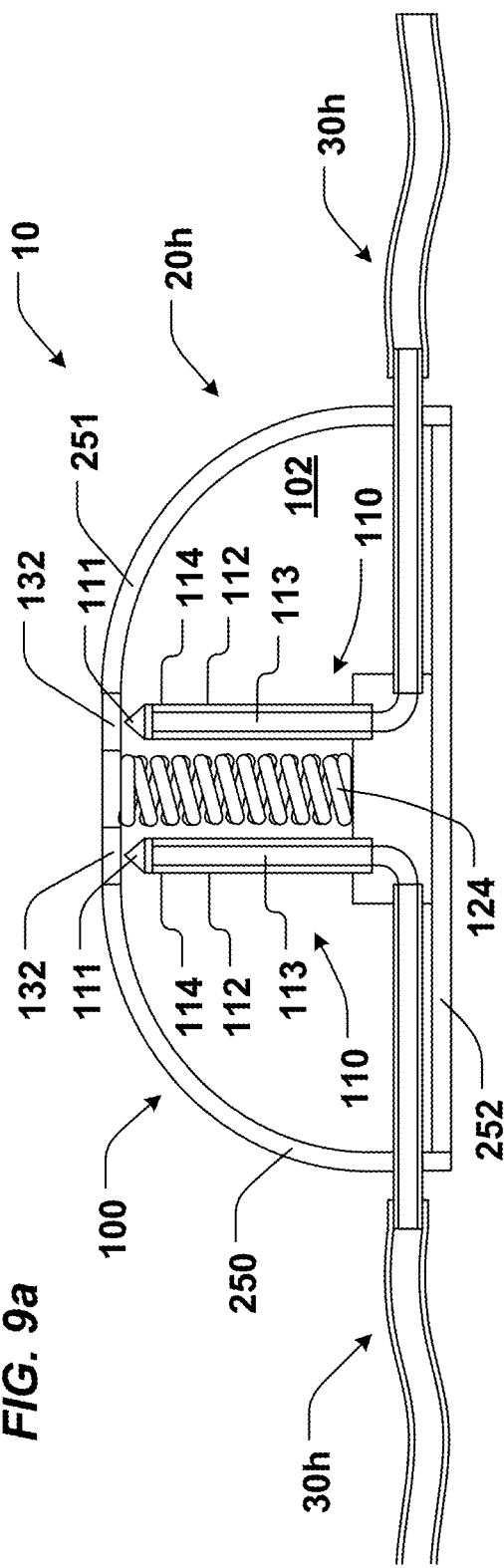
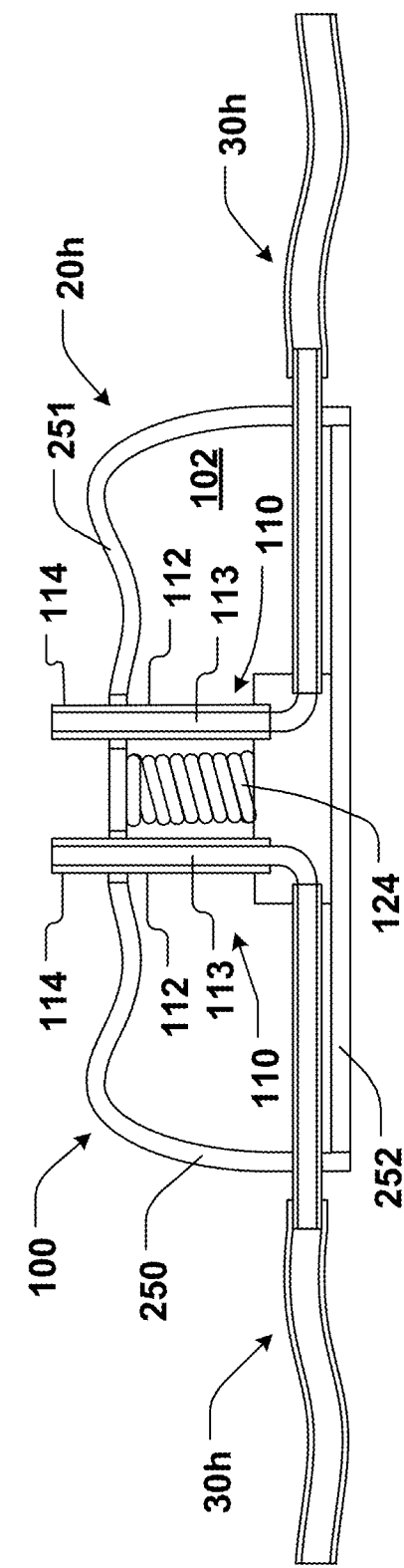

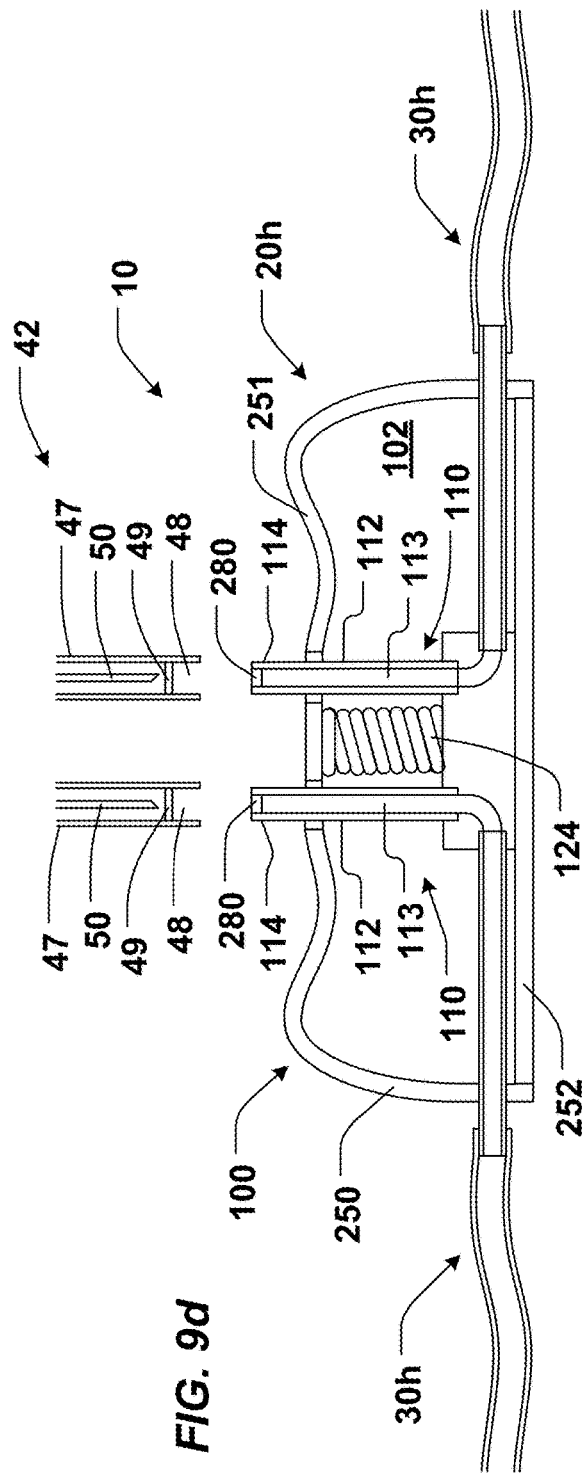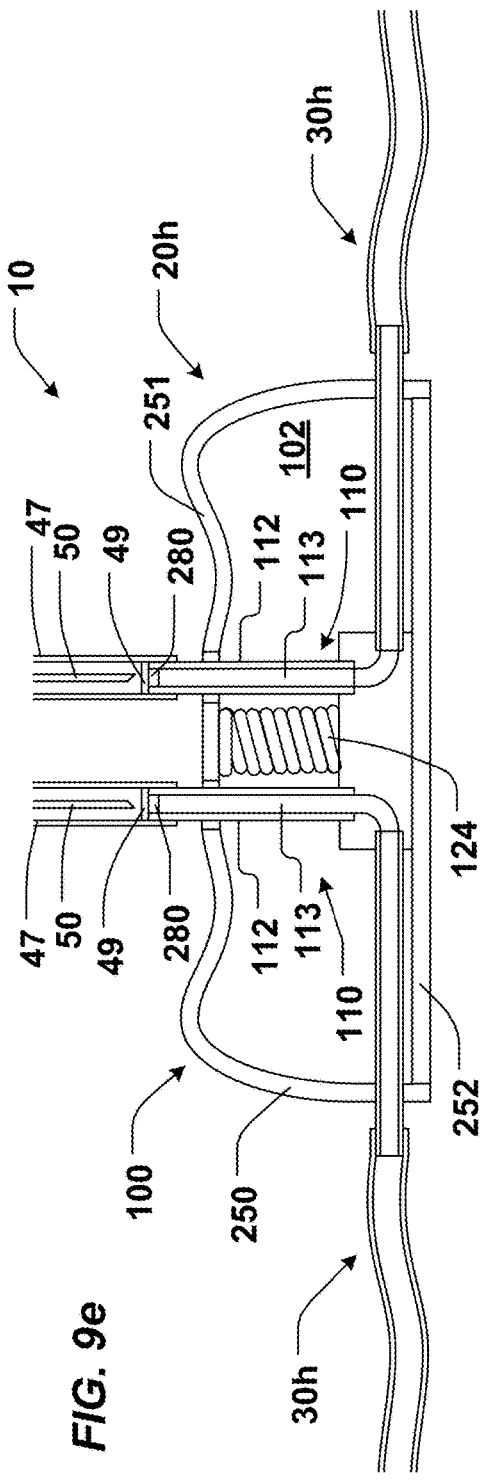

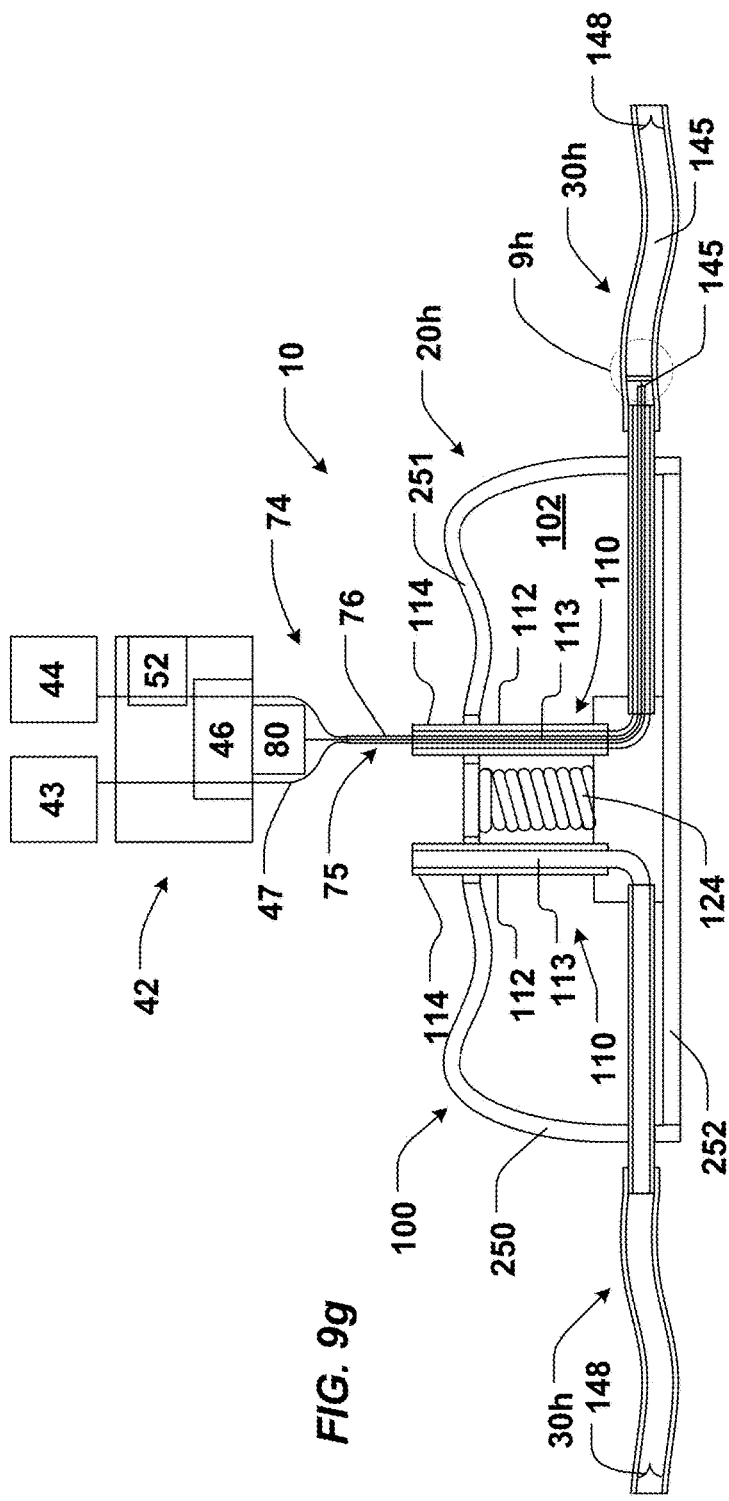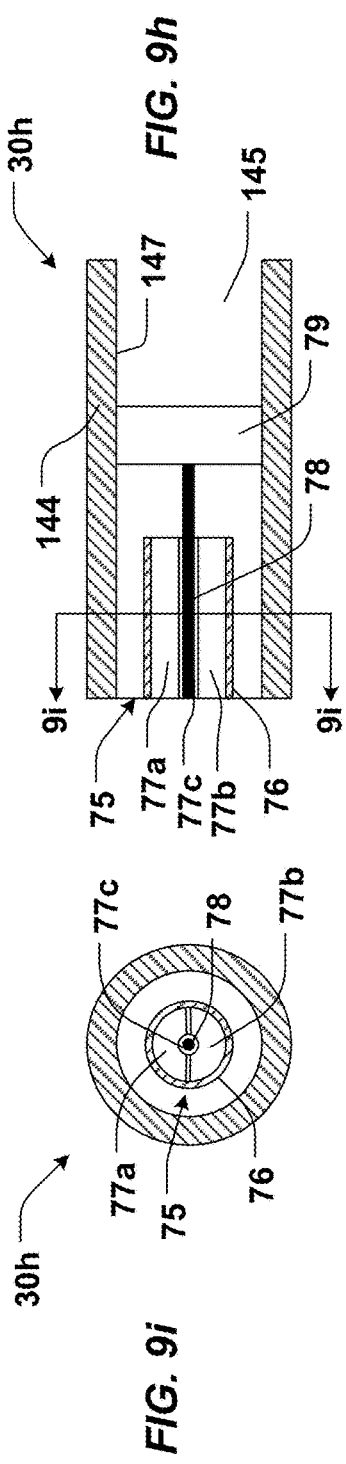

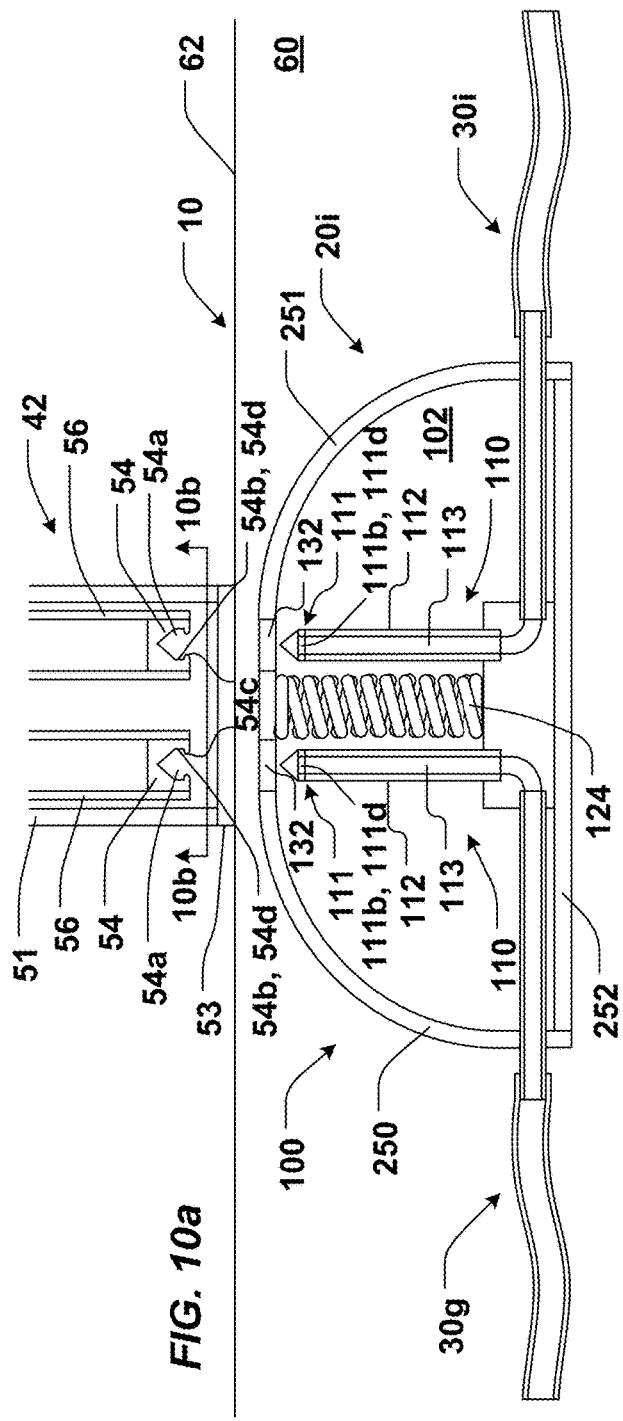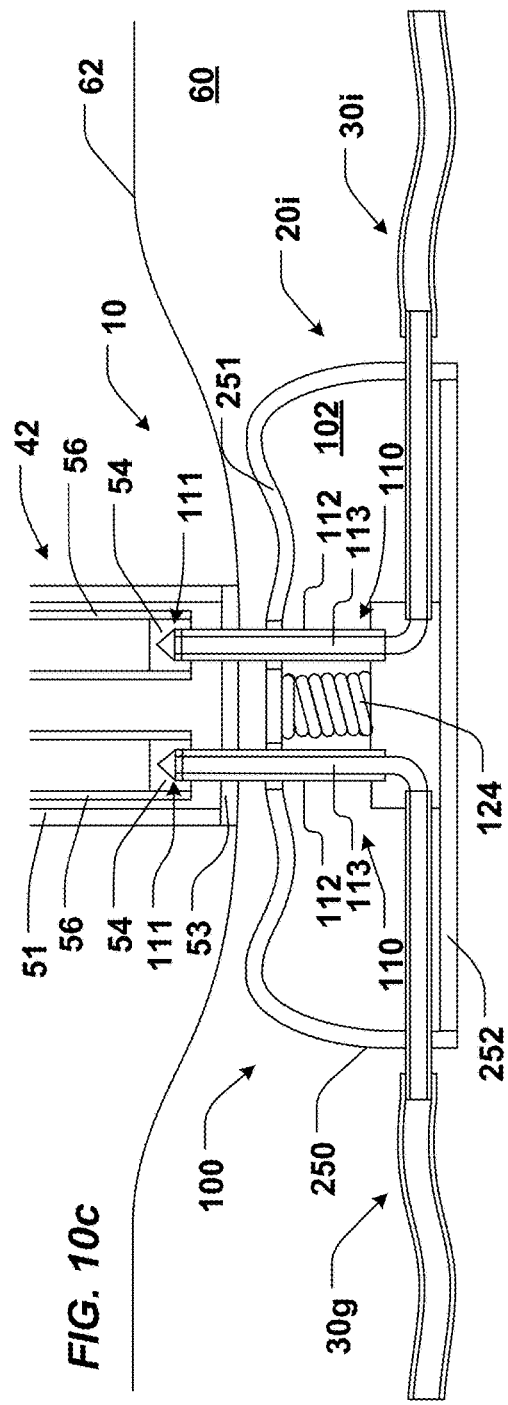

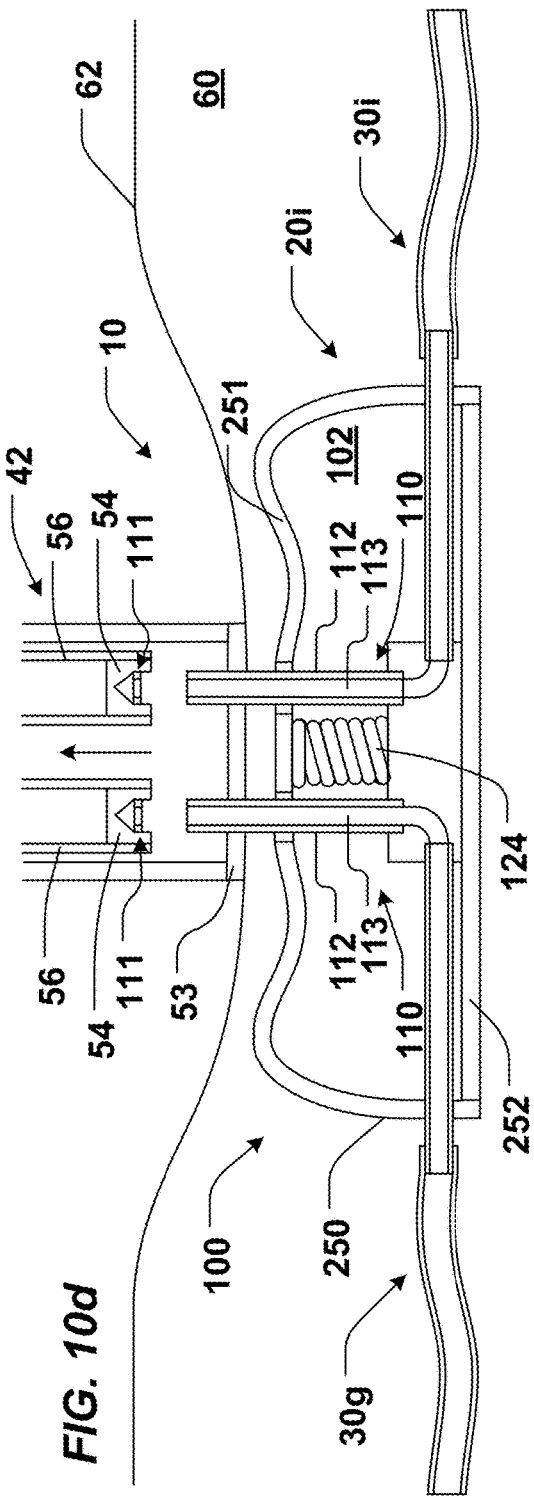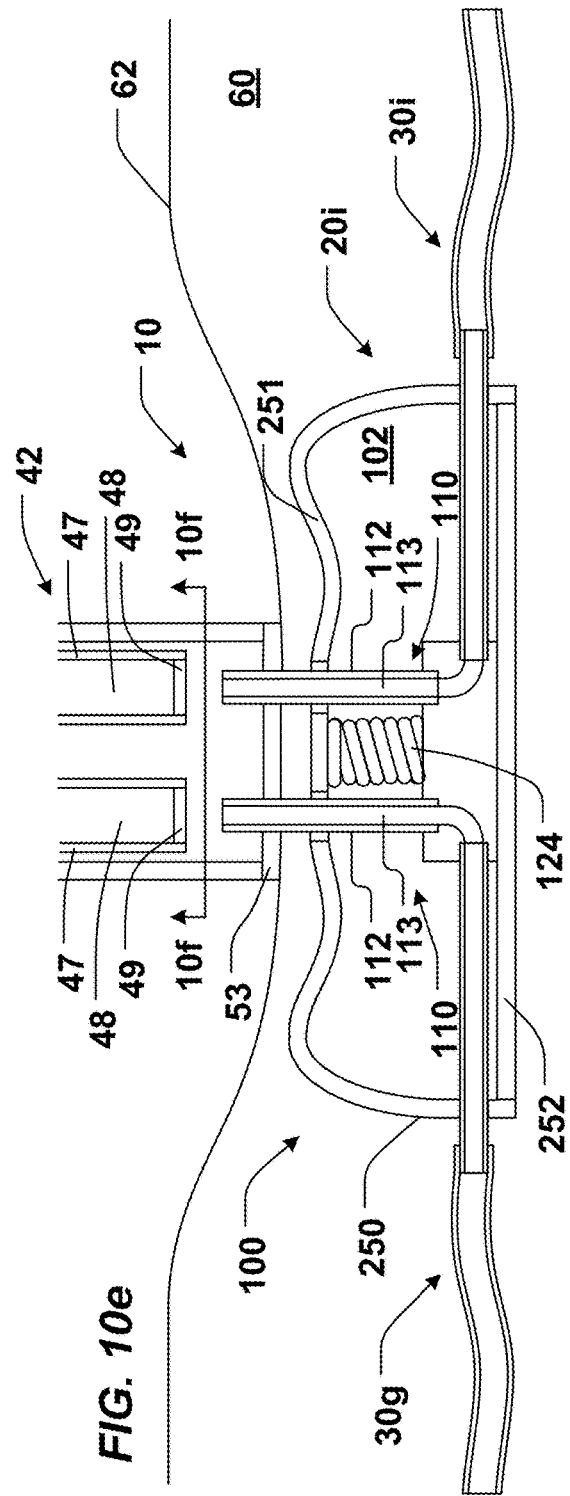

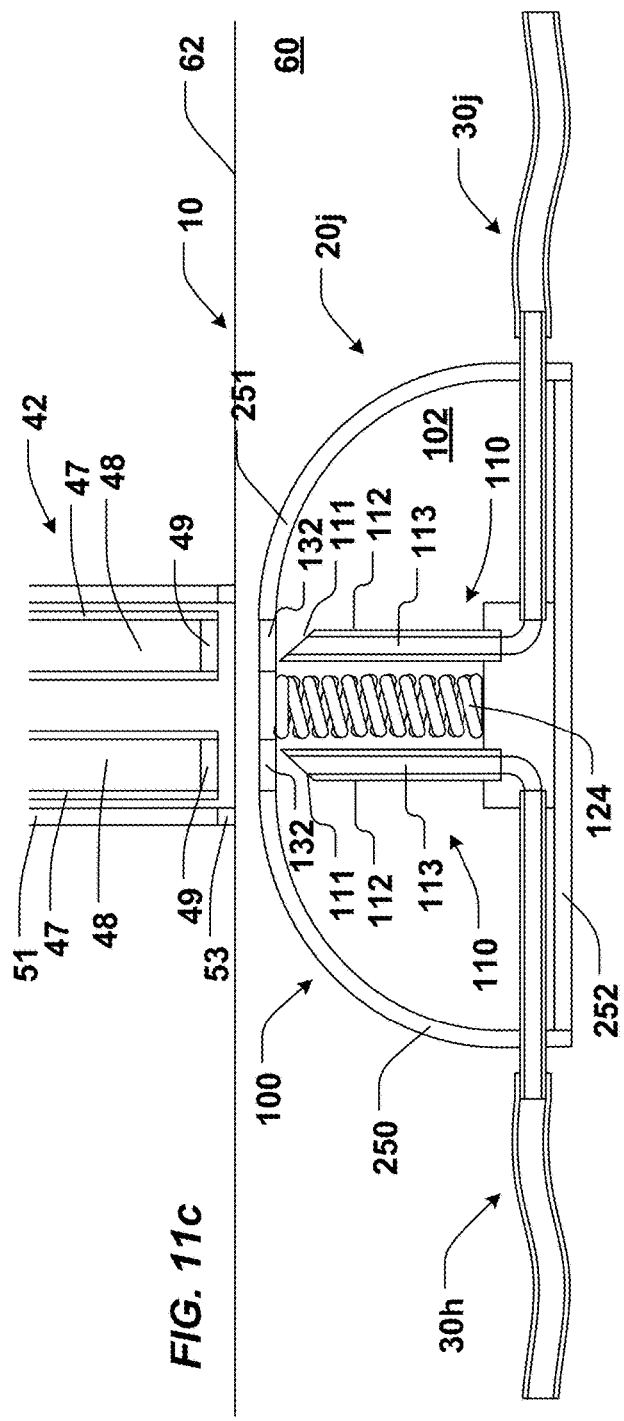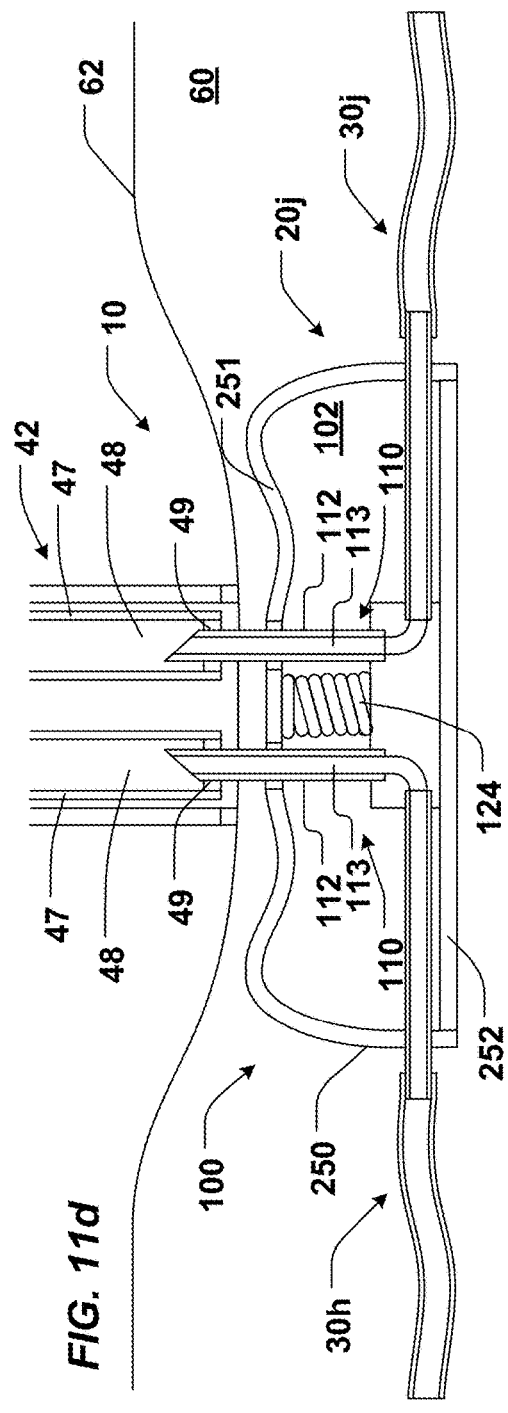

MEDICAL ACCESS PORTS, TRANSFER DEVICES AND METHODS OF USE THEREOF

CROSS-REFERENCE TO RELATED APPLICATIONS

This application is a continuation of U.S. patent application Ser. No. 15/210,268, (now U.S. Pat. No. 10,238,851) filed Jul. 14, 2016, which claims the benefit of U.S. provisional application No. 62/192,386 filed Jul. 14, 2015.

FIELD

The present disclosure relates generally to medical devices, systems and methods, and more particularly to indwelling access devices, systems and methods which may comprise an implantable (subcutaneous) indwelling access port, which may be coupled with at least one implantable (subcutaneous) indwelling catheter within a body, particularly a human body.

BACKGROUND

Medical patients, such as oncology patients, hemodialysis patients and hematology patients, may be subject to frequent fluid infusion treatments and/or fluid extraction treatments. Fluid infusion treatments may deliver medication (e.g. pharmaceutical products; therapeutic drugs), bodily fluid (e.g. blood), nutrients, contrasting agents, dialysis fluid and other liquid compositions to the body, while fluid extraction treatments may remove fluids such as dialysis fluid, bodily fluid (e.g. blood as part of phlebotomy) and other liquid compositions from the body. A fluid infusion treatment and fluid extraction treatment may be part of a fluid exchange treatment, such as dialysis.

Many fluid treatments involve the use of an indwelling catheter with transgresses out of the body. However, where the catheter passes through the body, there may be an increased risk of infection inception which can spread both internally and externally.

In order to reduce the likelihood of infection associated with the foregoing transcutaneous catheter, certain medical applications may be able to utilize an access port implanted beneath the cutaneous tissue (skin) of the patient/body.

An implanted access port may include an access point, such as a septum, into which an external hypodermic needle may be inserted. The access port is coupled to an indwelling catheter, which is inserted into a vein, such as a jugular vein, subclavian vein or superior vena cava. The septum may be formed of a self-healing silicone material, which may be punctured multiple times with a small gauge needle (e.g. 20-21 gauge) with a relatively low loss in its integrity.

External access to the implanted vascular access port may be accomplished by inserting the hypodermic needle through the patient's skin and through the septum of the implanted port. However, a clinician needs to properly target the access port and, as a result, multiple needle sticks may be required to properly locate and access the access port, which may add discomfort to the patient.

Additionally, for certain medical applications, a large gauge needle (e.g. 14-17 gauge) may be required to facilitate suitable flow rates for fluids. However, large gauge hypodermic needles may damage the septum of the implanted port, which may result in the septum leaking, as well as also add discomfort to the patient. Moreover, the external hypodermic needle may introduce bacteria into the entrance site, which may increase the risk of infection.

SUMMARY

By way of general overview, the present disclosure provides medical devices, systems and methods, and more particularly provides indwelling access devices, systems and methods which may comprise an implantable, subcutaneous, indwelling access port, which may be coupled with one or more implantable, subcutaneous, indwelling catheters within a body, particularly a human body, as well as a transfer device.

The access port may include an access port body containing at least one exposable/concealable (e.g. extendable/retractable) internal needle that may extend/retract relative to the access port body to expose/conceal the internal needle. The access port may also include an access port body containing at least one exposable/concealable internal needle and having an access port body that is configured to compress (collapse) to expose the internal needle and configured to decompress (expand) to expose the internal needle.

The internal needle includes a lumen which provides a segment of a fluid passage which extends through the needle, the access port body and an adjoining catheter which is completely implanted in the host. The fluid passage may be used to delivery fluid to the host, particularly with a fluid infusion treatment, and/or extract fluid from the host, particularly with a fluid extraction treatment.

The internal needle may be concealable in, and exposable from, the access port body by a variety of mechanisms, which may include mechanical, magnetic, electrical and electro-mechanical mechanisms as disclosed herein.

The access ports herein may be used to provide peritoneal dialysis and/or hemodialysis as part of treatment for kidney disease/failure; to remove fluid from the peritoneal cavity to treat ascites; to provide nutrition to s host as part of total parenteral nutrition to treat eating and digestion disorders; to deliver cells to the host to treat cancer; to remove blood from the host to treat hemochromatosis; to deliver blood to the host to treat sickle cell disease and beta thalassemia as a few particular medical applications.

In at least one embodiment, a medical system may be provided, comprising an implantable access port configured to be implanted into a subject, the access port including an implantable access port body and at least one implantable access port needle; wherein the at least one needle is concealable inside the access port body in a concealed position and is exposable outside the access port body in an exposed position; wherein the at least one needle is arranged within the access port body to penetrate outwardly through skin of the subject from within the subject when the access port is implanted in the subject; a transfer device coupled to the at least one needle of the access port, the transfer device configured to transfer a fluid to and/or from the access port; and wherein the transfer device is configured to form a closed treatment system with the access port, wherein the transfer device includes a fluid flow passage configured to transfer the fluid to and/or from the access port.

In at least one embodiment, the transfer device may be configured to inhibit transfer of environmental contaminants into the treatment system and escape of hazardous material outside the treatment system.

In at least one embodiment, the at least one needle may include a removable needle tip, and the transfer device may include a needle tip holder configured to hold the needle tip.

In at least one embodiment, the needle tip holder may be configured to form an interference fit with the needle tip and/or configured to form a positive mechanical engagement with the needle tip.

In at least one embodiment, the at least one needle may include a needle shaft and a needle tip which is removable from the needle shaft, and the transfer device may be configured to remove the needle tip from the needle shaft, particularly by rotating the needle tip or applying a pulling force to the needle tip.

In at least one embodiment, the at least one needle may include a needle shaft and a needle tip which is installable on the needle shaft, and the transfer device may be configured to install the needle tip on the needle shaft, particularly by rotating the needle tip or applying a pushing force to the needle tip.

In at least one embodiment, the at least one needle may include a needle shaft and a first needle tip which is removable from the needle shaft, the transfer device may be configured to remove the first needle tip from the needle shaft, and the transfer device may be configured to install a second needle tip on the needle shaft.

In at least one embodiment, the transfer device may be configured to form a fluid-tight seal against the needle.

In at least one embodiment, the fluid flow passage may comprise a fluid infusion passage and/or a fluid extraction passage.

In at least one embodiment, the fluid flow passage may be configured to receive the needle therein. Furthermore, the at least one needle may include a removable needle tip, the transfer device may comprise a needle tip holder configured to hold the needle tip, and the fluid flow passage may be configured to receive the needle tip holder therein.

In at least one embodiment, the transfer device includes a fluid infusion port and/or a fluid extraction port, a needle tip removal port and/or a needle tip installation port, and a needle receiving port. Furthermore, the fluid flow passage may be in fluid communication with the fluid infusion port and/or the fluid extraction port, the needle tip removal port and/or a needle tip installation port, and the needle holding port.

In at least one embodiment, a method of treating a subject may be provided, with the method comprising extending a needle through skin of the subject from an access port implanted beneath the skin of the subject such that the needle penetrates the skin outward from within the subject to provide an exposed needle portion outside the subject; and coupling a transfer device to the exposed needle portion, wherein the transfer device forms a closed treatment system with the access port which inhibits transfer of environmental contaminants into the treatment system and escape of hazardous material outside the treatment system.

In at least one embodiment, a method of medically treating a body may be provided, with the method comprising piercing a needle through skin of the body from a medical device implanted beneath the skin of the body, wherein the medical device comprises an access port and a catheter coupled to the access port, wherein the access port houses the needle and the catheter is located in a body cavity of the body; and at least one of introducing a fluid into the body cavity with a fluid passage of the medical device and removing a fluid from the body cavity with a fluid passage of the medical device.

In at least one embodiment, the method may further comprise returning the needle beneath the skin of the body such that the needle is concealed within the body.

In at least one embodiment, the fluid passage may extend through the needle, the access port and the catheter.

In at least one embodiment, the method may further comprise removing a removable tip on the needle to open access to the fluid passage after the step of piercing the needle through skin of the body from the medical device implanted beneath the skin of the body.

In at least one embodiment, the method may further comprise performing at least one of the steps of introducing a fluid into the body cavity with the fluid passage of the medical device and removing a fluid from the body cavity with the fluid passage of the medical device after removing the removable tip on the needle to open access to the fluid passage.

In at least one embodiment, the method may further comprise replacing the removable tip on the needle to close access to the fluid passage after performing at least one of the steps of introducing a fluid into the body cavity with the fluid passage of the medical device and removing a fluid from the body cavity with the fluid passage of the medical device.

In at least one embodiment, the method may further comprise introducing a fluid into the body cavity with a fluid passage of the medical device and removing a fluid from the body cavity with a fluid passage of the medical device In at least one embodiment, the steps of removing a fluid from the body cavity with a fluid passage of the medical device and introducing a fluid into the body cavity with the fluid passage of the medical device may be performed during a dialysis procedure. Further, the body cavity may be the peritoneal cavity, and the dialysis procedure may be a peritoneal dialysis procedure.

In at least one embodiment, the step of removing a fluid from the body cavity with a fluid passage of the medical device may be performed before the step of introducing a fluid into the body cavity with the fluid passage of the medical device.

In at least one embodiment, the step of removing a fluid from the body cavity with a fluid passage of the medical device may further comprise removing a spent dialysis fluid from the body cavity with a fluid passage of the medical device, and the step of introducing a fluid into the body cavity with the fluid passage of the medical device may further comprise introducing a fresh dialysis fluid into the body cavity with the fluid passage of the medical device.

In at least one embodiment, the access port may include an access port body; and the step of piercing a needle through skin of the body from a medical device implanted beneath the skin of the body may be performed while extending the needle from the access port body. In at least one embodiment, the step of extending the needle from the access port body may be performed by moving the needle relative to the access port body.

In at least one embodiment, the step of moving the needle relative to the access port body may be performed by at least one of a magnetic actuation, mechanical actuation and electro-mechanical actuation.

In at least one embodiment, the step of extending the needle from the access port body may be performed by moving the access port body relative to the needle.

In at least one embodiment, the step of moving the access port body relative to the needle may be performed by compressing the access port body.

In at least one embodiment, the access port body may comprise an access port body first member and an access port body second member, and the step of compressing the access port body may be performed by moving at least one of the access port body first member and the access port body second member relative to the other access port body member.

In at least one embodiment, the step of compressing the access port body may be performed by deforming the access port body.

In at least one embodiment, the access port may include an access port body, and the step of returning the needle beneath the skin of the body such that the needle is concealed within the body may be performed while retracting the needle into the access port body.

In at least one embodiment, the step of retracting the needle into the access port body may be performed by moving the needle relative to the access port body.

In at least one embodiment, the step of moving the needle relative to the access port body is performed by at least one of a magnetic actuation, mechanical actuation and electro-mechanical actuation.

In at least one embodiment, the step of retracting the needle into the access port body may be performed by moving the access port body relative to the needle.

In at least one embodiment, the step of moving the access port body relative to the needle may be performed by decompressing the access port body.

In at least one embodiment, the access port body may comprise an access port body first member and an access port body second member, and the step of decompressing the access port body may be performed by moving at least one of the access port body first member and the access port body second member relative to the other access port body member.

In at least one embodiment, the step of decompressing the access port body may be performed by deforming the access port body.

FIGURES

The above-mentioned and other features of this disclosure, and the manner of attaining them, may become more apparent and better understood by reference to the following description of embodiments described herein taken in conjunction with the accompanying drawings, wherein:

FIG. 3b illustrates a cross-sectional view of the embodiment of the medical device of FIG. 3a, with the needle of the access port in an exposed position relative to the access port body and the needle tip removed;

FIG. 4a illustrates a cross-sectional view of another embodiment of a medical device comprising an access port and a catheter according to the present disclosure, with a needle of the access port in a concealed position relative to the access port body;

Figure 9C:
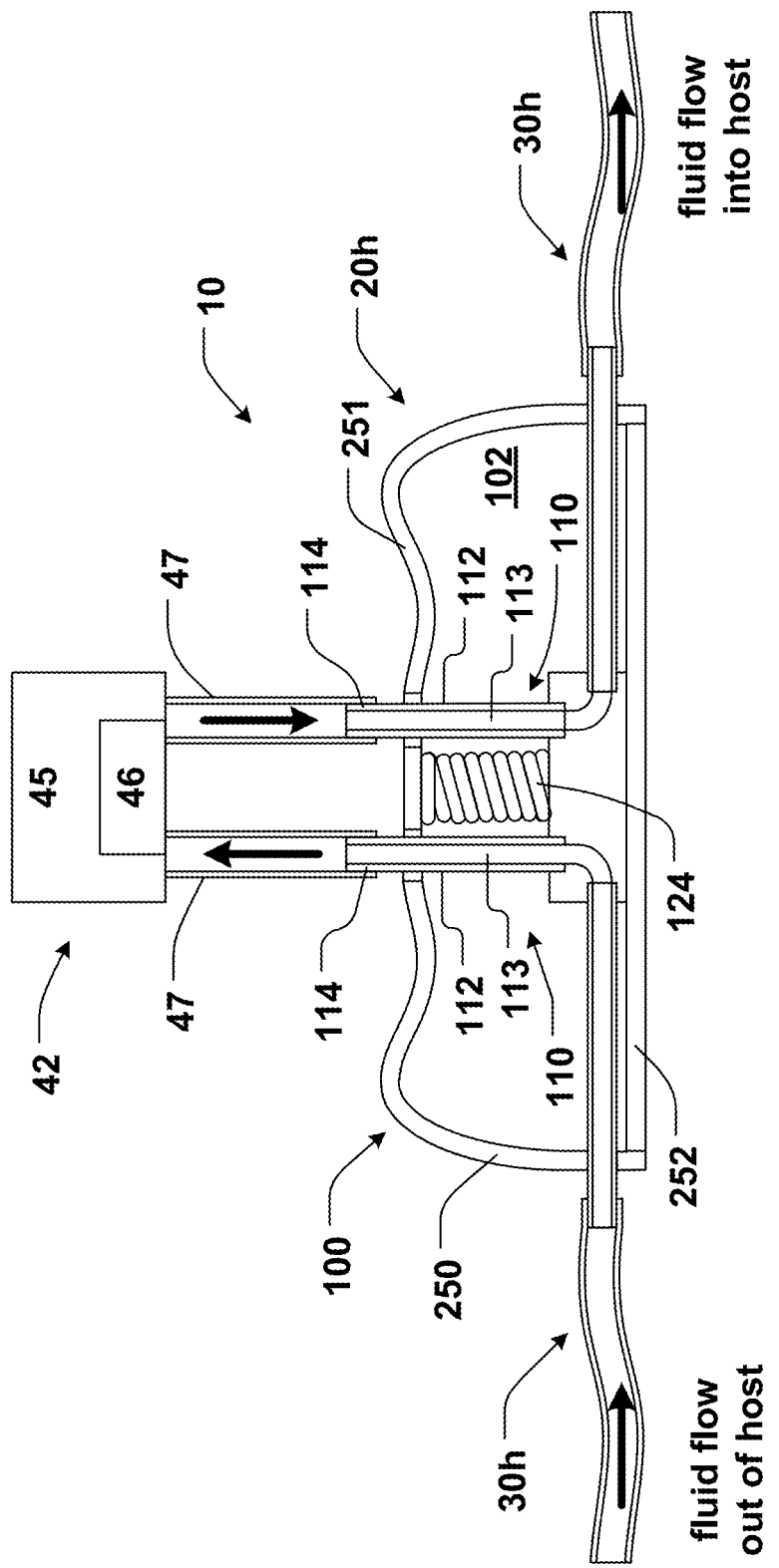
FIG. 9c illustrates a cross-sectional view of the embodiment of the medical device of FIG. 9a, with the needles of the access port in an exposed position relative to the access port body and coupled to a fluid infusion and/or extraction apparatus to form an extracorporeal circuit with the host.
Figure 9F:
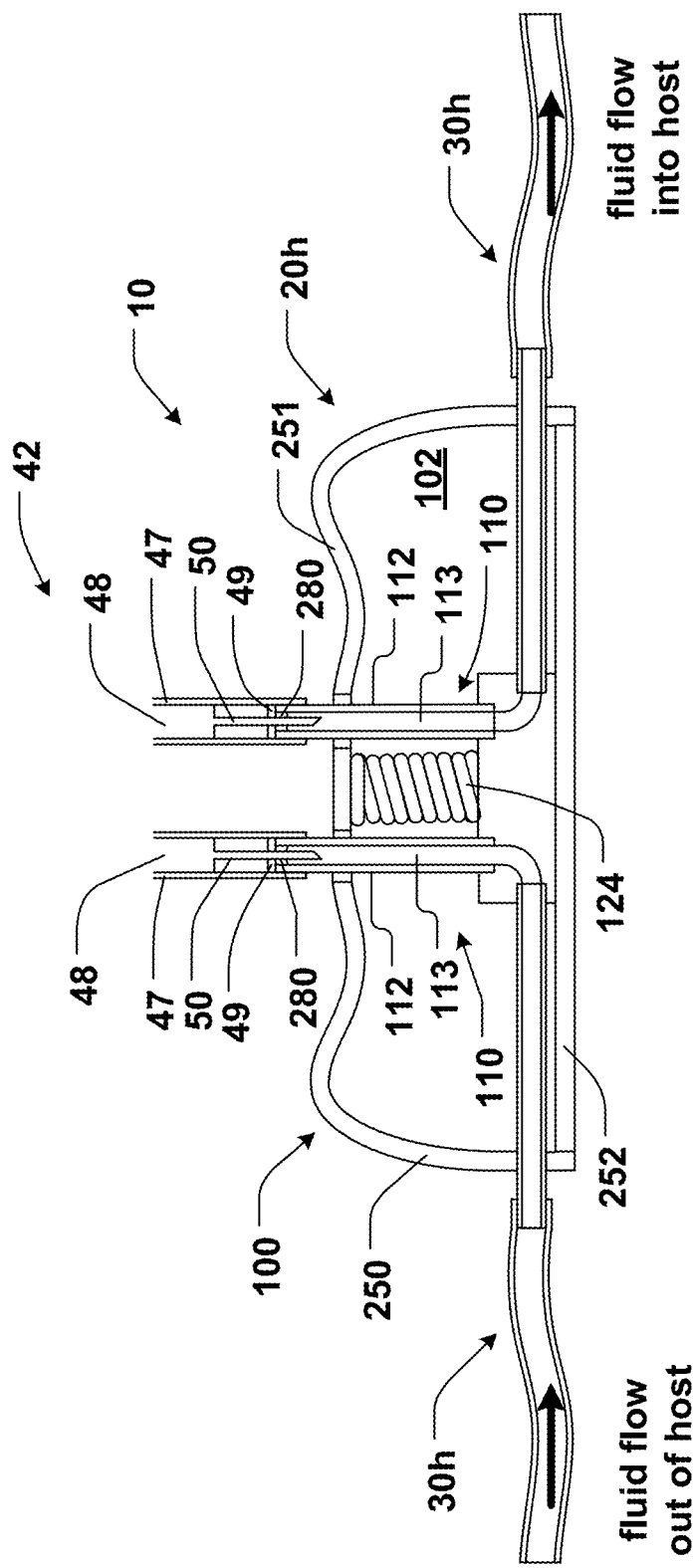
FIG. 9a illustrates a cross-sectional view of another embodiment of a medical device comprising an access port and two catheters according to the present disclosure, with two needles of the access port in a concealed position relative to the access port body.
FIG. 9b illustrates a cross-sectional view of the embodiment of the medical device of FIG. 9a, with the needles of the access port in an exposed position relative to the access port body and the needle tips removed.
Figure 10G:
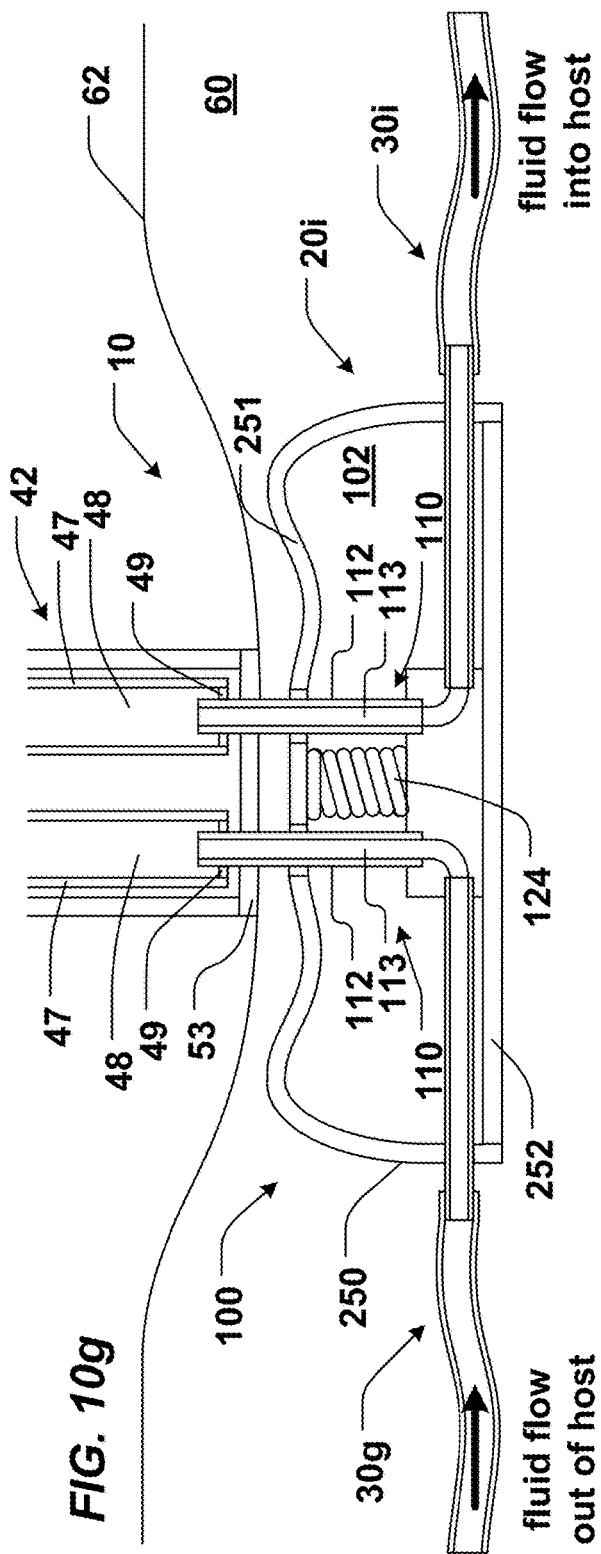
Figure 10F:
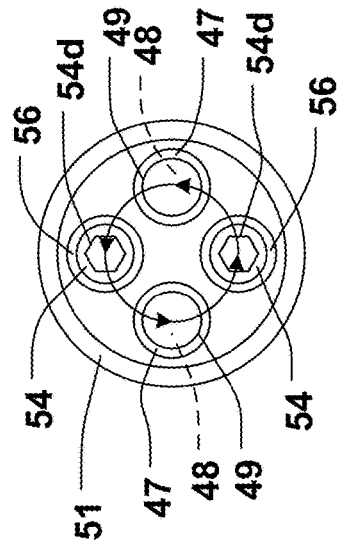
Figure 10B:
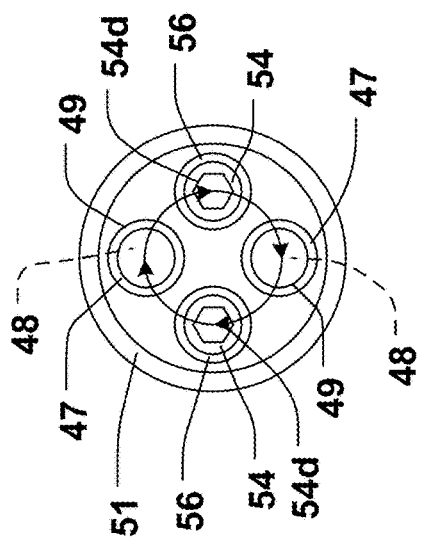
Figure 11A:
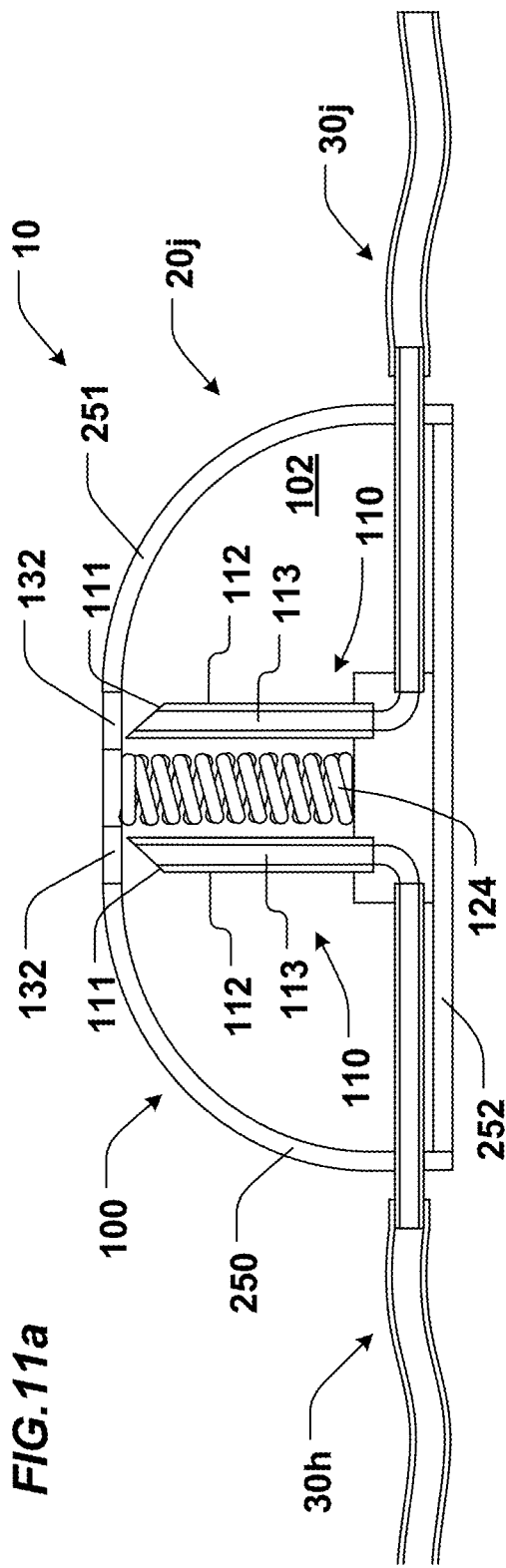
Figure 11B:
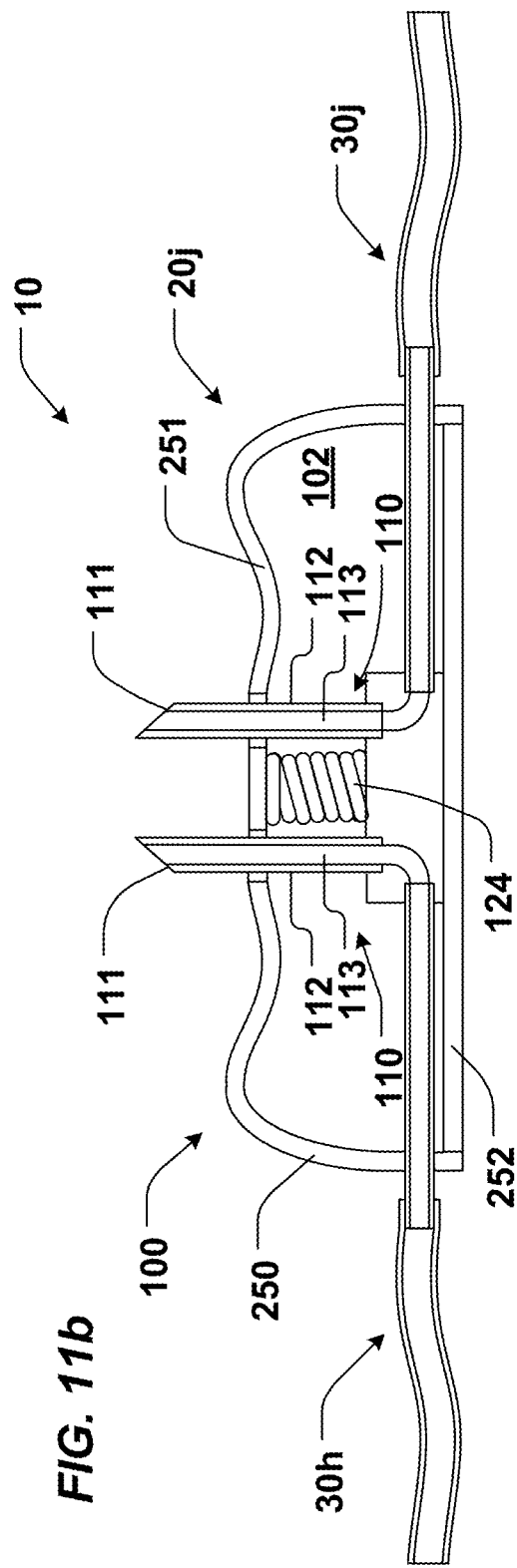
Figure 12B:
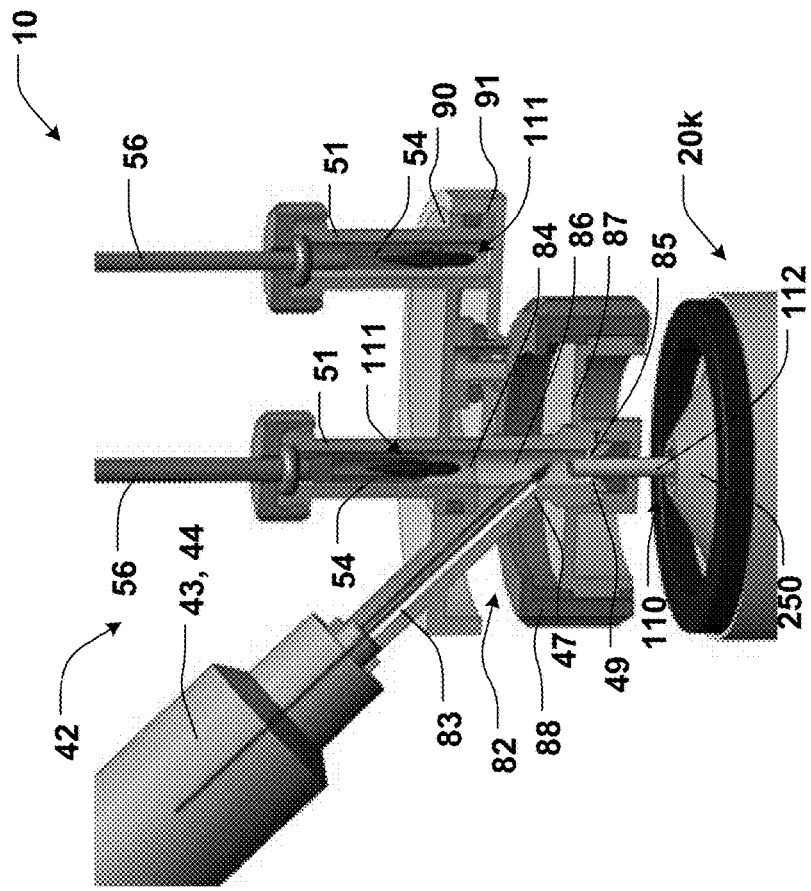
Figure 12A:
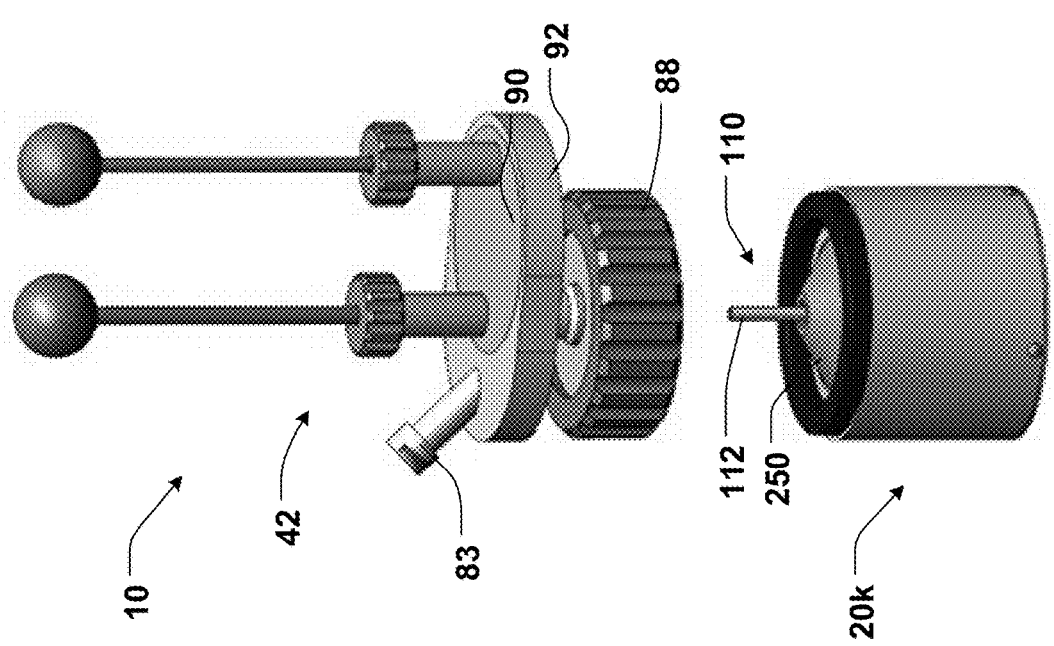

FIG. 9d illustrates a cross-sectional view of another embodiment of a medical device, and more particularly a closed system (drug) transfer device, comprising an access port and two catheters according to the present disclosure, with two needles of the access port in an exposed position relative to the access port body and the needle tips removed prior to the needles being coupled to a fluid infusion and/or extraction apparatus;

FIG. 9e illustrates a cross-sectional view of the medical device, and more particularly the closed system (drug) transfer device of FIG. 9d, with the needles of the access port coupled to the fluid infusion and/or extraction apparatus, and with needles of the fluid infusion and/or extraction apparatus in a retracted position;

FIG. 9f illustrates a cross-sectional view of the medical device, and more particularly the closed system (drug) transfer device of FIG. 9d, with the needles of the access port coupled to the fluid infusion and/or extraction apparatus, and with needles of the fluid infusion and/or extraction apparatus in an extended position, to form an extracorporeal circuit with the host;

FIG. 9g illustrates a cross-sectional view of the embodiment of the medical device of FIG. 9a, with the needles of the access port in an exposed position relative to the access port body and coupled to a fluid infusion and/or extraction apparatus which comprises a cleaning apparatus;

FIG. 9h illustrates a close-up view of the medical device of FIG. 9g as bounded by circle 9h;

FIG. 9i illustrates a cross-sectional view of the medical device of FIG. 9g taken along line 9i-9i of FIG. 9h;

FIG. 10a illustrates a cross-sectional view of another embodiment of a medical device, and more particularly a closed system (drug) transfer device, comprising an access port and two catheters according to the present disclosure, with two needles of the access port in a concealed position relative to the access port body prior to the needles being coupled to a fluid infusion and/or extraction apparatus;

FIG. 10b is a cross-sectional view taken along line 10b-10b of FIG. 10a;

FIG. 10c illustrates a cross-sectional view of the embodiment of a medical device, and more particularly a closed system (drug) transfer device of FIG. 10a, with the two needles of the access port in an exposed position relative to the access port body, after the needles are coupled to the fluid infusion and/or extraction apparatus and before the needle tips are removed;

FIG. 10d illustrates a cross-sectional view of the embodiment of a medical device, and more particularly a closed system (drug) transfer device of FIG. 10a, with the two needles of the access port in an exposed position relative to the access port body, after the needles are coupled to the fluid infusion and/or extraction apparatus and after the needle tips are removed;

FIG. 10e illustrates a cross-sectional view of the embodiment of a medical device, and more particularly a closed system (drug) transfer device of FIG. 10a, with the two needles of the access port in an exposed position relative to the access port body, after the needles are coupled to the fluid infusion and/or extraction apparatus, after the needle tips are removed and before the needles are coupled to fluid infusion and/or extraction members;

FIG. 10f is a cross-sectional view taken along line 10f-10f of FIG. 10e;

FIG. 10g illustrates a cross-sectional view of the embodiment of a medical device, and more particularly a closed system (drug) transfer device of FIG. 10a, with the two needles of the access port in an exposed position relative to the access port body, after the needles are coupled to the fluid infusion and/or extraction apparatus, after the needle tips are removed and after the needles are coupled to fluid infusion and/or extraction members to form an extracorporeal circuit with the host;

FIG. 11a illustrates a cross-sectional view of another embodiment of a medical device, and more particularly a closed system (drug) transfer device, comprising an access port and two catheters according to the present disclosure, with two needles of the access port in a concealed position relative to the access port body;

FIG. 11b illustrates a cross-sectional view of the embodiment of the medical device, and more particularly a closed system (drug) transfer device of FIG. 11a, with the needles of the access port in an exposed position relative to the access port body;

FIG. 11c illustrates a cross-sectional view of another embodiment of a medical device, and more particularly a closed system (drug) transfer device, comprising an access port and two catheters according to the present disclosure, with two needles of the access port in a concealed position relative to the access port body prior to the needles being coupled to a fluid infusion and/or extraction apparatus;

FIG. 11d illustrates a cross-sectional view of the embodiment of a medical device, and more particularly a closed system (drug) transfer device of FIG. 10c, comprising the access port and the two catheters according to the present disclosure, with the two needles of the access port in an exposed position relative to the access port body, after the needles are coupled to the fluid infusion and/or extraction apparatus to form an extracorporeal circuit with the host;

FIG. 12a illustrates a perspective view of another embodiment of a medical device, and more particularly an access port and a closed system (drug) transfer device, and FIG. 12b illustrates a close-up cross-sectional perspective view of the medical device, and more particularly an access port and a closed system (drug) transfer device of FIG. 12a.

DETAILED DESCRIPTION

It is to be understood that this disclosure is not limited in its application to the details of construction and the arrangement of components set forth in the following description or illustrated in the drawings. The invention(s) herein are capable of other embodiments and of being practiced or of being carried out in various ways. Also, it should be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings.

By way of general overview, the present disclosure provides medical devices, systems and methods, and more particularly provides indwelling access devices, systems and methods which may comprise an implantable, subcutaneous, indwelling access port, which may be coupled with one or more implantable, subcutaneous, indwelling catheters within a body, particularly a human body.

The access port may include an access port body containing at least one exposable/concealable (e.g. extendable/retractable) internal needle that may extend/retract relative to the access port body to expose/conceal the internal needle. The access port may also include an access port body containing at least one exposable/concealable internal needle and having an access port body that is configured to compress (collapse) to expose the internal needle and configured to decompress (expand) to expose the internal needle.

Upon implantation of the access port in a human body, the internal needle(s) may be particularly configured to puncture through the skin of the body from beneath the skin, providing access to the port. In certain embodiments, a catheter or other device may be coupled to the needle(s) when exposed through the skin to infuse a fluid (liquid) to the body of the host (e.g. patient or other subject) and/or extract a fluid from the body of the host. For example, the needle(s) may puncture a stopper of a vial, or other seal of another fluid source, and a fluid stored in the vial or the other fluid source may flow from the fluid source through the needle and into the body.

While multiple embodiments of medical devices, systems and methods may be disclosed herein, it should be understood that any particular feature(s) of a particular exemplary embodiment may be equally applied to any other exemplary embodiment(s) of this specification as suitable. In other words, features between the various exemplary embodiments described herein are interchangeable as suitable, and not exclusive.

Figure 1A:
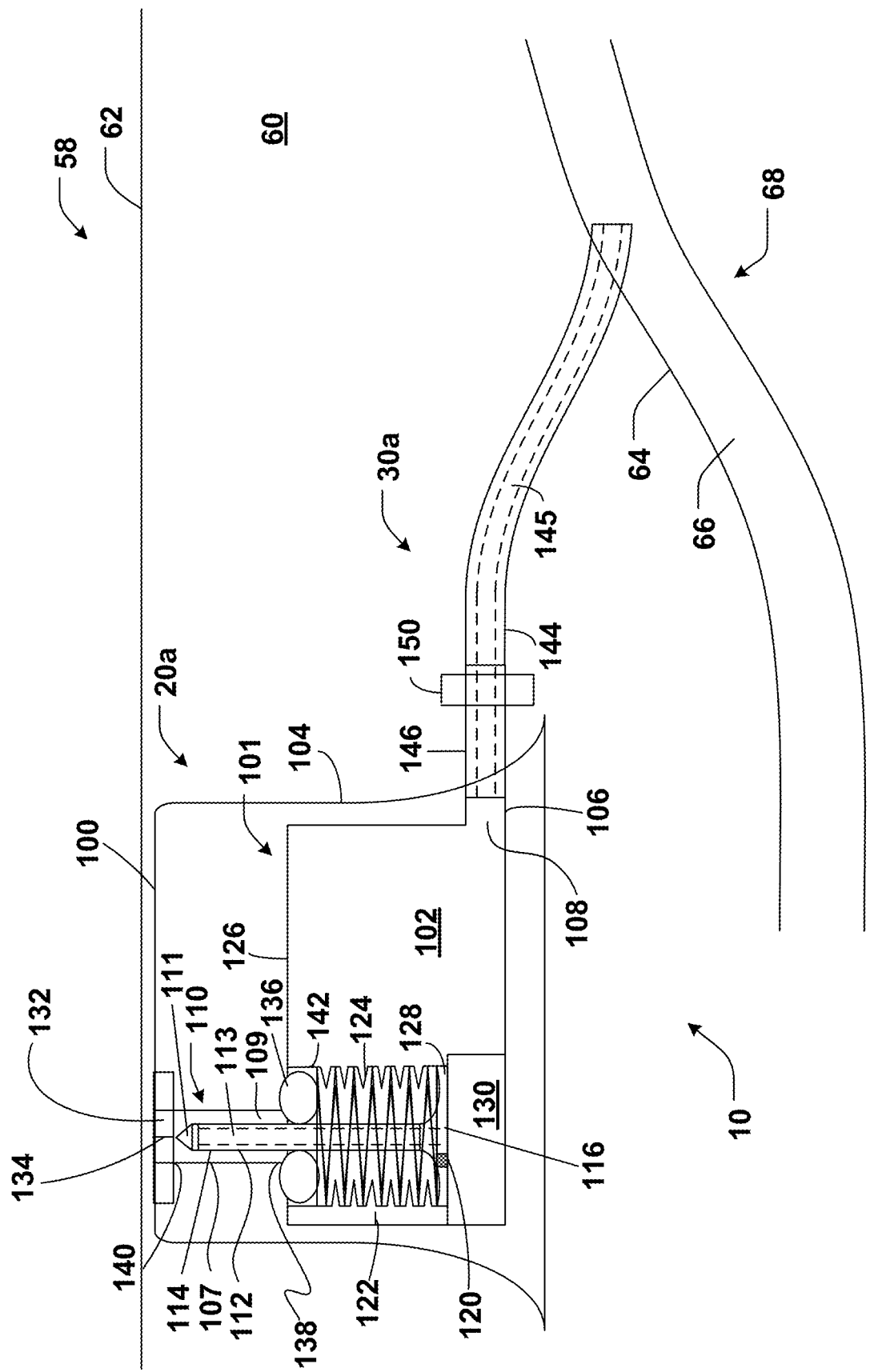
FIG. 1a illustrates a cross-sectional view of a first embodiment of a medical device comprising an access port and a catheter according to the present disclosure, with a needle of the access port in a concealed position relative to the access port body and the catheter in a blood vessel.
Figure 1B:
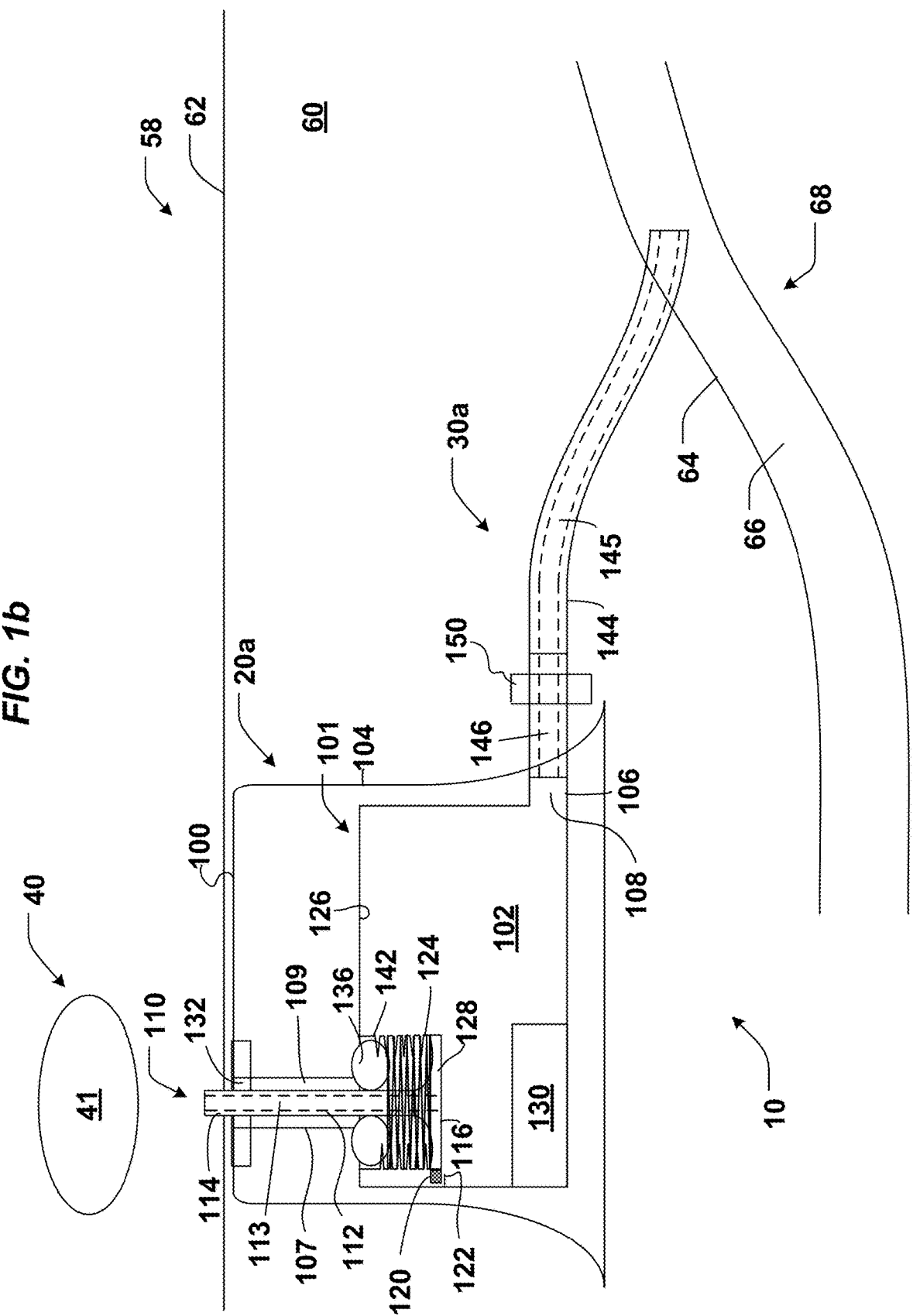
FIG. 1b illustrates a cross-sectional view of the embodiment of the medical device of FIG. 1a, with the needle of the access port in an exposed position relative to the access port body and the needle tip removed.

Referring now to the figures, and in particular FIGS. 1a and 1b, there is shown a first embodiment of a medical device 10 according to the present disclosure implanted in a body of a host 58, such as a patient or other subject, who may be undergoing medical treatment or diagnosis. Medical device 10 may comprise an implantable (subcutaneous), indwelling access port 20a and an implantable (subcutaneous), indwelling catheter 30a coupled to the access port 20a.

As shown, the medical device 10 is implanted beneath the surface 62 of tissue 60, such as cutaneous (skin) tissue, and the indwelling catheter 30a may extend from the access port 20a through a vessel wall 64 and into a lumen 66 of a blood vessel 68 in the tissue 60 of the host 58. In such manner, lumen 145 of catheter body 144 and lumen 66 of blood vessel 68 are in fluid communication. In such application, access port 20a may be understood to comprise a vascular access port.

As shown in FIG. 1a, the access port 20a includes a needle 110, particularly a pointed, closed tip, hollow needle, contained and housed within access port body 100. As shown in FIG. 1a, the needle 110 is in a concealed/retracted position relative to the access port body 100, and includes a pointed, removable, needle (dilator) tip 111 removably coupled to a distal end portion 114 of the needle shaft 112, which closes the distal end of shaft lumen 113. As shown in FIG. 1b, needle 110 is in an exposed/extended position relative to the access port body 100, and the removable pointed tip 111 has been removed to expose and provide access to lumen 113.

The needles 110 contemplated herein, may include any hollow cylinder or shaft 112. Furthermore, the needles 110 may exhibit an outer diameter in the range of 0.1 mm to 4.6 mm, including all values and increments therein. In addition, the needles 110 may exhibit an inner diameter in the range of 0.08 mm to 4.0 mm, including all values and increments therein. Furthermore, the needles 110 may exhibit a nominal wall thickness in the range of 0.002 mm to 0.4 mm including all values and increments therein. The needles 110 may be formed of stainless steel, ceramic composites, or other materials. In addition, the needles 110 or the needle tips 111 may be replaceable in case of dulling. The needles 110 may have gauge sizes in a range of 7 gauge to 34 gauge (e.g. 7, 8, 9, 10, 11, 12, 13, 14, 15, 16, 17, 18, 19, 20, 21, 22 23, 24, 25, 26, 27, 28, 29, 30, 31, 32, 33, 34 gauge), including all values and increments therein, with the gauge size derived from the Stubs (a/k/a/ Birmingham) gauge. More particularly, the needles 110 may have gauge sizes in a range of 11 gauge to 23 gauge, and more particularly in the range of 14 gauge to 17 gauge. The needle shaft 112 may be blunt (square) distal end which may receive removable tip 111, or include, in some examples, standard bevels, short bevels, true short bevels, etc. which do not receive a removable tip 111.

The removable tip 111 may be removably secured to the shaft 112, such as by threaded engagement of opposing threads on each component, or by an interference (press) fit. A proximal end portion 116 of the needle shaft 112 may be secured within the access port body 100 against inadvertent removal from the access port 20a. The needle 110 may be made of a ferromagnetic material, or may include a ferromagnetic material at the distal end portion 114. Examples of ferromagnetic material include iron, nickel and/or cobalt. The access port body 100 may include an external surface 104 and an internal fluid flow passage 101 which may allow fluid to flow through the access port 20a in either direction as described herein. Access port body 100 may include a fluid containment chamber 102, which may optionally provide a reservoir for fluid to be stored within the access port 20a.

The access port 20a may also include first and second bores 106, 107 on different sides of the chamber 102 which provide tubular passages 108, 109, respectively, connecting or providing fluid communication between the chamber 102 and the external surface 104 of the access port 20a. Needle 110 may be positioned within bore 107/passage 109 and may extend from and/or retract into the access port body 100 relative to a outer self-closing seal 132, such as a "self healing" silicone septum described below. Thus, within access port body 100, the internal fluid flow passage 101 which allows fluid to pass through access port 20a may be understood to be formed by chamber 102, tubular passage 108 and lumen 113 of needle 110.

To extend the needle 110 as shown in FIG. 1b, an actuator 40 comprising a magnet 41, such as an electro-magnet, may be positioned closely over (adjacent within about 10 mm, and more particularly within about 5 mm) or on the needle 110, or it may be positioned closely over or on a device to which the needle 110 may attach. When an electric current of a first polarity is provided to magnet 41, magnet 41 may emit an electro-magnetic field arranged with a first polarity which attracts needle 110. The needle 110, being attracted (pulled) towards the magnet 41 by the electro-magnetic force of the electro-magnetic field, may be exposed by extending outwards from the access port body 100 of the access port 20a towards the magnet 41 and out of the host 58 by piercing through the skin surface 62 from within tissue 60.

The tip 111 of the needle 110 is designed to operate as a dilator during and after the distal (terminal) pointed end of the tip 111 (which may be referred to as a pencil tip) has penetrated through tissue 60. With the configuration as shown, the tip 111 of the needle dilates the tissue 60, rather than cutting through the tissue 60 as may be encountered with a large bore, pointed hypodermic needle, to reduce injury.

Alternatively, when it becomes desirable to retract the needle 110 back into the access port body 100 of the access port 20a, after the tip 111 has been placed on needle shaft 112, an electric current of a second polarity opposite the first polarity (i.e. reverse polarity) is provided to magnet 41. Magnet 41 may then emit an electro-magnetic field arranged with a second polarity which repels the needle 110 from the magnet 41, in which case the needle 110 will be pushed away from the magnet 41 by the force of the electromagnetic field and retract inwards relative to access port body 100 and the host 58 to be concealed. As the needle 110 travels inwards in access port body 100, needle 110 correspondingly retracts and withdraws into cutaneous (skin) tissue 60.

It may also be possible to extend and retract the needle 110 using a permanent magnet 41, and reorientating the polarity during use of the magnet 41 to accommodate extension and retraction of needle 110.

In certain embodiments, after the needle 110 is extended, rotation of the needle 110 may lock the needle 110 in place against retraction. For example, the proximal end portion 116 of the needle 110 may include a projection 120 that may engage or otherwise cooperate with a needle lock mechanism 122, such as by rotating onto a catch or into a channel, provided in the chamber 102 at a predetermined location.

In addition, in certain embodiments the magnet 41 may be positioned on or within the device to which the needle 110 may be affixed to administer a given fluid (liquid) composition. For example, the magnet 41 may be positioned proximal to the lip of a vial, near the vial stopper, or in the tip of a catheter into which distal end portion 114 of the needle 110 may be asserted.

In certain embodiments, a needle extension biasing mechanism 124, such as a spring, may be positioned between the proximal end portion 116 of the needle 110 and a chamber wall 126 to retain the needle 110 in the retracted position. As may be appreciated, the force F(s) exerted by the needle extension biasing mechanism 124 on the needle 110 towards the retracted position may be less than the force F(m) exerted by the magnet 41, or stated another way, the force F(m) is greater than the force F(s).

In certain embodiments, the needle 110 may include a flare 128 at the proximal end portion 116 which the spring 124 biases against when compressed and needle 110 is in the extended position. In addition, in certain embodiments, a bumper seal 130 may be provided to receive the proximal end portion 116 of the needle 110 in the retracted position to cushion retraction of the needle 110. The bumper seal 130 may also function to close the proximal end portion 116 of the needle lumen 113 to prevent back flow of fluid through the needle 110 when the needle 110 is retracted, particularly in the event the needle 110 does not include closed tip 111. The bumper seal 130 may be formed into the chamber 126 or may be adhered onto the chamber walls.

In certain embodiments, a self-closing seal 132, such as a "self-healing" silicone septum or a duckbill valve, may be provided at the outer end 140 of tubular passage 109. This self-closing seal 132 may be provided alone, or in addition to the bumper seal 130, provided in the chamber 102. The self-closing seal 132 may include an elongated perforation 134 which extends through the thickness of the self-closing seal 132 to allow the needle 110 to more easily pass through upon application of the magnetic force by the magnet 41 of the actuator 40, or other actuators as disclosed herein.

In addition, in certain embodiments, an additional seal 136 (e.g. an O-ring seal) may be provided at the inner end 138 of tubular passage 109 to prevent backflow of the fluid in the chamber 102 into the tubular passage 109. It may be appreciated that further seals may be provided between the inner end 138 of the tubular passage 109 and the outer end 140 of the tubular passage 109. In other embodiments, an expandable and/or collapsible sleeve 142 may be provided over the needle extension biasing mechanism 124 and/or needle 110 preventing mingling of the fluids in the port with the spring surfaces or the exterior surfaces of the needle 110. The sleeve 142 may be accordion like or in the shape of a bellows.

Indwelling catheter 30a, and more particularly catheter body 144 may be removably attached to the access port 20a by a catheter connector 146 (e.g. barbed stem connector) of the access port 20a, or permanently attached to the access port 20a through chemical or mechanical means, including an adhesive, ultrasonic welding, press-fits, etc. The catheter body 144 may be relatively flexible and formed of a composition such as silicone, polyurethane, or other thermoplastic elastomers.

In addition, in some embodiments, a metering device 150 may be provided between chamber 102 of the access port 20a and the catheter 30a. The metering device 150 may include a valve and allow for control of the flow rate of fluid through the access port 20a.

Figure 1C:
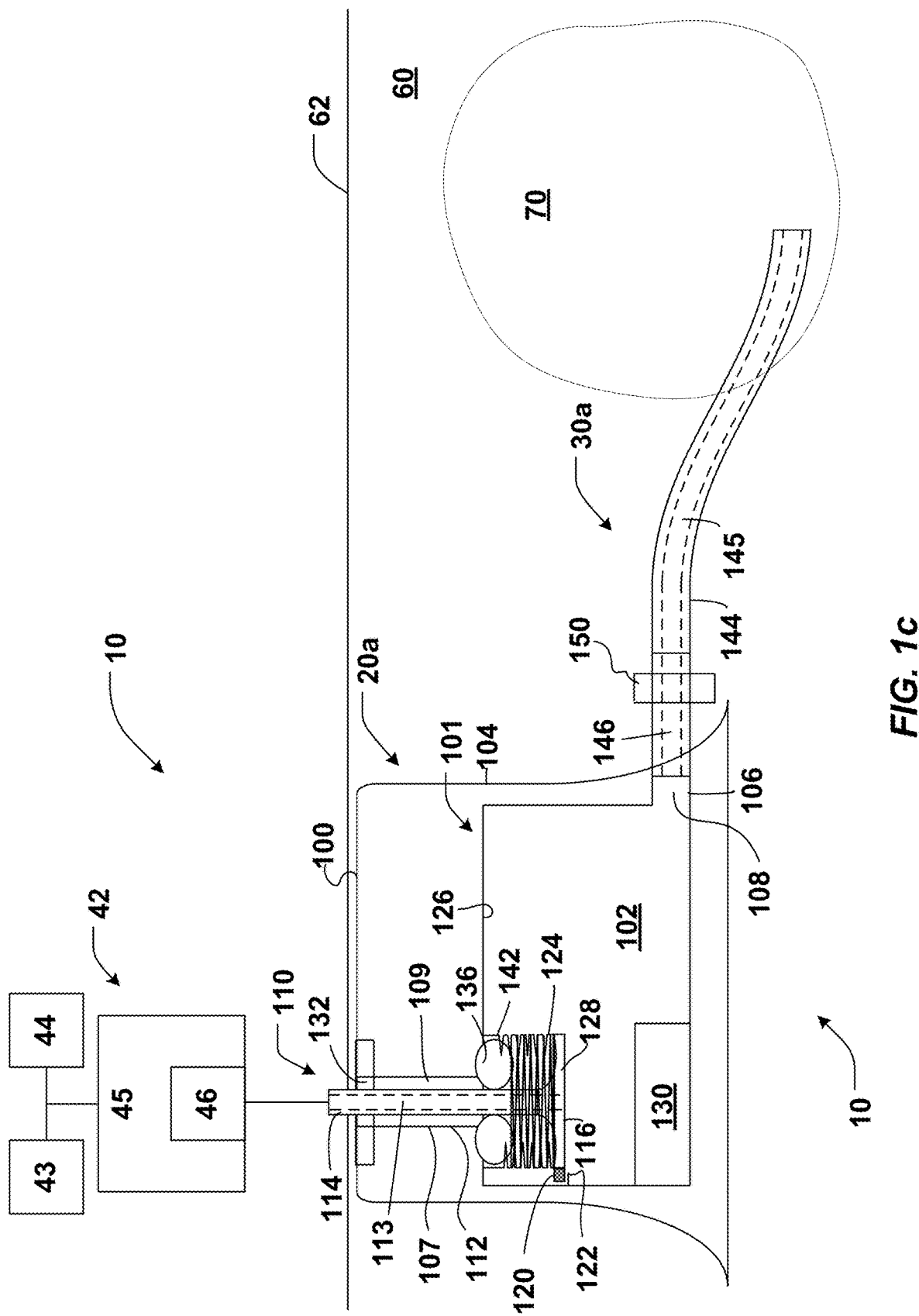
FIG. 1c illustrates a cross-sectional view of the embodiment of the medical device of FIG. 1a, with the needle of the access port in an exposed position relative to the access port body and the catheter in a body cavity.
Figure 1D:
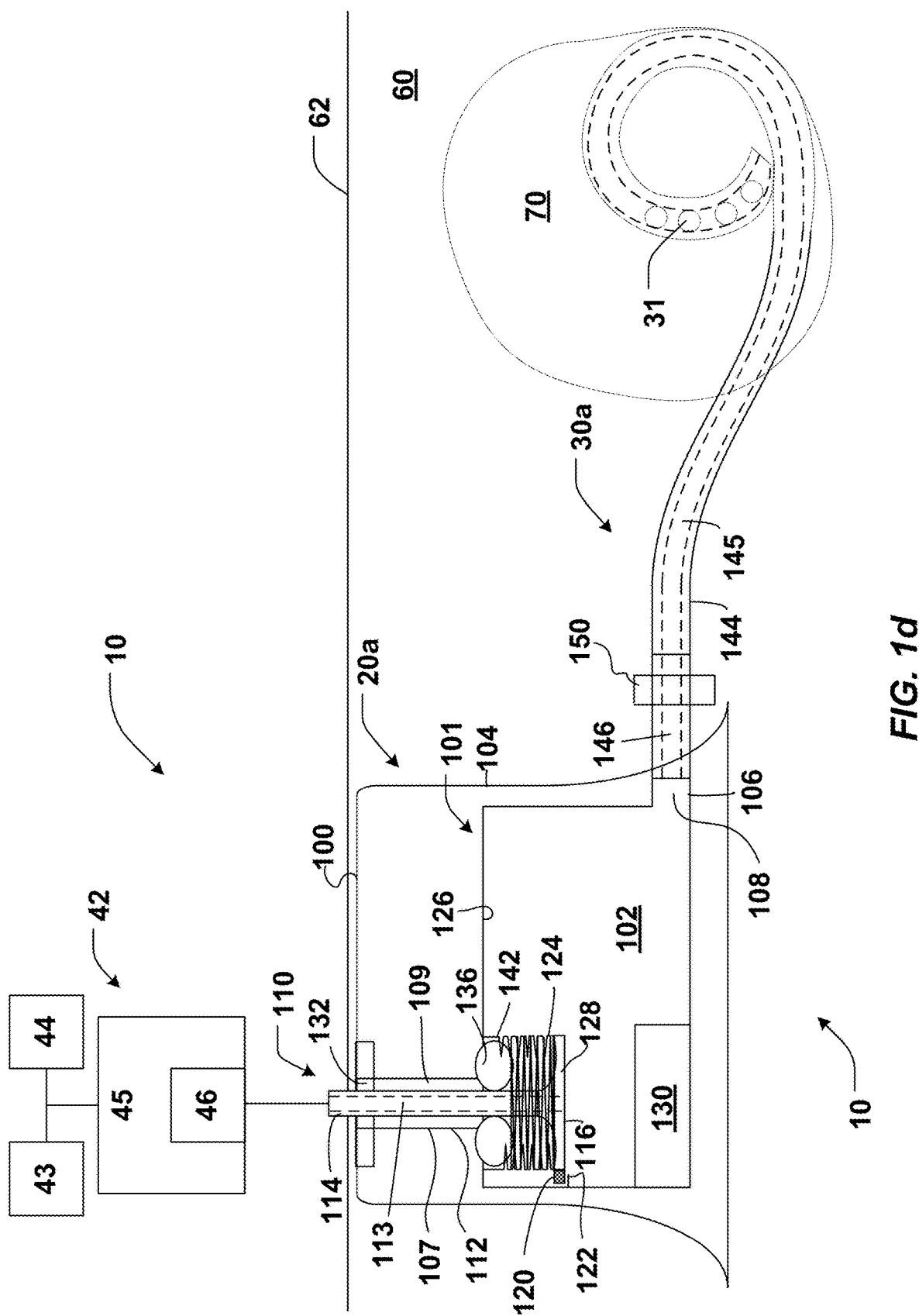
FIG. 1d illustrates a cross-sectional view of the embodiment of the medical device of FIG. 1a, with the needle of the access port in an exposed position relative to the access port body and a pigtail catheter in a body cavity.

Referring now to FIG. 1c, rather than catheter 30a being inserted into blood vessel 68, catheter 30a is shown to be inserted into a body cavity 70. Needle 110 of access port is shown in its extended position with pointed tip 111 removed, and is in fluid communication with a fluid source 43 and a fluid receptacle 44. As such, fluid may flow through lumen 113 of needle, into fluid chamber 102 through tubular passage 108 and lumen 145 of catheter 30a, and into body cavity 70, as well as vise-versa. Referring to FIG. 1d, rather than catheter 30a being a straight catheter, catheter 30a may be a pigtail catheter, which may include a number of fluid flow openings 31 in the sidewall in addition to a distal end opening.

Body cavity 70 may more particularly be the abdominal (peritoneal) cavity, and medical device 10 may be implanted in host 58 to perform peritoneal dialysis. Peritoneal dialysis may be a treatment available to patients who suffer from chronic kidney disease and kidney failure.

The peritoneal cavity, one of the serous cavities of the human body, is lined by the peritoneum, which is a serous membrane (or serosa). The peritoneal cavity may be understood as the potential space between the parietal peritoneum and visceral peritoneum, the two membranes that separate the organs in the abdominal cavity from the abdominal wall.

The peritoneal cavity contains peritoneal fluid, which may more broadly understood to be serous fluid (or serosal fluid) which is secreted by the peritoneum. Peritoneal fluid is a liquid that acts as a lubricant in the abdominal cavity, and it is found in small quantities between the parietal peritoneum and visceral peritoneum.

During peritoneal dialysis, dialysis fluid, also known as dialysate, is introduced into the peritoneal cavity through access port 20a and catheter 30a from fluid source 43. During the procedure, the peritoneum is used as a filter, in that waste products are removed from the blood by passing through the peritoneum. However, blood itself does not pass through the peritoneum. During infusion, the dialysis fluid may be pumped into the peritoneal cavity with the aid of a pump 46 which is part of fluid infusion and/or extraction apparatus 42, which may comprise a dialysis apparatus 45.

After a time period in the peritoneal cavity, the now contaminated dialysis fluid may then be removed from the peritoneal cavity, particularly by being drained from the peritoneal cavity. The dialysis fluid may flow through catheter 30a and access port 20a to be contained in fluid receptacle 44. During extraction, the dialysis fluid may be pumped from the peritoneal cavity with the aid of pump 46.

In addition, catheter 30a may also be inserted into the peritoneal cavity with associated use of access port 20a to remove fluid from the peritoneal cavity which has accumulated therein. Such medical condition may be referred to as ascites, peritoneal cavity fluid, peritoneal fluid excess, hydroperitoneum and abdominal dropsy. Although most commonly due to cirrhosis (cirrhotic ascites), severe liver disease or metastatic cancer, its presence can portend other significant medical problems, such as Budd-Chiari syndrome. Removal of fluid may generally be in the range of 2-4 liters, however, it may be necessary to remove more than 5 liters during a single treatment.

Prior to the use of the access port 20a of the present disclosure, in order to perform peritoneal dialysis or otherwise remove fluid from the peritoneal cavity, an incision has been created through the abdominal wall to the peritoneal cavity into which a peritoneal dialysis catheter having a length of approximately 12 inches is inserted. Approximately half the length of the catheter is placed inside the peritoneal cavity and the remaining six inches pass through the abdominal wall to exit the cavity beneath one side of the navel. The catheter is typically equipped with at least one dacron or felt cuff which surrounds the portion of the catheter located in the incision/subcutaneous passage formed in the abdominal wall. During healing of the incision, the patient's body tissue joins with the cuff, particularly within the interstices thereof, which may create an anchor for the catheter, as well as may provide an infection barrier. Nevertheless, use of the dacron or felt cuff has not been full proof in preventing infection at the exit site. It is believed that the present disclosure provides an alternative to use of the foregoing partially implanted catheter, and may reduce infection rates.

In addition, catheter 30a may also be inserted into other cavities with associated use of access port 20a to remove fluid from other cavities which has accumulated therein. For example, catheter 30a may also be inserted into a pleural cavity with associated use of access port 20a to remove fluid from a pleural cavity which has accumulated therein, i.e. thoracentesis.

The two pleural cavities, serous cavities of the human body, are lined by the pleura, which is a serous membrane. A pleural cavity may be understood as the potential space between the outer pleura (parietal pleura) and the inner pleura (visceral pleura).

Each pleural cavity contains pleural fluid which may more broadly understood to be serous fluid (or serosal fluid) which is secreted by the serous membrane covering normal pleurae. Pleural fluid is produced and reabsorbed continuously, however, excess fluid may accumulate in the pleural cavity, i.e. pleural effusion. This excess fluid may impair breathing by limiting the expansion of the lungs. Various kinds of pleural effusion, depending on the nature of the fluid and what caused its entry into the pleural space, are hydrothorax (serous fluid), hemothorax (blood), urinothorax (urine), chylothorax (chyle), or pyothorax (pus). Pneumothorax is the accumulation of air in the pleural space.

For example, catheter 30a may also be inserted into a cranial (skull) cavity with associated use of access port 20a to remove cerebrospinal fluid from the cranial cavity which has accumulated therein, particularly to treat external hydrocephalus, or from the ventricles of the brain, particularly to treat internal hydrocephalus.

Figure 2:
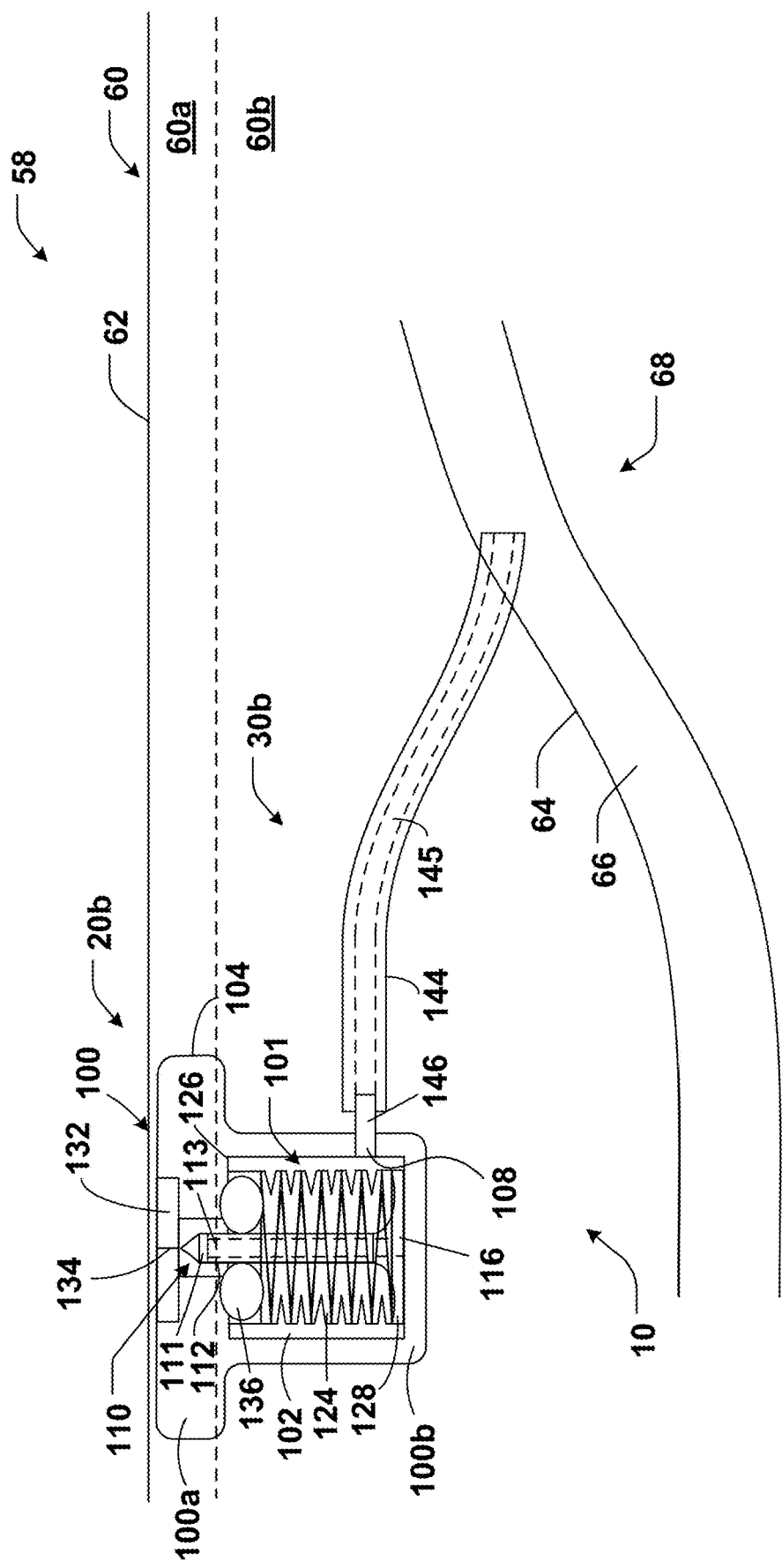
FIG. 2 illustrates a cross-sectional view of another embodiment of the medical device comprising an access port and a catheter according to the present disclosure, which operates in a similar manner to the embodiment of FIG. 1a, with a needle of the access port in a concealed position relative to the access port body and the catheter in a blood vessel.

Referring now to FIG. 2, there is shown an embodiment of the medical device 10 which operates in a same manner as the embodiment of FIG. 1a, with a needle 110 of the access port 20b in a concealed (retracted) position relative to access port body 100 and the catheter 30b in a blood vessel 68. The present embodiment has an access port body 100 which comprises an upper (cylindrical disc) body portion 100a and a lower (cylindrical disc) body portion 110b. As shown, the upper (cylindrical disc) body portion 100a has a cross-sectional height which is less than the lower (cylindrical disc) body portion 110b, while the diameter of the upper (cylindrical disc) body portion 100a is greater than the lower (cylindrical disc) body portion 110b. Also as shown, the upper (cylindrical disc) body portion 100a is particularly configured to reside is the subcutaneous region 60a of tissue 60, while the lower (cylindrical disc) body portion 110b is configured to reside in the muscle tissue 60b. Upon being inserted, the lower (cylindrical disc) body portion 110b may provide a mounting keel to body 100 which holds the body 100 in the desired location and orientation.

Figure 3A:
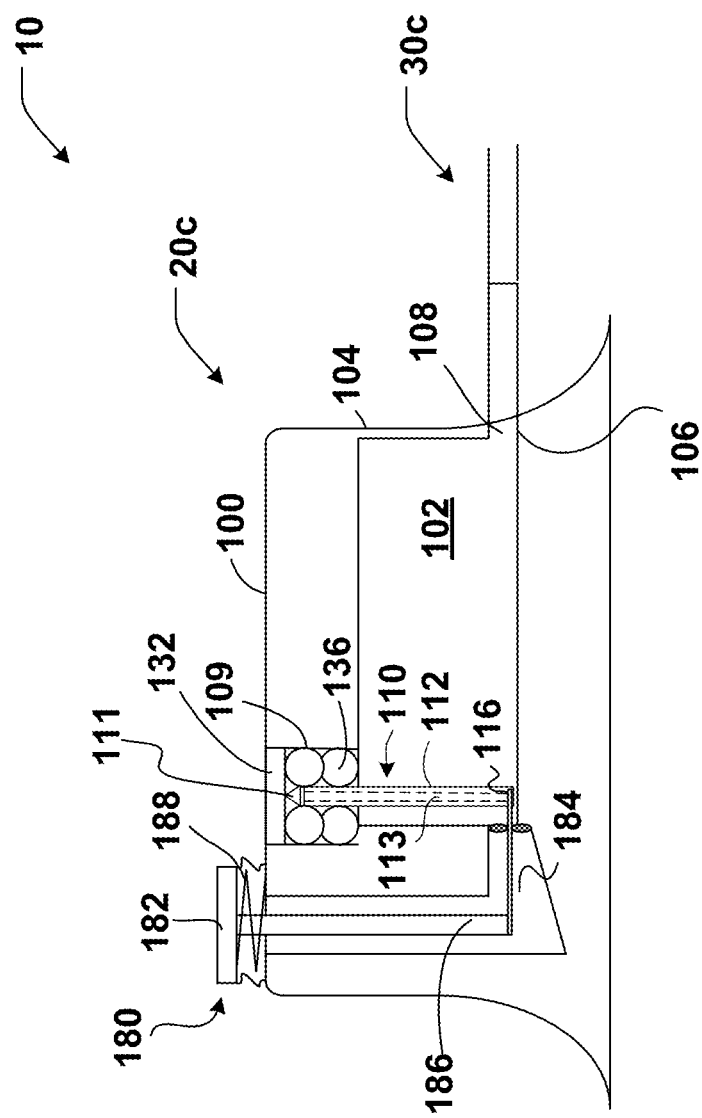
FIG. 3a illustrates a cross-sectional view of another embodiment of a medical device comprising an access port and a catheter according to the present disclosure, with a needle of the access port in a concealed position relative to the access port body.

Referring now to FIGS. 3a and 3b, there is shown another embodiment of a medical device 10 according to the present disclosure, which comprises implantable (subcutaneous), indwelling access port 20c and an implantable (subcutaneous), indwelling catheter 30c coupled to the access port 20c. FIG. 3a shows the needle 110 of access port 20c in the concealed (retracted) position relative to access port body 100, and FIG. 2b shows the needle 110 of access port 20c in the exposed (extended) position relative to access port body 100. In contrast to the first embodiment, needle 110 is retracted and extended by an actuator 40 which comprises a mechanical actuator 180 rather than a magnetic actuator. Furthermore, the mechanical actuator 180 is completely incorporated with the access port 20c.

The access port body 100 may again generally include a chamber 102 defined in the part and an external surface 104. The access port may include a bore 106 providing a tubular passage 108 connecting or providing fluid communication between the chamber 102 and the external surface 104 of the access port 20c. A tubular passage 109 to accommodate the travel of the needle 110 may be provided between the chamber and an external surface of the port. Similar to the prior embodiment, the needle 110 may include a shaft 112, a lumen 113, a distal end portion 114, a proximal end portion 116 and a removable pointed tip 111, which is the same as the prior embodiment. Certain components similar to those shown in the first embodiment are not further discussed here or with other embodiments herein.

The mechanical actuator 180 may include a mechanical linkage. In one embodiment, a push button 182 may be mechanically affixed to a lever 184, which is affixed to the needle, by a first linkage 186. Upon pressing the button 182 inwards, the lever 184 may rotate around a pivot point and raise the needle 110 through the host's skin. Other linkages may be envisioned and are not limited to the linkage herein. Furthermore, a spring 188 may be provided, such as under the button 182, which raises (biases the inward movement of) the button 182 and thereby retract and withdraw the needle 110. Spring 188 may be a coil (helical) spring, torsion spring, conical spring, linear spring or any other suitable spring)

In other embodiments, as with the first embodiment, the needle 110 may be spring loaded, biasing the needle 110 into the retracted position. The button 182 may be directly pressed by a clinician or other person providing a fluid composition into the access port 20c or removing a fluid composition from the access port 20c. However, it may also be envisioned that the button may be pressed by pushing against it with a vial or other container including the composition to be provided to the host, or pressed by the external actuator.

Figure 4B:
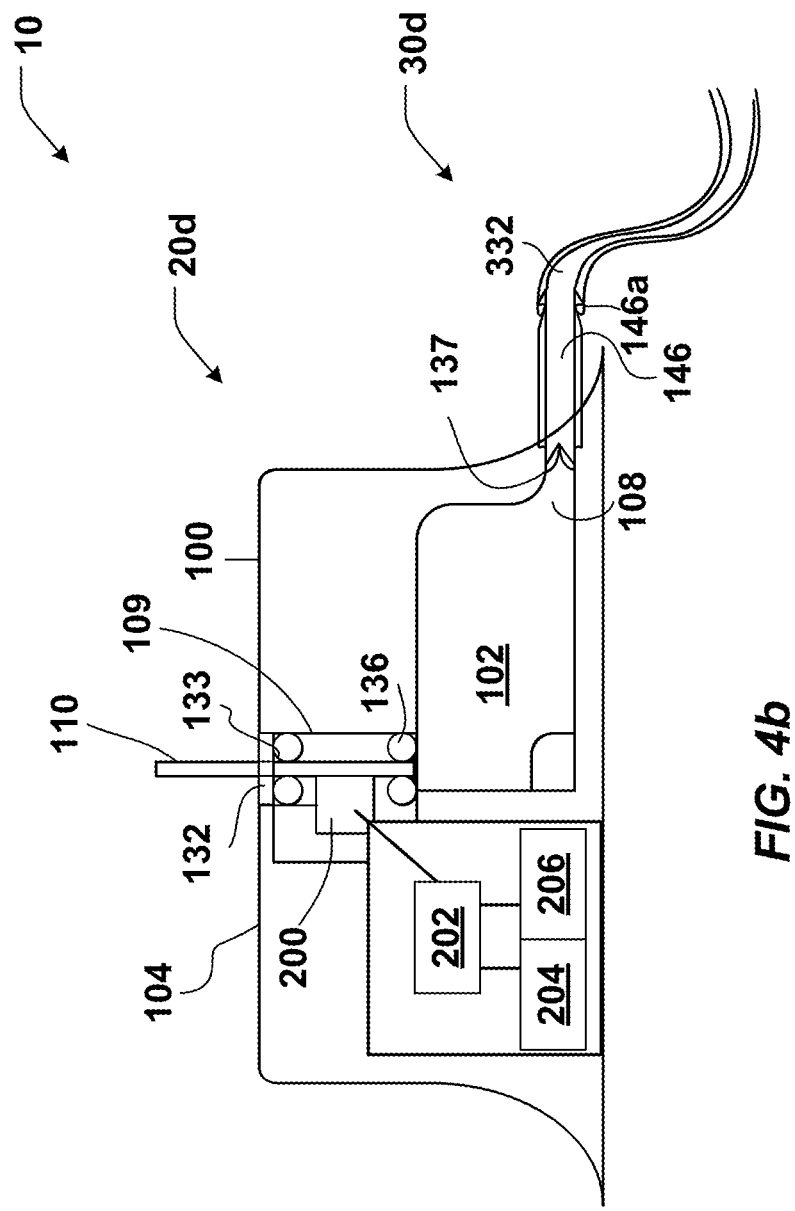
FIG. 4b illustrates a cross-sectional view of the embodiment of the medical device of FIG. 4a, with the needle of the access port in an exposed position relative to the access port body and the needle tip removed.

Referring now to FIGS. 4a and 4b, there is shown another embodiment of a medical device 10 according to the present disclosure, which comprises implantable (subcutaneous), indwelling access port 20*d* and an implantable (subcutaneous), indwelling catheter 30*d* coupled to the access port 20*d*. FIG. 4*a* shows the needle 110 of access port 20*d* in the concealed (retracted) position relate to access port body 100, and FIG. 4*b* shows the needle 110 of access port 20*d* in the exposed (extended) position relative to access port body 100. In contrast to the second embodiment, needle 110 is retracted and extended by an electro-mechanical actuator rather than a purely mechanical actuator.

As shown in FIGS. 4*a* and 4*b*, the access port 20*d* may include a needle 110 that may be extended or retracted by an actuator that comprises an electrical/mechanical device. The access port body 100 may include a chamber 102 defined therein as well as a bore 106 providing a tubular passage 108 that extends from the chamber 102 to an exterior surface 104 of the access port 20*d*, providing communication between the interior (chamber) of the access port 20*d* and the external environment. In addition, the access port 20*d* may include a passage 109, which may accommodate the needle 110 as it extends or retracts with respect to a surface 104 on the body 100 of the access port 20*d*.

The access port 20*d* may also include a motor or other electrical device 200 that may extend or retract the needle 110. Motor 200 may include linear piezoelectric or electromagnetic motors. In some embodiments, the motor 200 may be a piezoelectric micro-motor. The motor 200 may include a linear traveler, such as a shaft or translator. In some embodiments, the shaft or translator may interact with the needle 110 translating the needle 110 up and down relative to the port body 100. In other embodiments, the shaft or linear translator may be the needle 110, having a hollow cylinder defined therein.

In some embodiments, a computer processor 202 may be provided to power the motor 200 and control the direction of needle travel. The processor 202 and motor 200 may be powered by a power supply 204. The power supply 204 may communicate electrically either directly or indirectly with either the processor 202 and/or motor 200. For example, in some cases, the processor 202 may provide power to the motor 200 and in other cases a transformer may be provided either between the power supply 204 and processor 202 and/or between the power supply 202 and the motor 200.

The processor 202 may be actuated by an actuator. In some embodiments, a button 182 or other actuation device may be provided that, when depressed or otherwise activated, may send a signal to the processor 202 to actuate the needle 110. In certain embodiments, the access port 20*d* may include a communication device 206 such as a receiver or transceiver, which may include a receiver. The communication device 206 may be configured to receive or transmit an electromagnetic indicator, such as electromagnetic waves or signals such as radio waves or optical waves, received from a wireless actuator.

For example, the communication device 206 may receive radio waves from an RFID (radio frequency identification) device. The RFID device may be integrated into a tag or card that when brought into proximity with the access port 20*d* may activate the actuator (i.e., the processor) and cause the needle 110 to extend from the access port body 100. In other embodiments, the communication device 206 may detect or receive optical signals. Such signals may be in the range of 200 nm to 900 nm, including all values and increments therein, such as 200 nm to 400 nm (ultraviolet light), 380 nm to 750 nm (visible light), 750 nm to 1400 nm (infrared light). In some embodiments, the optical waves may exhibit a Fraunhofer wavelength, i.e., a wavelength not emitted by the sun, preventing accidental triggering of the device upon exposure to the sun. It may be appreciated that the radio or optical signals may be received or detected at a single wavelength or at multiple wavelengths, including 1 wavelength to 20 wavelengths and all values and increments therein. Other devices that may be used to cause the processor 202 to actuate the motor 200 may include wi-fi, Bluetooth or other transmitters or transceivers including transmitters, light. Furthermore, a light pen, or other light source may be an actuator for the processor 202 to actuate the motor 200.

The electromagnetic indicators may be provided by a transmitter or a transceiver that may include a transmitter in the actuator. The electromagnetic indicators may be pulsed or otherwise manipulated to provide directions or instructions. For example, the indicators may signal for the processor 202 to extend the needle 110 or retract the needle 110. In other embodiments, the indicators may provide an identifier to prevent cross-talk between devices or prevent accidental extension or retraction of the needle 110. The actuator may also include a processor for regulating the signals from the transmitter, which may be in electrical communication with the processor 202.

Figure 5:
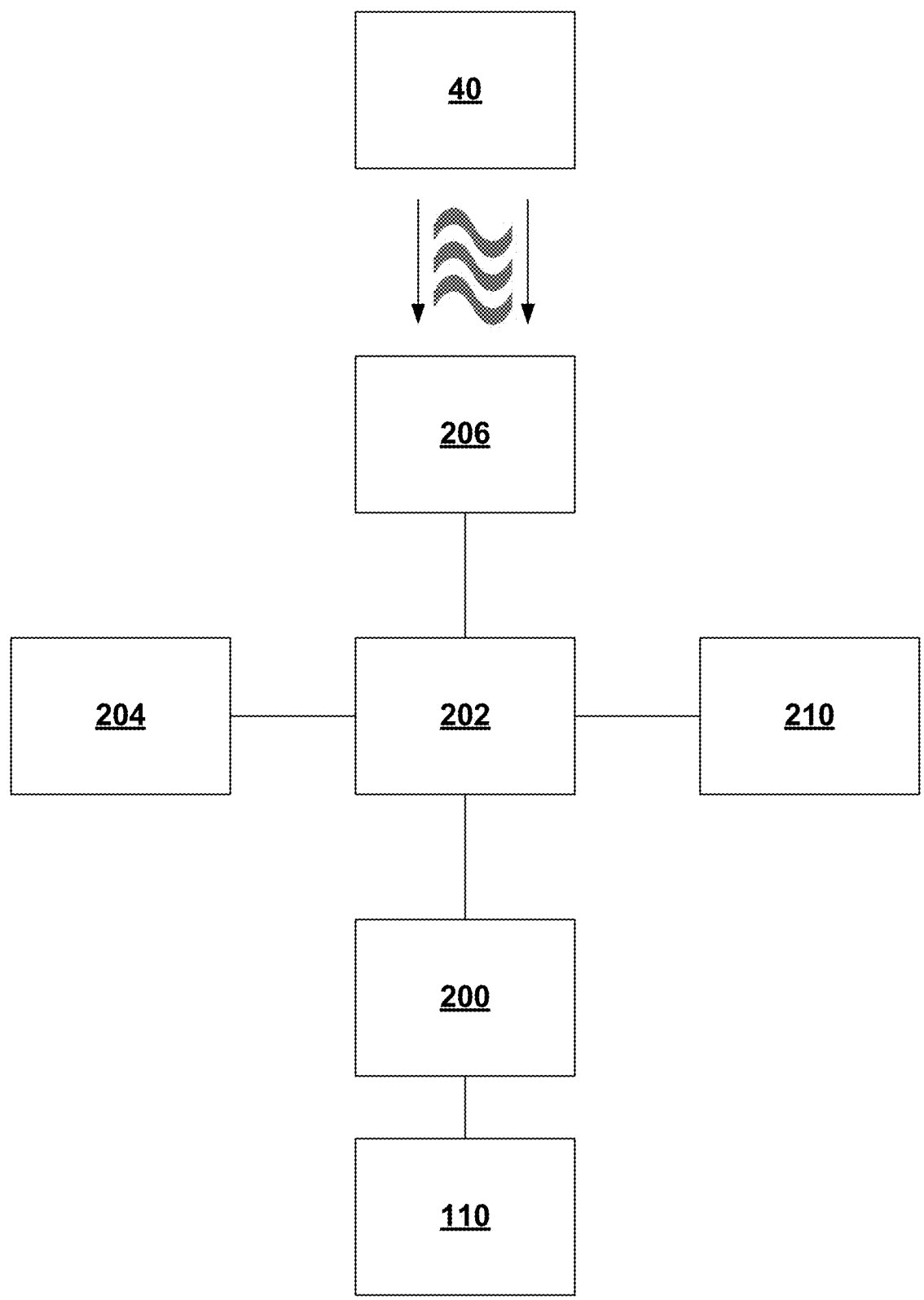
FIG. 5 illustrates a schematic of a control system for a medical device comprising an access port according to the present disclosure.

Accordingly, it may be appreciated that a system may be provided including the access port 20 and an actuator 40. An embodiment of such a system is illustrated in the schematic diagram of FIG. 5, wherein an actuator 40 may emit various electromagnetic signals or waves. Upon receiving the electromagnetic waves, the communication device 206 may convert the waves into electrical pulses that may be communicated to the processor 202.

Depending on the signals received, the processor 202 may perform a number of functions. In some embodiments, the processor 202 may actuate the motor 200 to extend or retract the needle 110. In other embodiments, the processor 202 may identify the received signals as being indentifying information that correlates the actuator 40 with the access port 20. The processor 202 may compare the indentifying information with a lookup table or identifying information stored in a memory device 210. If the identifying information is correct, then the processor 202 may employ any commands that may be received from that device to extend or retract the needle 110. It may be appreciated that identifying information may be transmitted a single time or multiple times, such as with each command. Upon receiving a signal to actuate the motor 200, i.e., extend or retract the needle 110, the processor 202 may send an electrical signal to the motor 200 or provide power to the motor 200 from the power supply 204 such that the motor 200 will displace the linear traveler, extending or retracting the needle 110.

Returning again to FIGS. 4*a* and 4*b*, the body 100 may include a number of seals that may isolate the chamber and the interior of the needle 110. For example, a first seal or set of seals 136 may be provided where the needle 110 extends into the chamber 102. The seal 136 may prevent the fluid composition being injected into the access port 20*d* from flowing back into the passage 109. In certain embodiments, a self-closing seal 132 may be provided at the surface 104 of the body 100. The needle 110 may penetrate the self-closing seal 132 when extended and the self-closing seal 132 may prevent fluids or other contaminants from entering the access port 20*d*. In addition, the self-closing seal 132 may be formed from a self healing composition, such as silicone or natural rubber. In certain embodiments, another seal 133 (e.g. O-ring) may be provided near the surface 104 of the body 100, wherein the seal 133, like the septum, may prevent fluids or other contaminants from entering the access port 20*d*.

The port 20d may also include a connector 146, which may connect to the bore 106 which provides the tubular passage 108 leading into the chamber 102 with a catheter body 144 of catheter 30d. The connector 146 may include barbs 146a or other mechanical interlocks to retain the catheter body 144 on the port 20d. However, it may be appreciated that, in some embodiments, the catheter 20d may be removed from the connector 146. In other embodiments, the catheter 20d may be welded to the port, permanently affixing the catheter to the port.

In addition, as illustrated in the embodiments above, the chamber 102 may be defined to assume different geometries. Accordingly, rather than assuming the geometry of a rather rectangular reservoir, the chamber 102 may assume the shape of an ellipse, oval, circle, shaft or other geometric configurations. In addition, while the needle 110 is illustrated as being positioned on a stopper 130 in the retracted position, it may be appreciated that the needle 110 need not return against another object or may return against a wall of the chamber 102.

Furthermore, with reference to FIG. 4a and FIG. 4b, it may be appreciated that the bore 106/fluid passage 108 may include a seal 137. The seal 137 may allow for fluids to pass out of the bore 106/passage 108 from the chamber 102 and into the connector 146 and/or catheter 30d. However, in some embodiments, the seal 137 may prevent backflow from the connector 146 and/or catheter 30d. For example, in one embodiment, the seal 137 may include a duckbill valve.

Figure 6A:
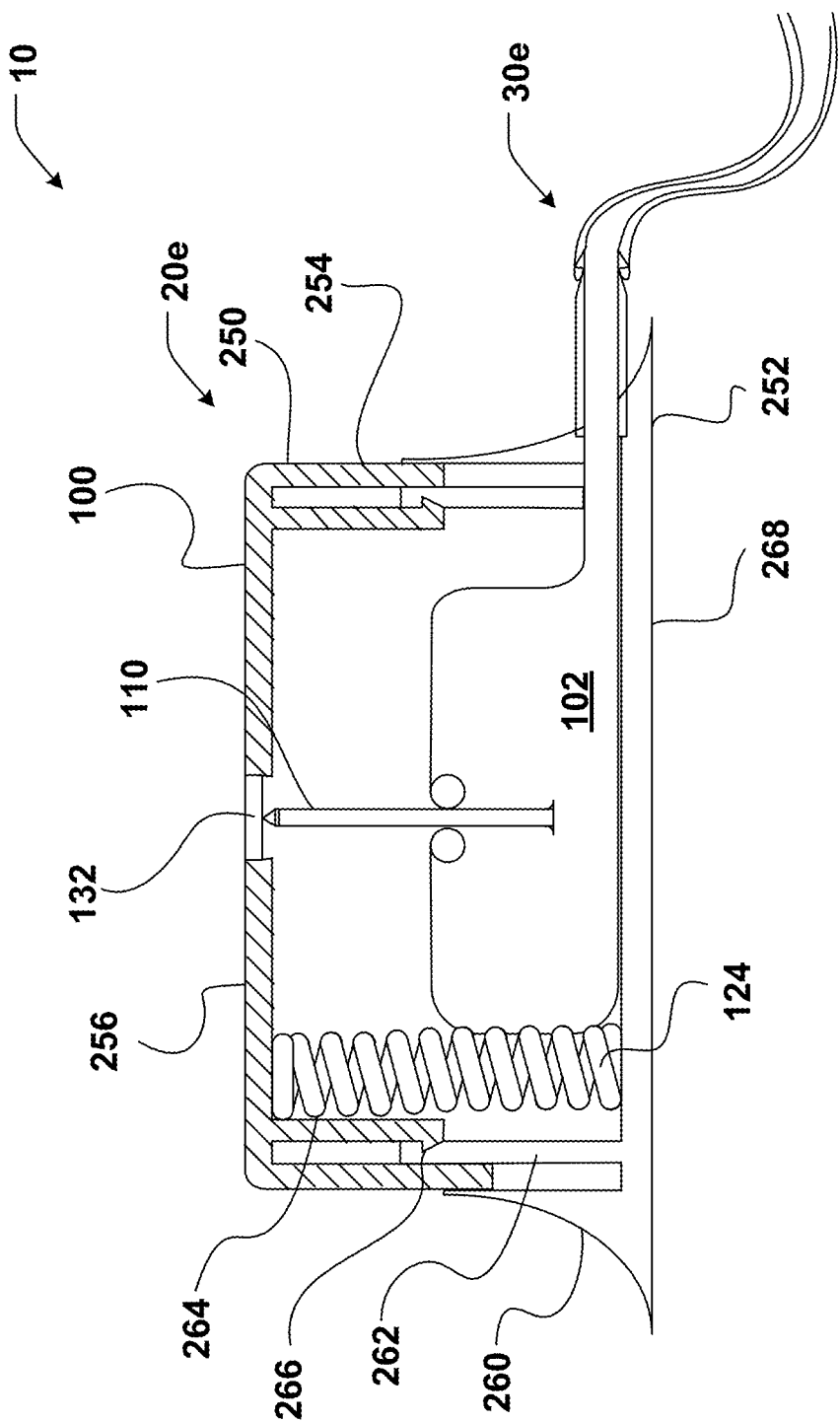
FIG. 6a illustrates a cross-sectional view of another embodiment of a medical device comprising an access port and a catheter according to the present disclosure, with a needle of the access port in a concealed position relative to the access port body.
Figure 6B:
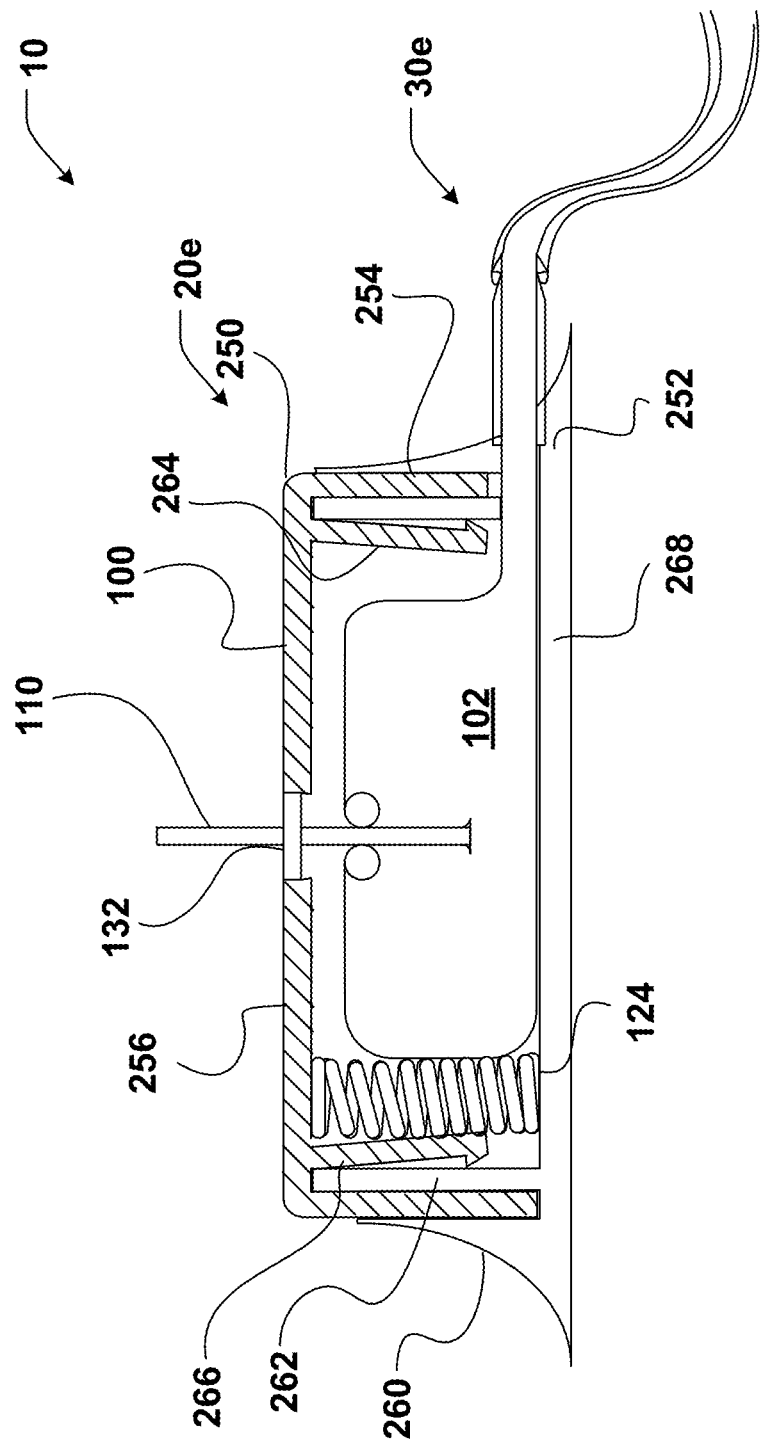
FIG. 6b illustrates a cross-sectional view of the embodiment of the medical device of FIG. 6a, with the needle of the access port in an exposed position relative to the access port body and the needle tip removed.

Referring now to FIGS. 6a and 6b, there is shown another embodiment of the medical device 10 of the present disclosure, which comprises access port 20e and catheter 30e. FIG. 6a shows the needle 110 of access port 20e in the concealed (retracted) position relative to access port body 100, and FIG. 6b shows the needle 110 of access port 20e in the exposed (extended) position relative to access port body 100.

As shown, at least a portion of the access port body 100 may move relative to the needle 110, such that the needle 110 may be fixed with regard to the chamber 102 but the self-closing seal 132 may move relative to the needle 110. The body 100 may therefore compress (collapse), exposing the needle 110 or decompress (expand) to cover and conceal the needle 110. In one embodiment, illustrated in FIG. 6a and FIG. 6b, the body 100 may include a first portion 250 and a second portion 252. More particularly, first portion 250 is provided by a first body member and second portion 252 is provided by a second body member.

To locate the first portion 250 of the body 100 relative to the second portion 252 of the body 100, the first portion 250 of the body 100 may include a first wall 254 extending from the upper main segment 256 of the first portion 250 of the body 100. In addition, the second portion 252 of the body 100 may include a second wall 260 and a support member 262. The first wall 254 may be received in a sliding manner between the second wall 260 and the support member 262.

The first portion 250 may also include one or more tabbed latches 264 also extending from the upper main segment 256 of the first portion 250 around the periphery of the body 100, which may hold the body 100 in a first decompressed (expanded) position as illustrated in FIG. 6a. The tabbed latch 264 may be received in a recess 266 provided by a support member 262 found in the second portion 252 of the body 100. When the access port body 100 is held in the first decompressed (expanded) position, the needle 110 may be completely or substantially contained within the access port body 100.

When compressed (collapsed), through the application of force on the body 100, the needle 110 which may be held in a fixed position relative to the second portion 252 of the body 100 may perforate and extend through the self-closing seal 132, as illustrated in FIG. 6b. In addition, the first wall 254 of the first portion 250 may slide towards the lower main segment 268 of the second portion 252 between the second wall 260 and the support member 262. The body 100 may be maintained in a collapsed positioned through continuous application of pressure. A spring 124 may also be provided which may raise the first portion 250 of the body 100 back to the first decompressed (expanded) position as illustrated in FIG. 6a.

A chamber 102 may be provided within the access port body 100 and mounted to or provided within, for example, the second portion of the body 252. In some embodiments, the needle 110 may be fixedly mounted to the chamber 102. While it is illustrated in FIGS. 6a and 6b that the needle 110 may extend into the chamber 102, the needle 110 may also be provided flush with the chamber 102. In some embodiments, the needle 110 may be integrated into the chamber 102 or access port body 100. Furthermore, in some embodiments, the needle 110 may include threads or another mechanical interlock allowing for the needle 110 to be removed from either the chamber 102 or access port body 100 for replacement.

Figure 7A:
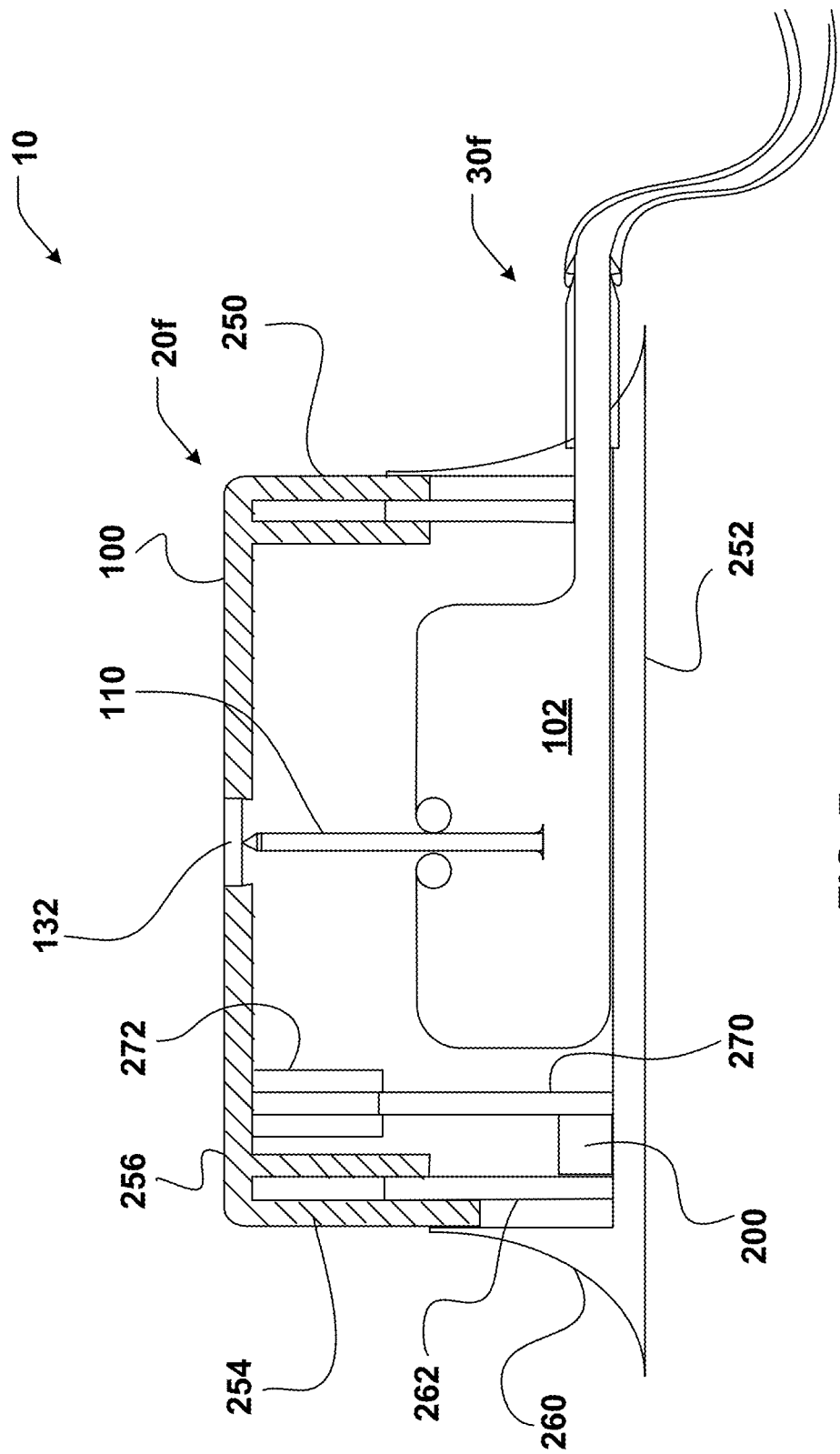
FIG. 7a illustrates a cross-sectional view of another embodiment of a medical device comprising an access port and a catheter according to the present disclosure, with a needle of the access port in a concealed position relative to the access port body.
Figure 7B:
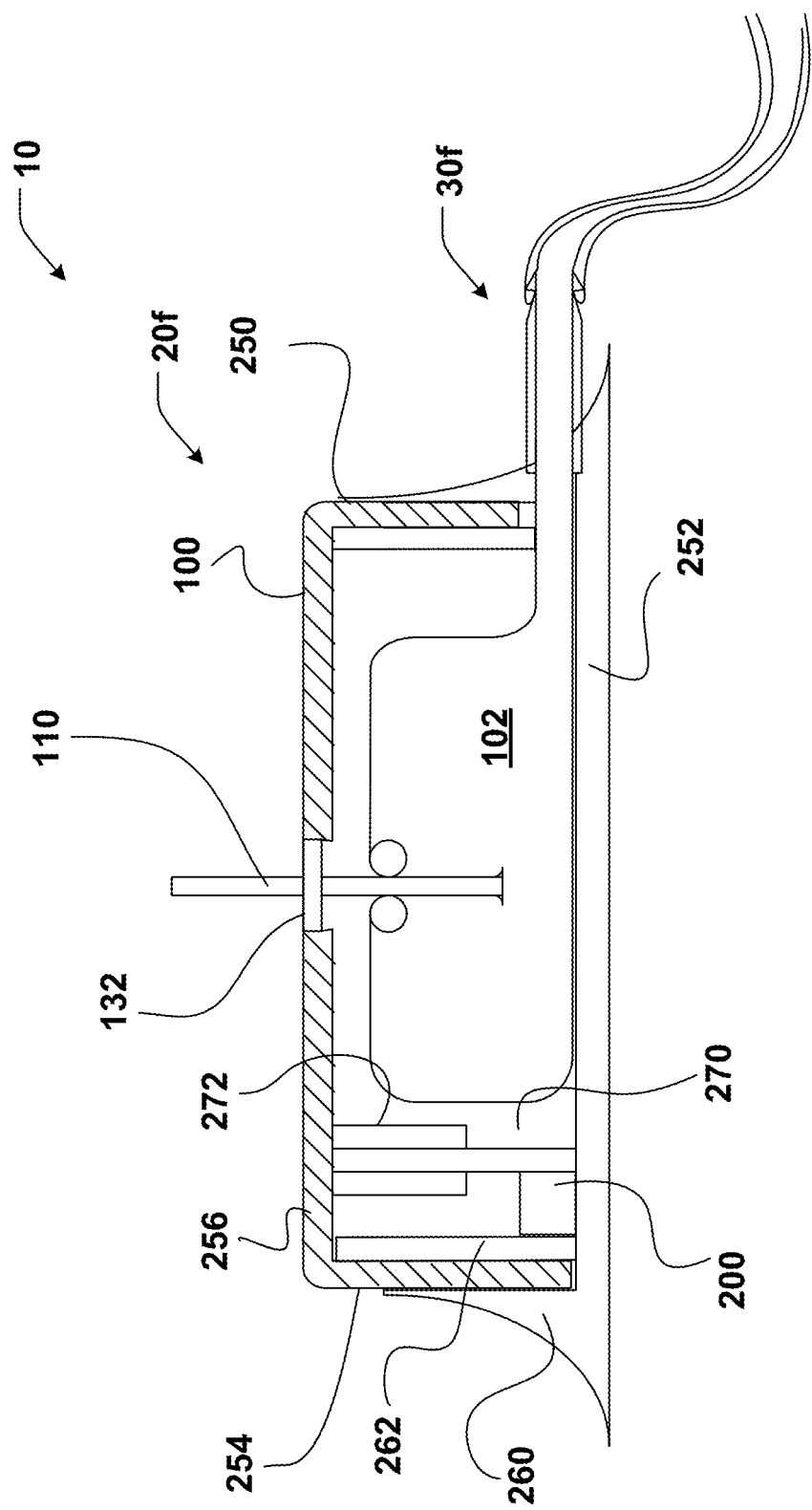
FIG. 7b illustrates a cross-sectional view of the embodiment of the medical device of FIG. 7a, with the needle of the access port in an exposed position relative to the access port body and the needle tip removed.

Referring now to FIGS. 7a and 7b, there is shown another embodiment of the medical device 10 of the present disclosure, which comprises access port 20f and catheter 30f. FIG. 7a shows the needle 110 of access port 20f in the concealed (retracted) position relative to access port body 100, and FIG. 7b shows the needle 110 of access port 20f in the exposed (extended) position relative to access port body 100.

As shown the first and second portions 250, 252 of the access port body 100 may be extended or retracted by an actuator that includes an electrical/mechanical device. The access port 20f may include a motor or other electrical device 200 that may decompress (expand) or compress (collapse) the body 100. In some examples, the motor 200 may include a piezoelectric micro-motor. The motor 200 may include a linear traveler 270, such as a shaft or a translator that may interact with a cylinder 272 provided in the body 100, moving the body halves 250, 252 relative to each other. It may be appreciated that the cylinder 272 need not be a tube having a complete wall, for example, slots may be provided in the wall. The linear traveler 270 may include, for example, a set of external threads, which may interact with a set of internal threads provided on the cylinder 272.

As the linear traveler rotates, the cylinder 272 and one of the portions, to which the cylinder 272 is mounted may move relative to the other portion. When linear traveler rotates in one direction, the body 100 may compress (collapse), wherein the needle 110 may pass through the self-closing seal 132 and may be exposed. When the traveler rotates in the other direction, the body 100 may decompress (expand), wherein the needle 110 may be pulled back through the self-closing seal 132 and covered. As illustrated, the motor 200 is mounted with the second portion 252 and the cylinder 272 to the first portion 250, but it may be appreciated that opposite situation where the motor 200 is mounted to the first portion 250 and the cylinder 272 is mounted to the second portion 252 may be provided as well. The motor 200 may be actuated by an actuator, such as a "button" or by another device, such as a wireless device as described above. Again, in one embodiment, to locate the first portion 250 of the body 100 relative to the second portion 252 of the body 100, the first portion 250 of the body 100 may include a first wall 254 extending from the upper main segment 256 of the first portion 250 of the body 100. In addition, the second portion 252 of the body 100 may include a second wall 260 and a support member 262. The first wall 254 may be received in a sliding manner between the second wall 260 and the support member 262.

Figure 8A:
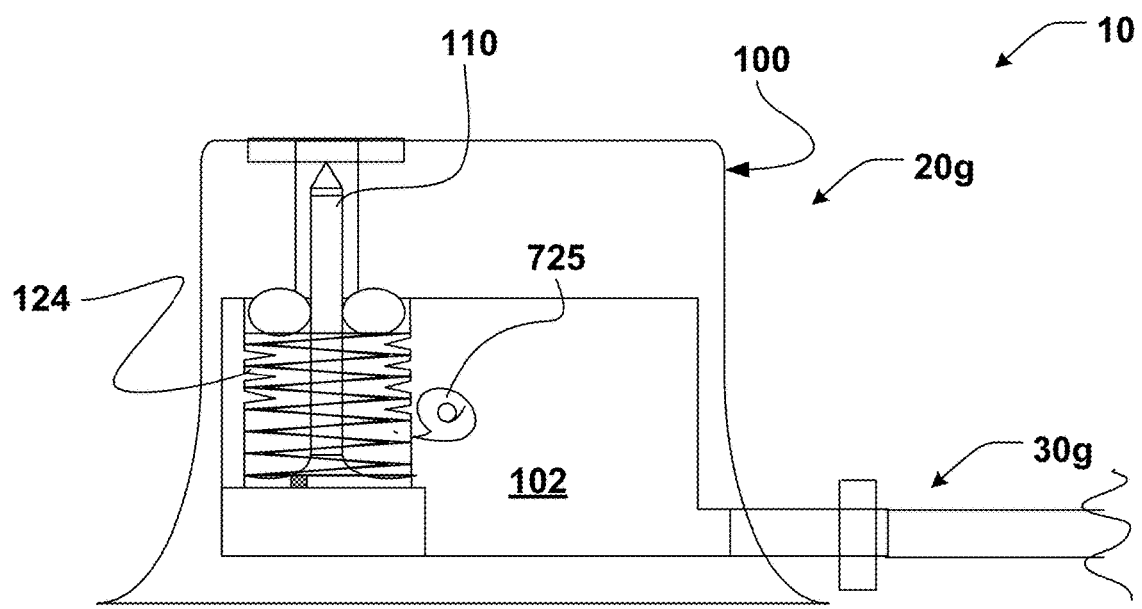
FIG. 8a illustrates a cross-sectional view of another embodiment of a medical device comprising an access port and a catheter according to the present disclosure with a needle of the access port in a concealed position relative to the access port body.
Figure 8B:
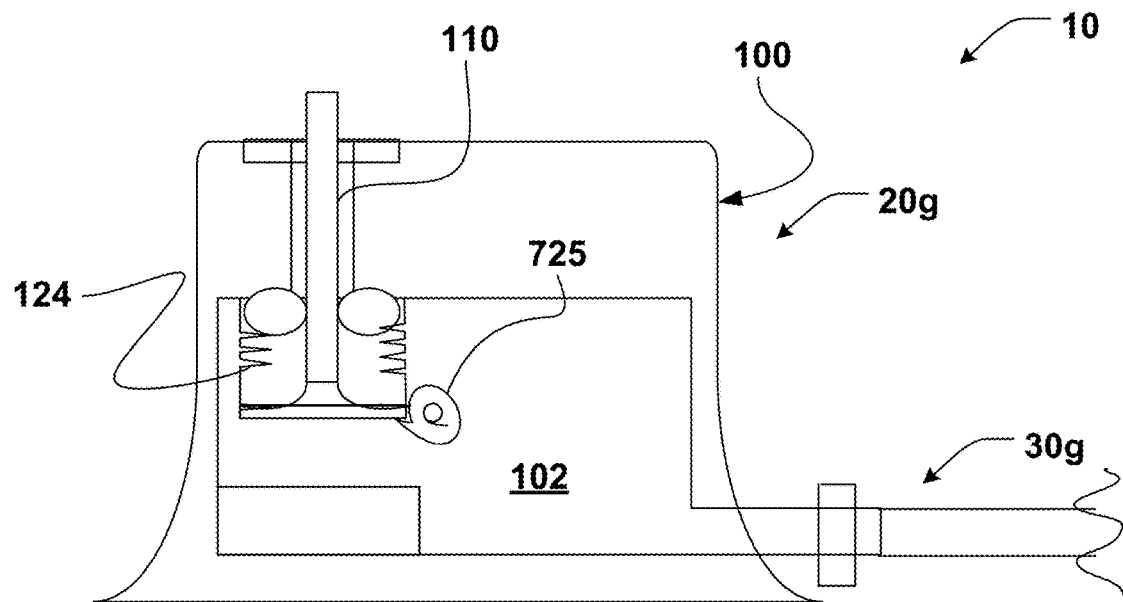
FIG. 8b illustrates a cross-sectional view of the embodiment of the medical device of FIG. 8a, with the needle of the access port in an exposed position relative to the access port body and the needle tip removed.

As noted earlier, the needle 110 may be positioned within the access port body 100 in a moving relationship to the chamber 102 or in a fixed relationship to the chamber 102. For example, in the embodiment illustrated in FIGS. 8a and 8b, a needle 110 may be provided in moving relationship to the chamber 102. The needle 110 may include a latching mechanism to keep the needle 110 from moving relative to the chamber 102 and may be activated by an actuator. Upon actuation, the needle 110 may be lifted out of the access port body 100 (such as by the action of a magnet) and retained in the open position by a spring loaded cam 125. The needle 110 may be held by a spring 124 in the closed or retracted position, keeping the needle 110 from slipping out of the access port. In other embodiments, such as illustrated in FIGS. 4a and 4b, the linear traveler provided in the motor 200 may include teeth or threads that may hold the needle 110 in place.

Referring now to FIGS. 9a-9i, there is shown another embodiment of a medical device 10 according to the present disclosure, which comprises implantable (subcutaneous), indwelling access port 20h and at least one implantable (subcutaneous), indwelling catheter 30h coupled to the access port 20h. More particularly, access port 20h is shown coupled with two catheters 30h.

As shown, the access port 20h includes at least one pointed, closed tip, hollow needle 110, and more particularly two needles 110 contained and housed within a chamber (cavity) 102 within access port body 100, with each one of the needles 110 in fluid communication with a catheter 30h, which may be part of a extracorporeal circuit. As shown in FIG. 9a, the needles 110 are in a concealed (retracted) concealed position relative to access port body 100, and each includes a pointed, removable tip 111 removably coupled to a distal end 114 of the needle shaft 112, which closes the distal end of shaft lumen 113. As shown in FIG. 9b, each needle 110 is in an exposed (extended) position relative to the access port body 100, and the removable tip 111 has been removed to expose lumen 113.

Similar to access port 20e, while each needle 110 of access port 20h may be stationary/fixed, at least a portion of the access port body 100, including the self-closing seal (e.g. self-healing septum) 132, may move relative to each needle 110. In order to expose each needle 110, also similar to access port 20e, access port body 100 may compress in response to a force applied to the access port body 100 from outside the host's body (above the skin). Alternatively, the access port body 100 may decompress and conceal each needle 110 in response to the force being removed.

Also similar to access port 20e, access port body 100 may comprise a first body member 250 and a second body member 252. However, rather than the first body member 250 and the second body member 252 sliding relative to one another to expose and conceal each of needles 110 as with access port 20e, compression and decompression of the access port body 100 is accomplished by elastically deforming an upper wall portion 251 of the first body member 250 along a length of each needle 110 towards the second body member 252. As such, first body member 250 may be formed of a flexible plastic elastomer.

As used herein, an elastomer may be characterized as a material that has an elongation at 23° C. of at least 100%, and which, after being stretched to twice its original length and being held at such for one minute, may recover in a range of 50% to 100% within one minute after release from the stress. More particularly, the elastomer may recover in a range of 75% to 100% within one minute after release from the stress, and even more particularly recover in a range of 90% to 100% within one minute after release from the stress.

The elastomer may be comprised of any polymer, including natural or synthetic polymers, and thermoplastic or thermoset polymers. Thus, the elastomer may be either a natural or synthetic elastomer. The elastomer may comprise, essentially consist of or consist of natural or synthetic rubber, which may include, acrylic rubber, butadiene rubber, butyl rubber, ethylene propylene rubber, ethylene propylene rubber diene monomer rubber, fluorocarbon rubber, isoprene rubber, nitrile rubber including hydrogenated nitrile rubber, polyurethane rubber, silicone rubber and styrene block copolymer (e.g. styrene butadiene rubber, styrene ethylene/butylene styrene rubber).

In addition, access port body 100 may include a spring 124, which may be located between the needles 110. When access port body 100 is compressed, through the application of force to the first body member 250 from outside the host's body (above the skin), with a force which is significant enough to overcome the bias force of spring 124, portion 251 of the first body member 250 deforms inward along a length of each needle 110 towards the second body member 252. Upon such compression, each needle 110 may extend through each self-closing seal 132 to be exposed from within access port body 100, and spring 124 will compress. When access port body 100 is decompressed, through the removal of the force to the first body member 250 from outside the host's body, the bias (decompression) force of the spring 124 will force portion 251 of the first body member 250 to deform outward along a length of each needle 110 away from the second body member 252. Upon such decompression, each needle 110 may retract through each self-closing seal 132 to be concealed within the access port body 100, and spring 124 will decompress.

With the dual needle and catheter arrangement of access port 20h, the access port 20h may be used for hemodialysis, with one needle 110/catheter 30h coupled (in fluid communication) between an artery of the host and a dialyzer, and the other needle 110/catheter 30h coupled (in fluid communication) between a vein of the host and a dialyzer.

After a fluid infusion treatment and/or a fluid extraction treatment, any of the access ports and catheters disclosed herein, collectively access port 20 and catheter 30, may be flushed with saline and locked with an antimicrobial and/or an anticoagulant locking fluid, which may be referred to as a catheter lock, to inhibit development of clots and microorganisms within the port 20 or the catheter 30.

For the purposes of the present disclosure, the process of "locking" should be understood as filling the access port 20 and/or catheter 30 with a locking fluid that is an anticoagulant and/or an antimicrobial, followed by retaining the locking fluid in the access port 20 and/or catheter 30 until the access port 20 and/or catheter 30 is used again for a fluid infusion treatment and/or a fluid extraction treatment, at which time the locking fluid may be withdrawn from the access port 20 and/or catheter 30, such as with a syringe. The access port 20 and/or catheter 30 should be locked with a volume of locking fluid which approximates the internal volume of the access port passage and the catheter lumen. The locking fluid may be constrained in the lumen 145 of catheter 30*h* by a valve 290 (e.g. one-way or two-way) located at the distal end of the catheter 30*h* (see FIG. 9*g*). The valve 290 may also prevent introduction of air into the blood stream of the patient and a subsequent air embolism. While the valve 290 may be shown located in the catheter 30*h*, the valve may be located in the access port 20*h*, particularly within one or both of needles 110, or any other portion of the flow passage.

Examples of antimicrobial compositions include taurolidine and/or taurinamide and taurinamide derivatives.

Examples of anticoagulant compositions include heparin, citrate salts, citric acid, ethylenediaminetetraacetic (EDTA) acid, enoxaparin sodium, coumarin, indanedione derivative, anisindione, warfarin protamine sulfate, streptokinase and urokinase)

The locking fluid may be a Newtonian fluid or a non-Newtonian fluid, and may further be a gel, such as a thixotropic gel and more particularly a hydrogel.

Accordingly, a method of injecting a fluid (liquid) composition into a host may be provided using the access port described herein. As alluded to above, a composition may include pharmaceutical products, therapeutic drugs, bodily fluid, nutrients, contrasting agents, dialysis fluid and other fluids. Furthermore, a host (e.g. patent or other subject) may include any vertebrate or invertebrate, including humans, other mammals, ayes, reptiles, etc. An access port may be implanted into the host and the catheter may be inserted into a vein. The needle may be exposed (extended) from the port upon actuation and may puncture the skin. A composition may be introduced to the host by either injecting the composition into the needle or otherwise introducing the needle into a container, such as through a vial stopper. Once administration of the composition is finished, the needle may be concealed (retracted) or otherwise positioned back through the skin and into the port.

In another example of a method of delivering a composition utilizing a vascular access port contemplated herein, a receiver may receive or otherwise detect a first electromagnetic indicator from a transmitter, such as an actuator. The indictor may be processed by the receiver to provide an electrical signal to a processor in electrical communication with the receiver. A motor may be activated by the processor once it receives a signal to activate the motor and the motor may extend or retract the needle with respect to the body of the vascular access port or the motor may collapse or expand the vascular access port with respect to the needle.

In addition, as may be appreciated herein, the actuator may be provided in direct or indirect communication with the needle and is configured to either move the needle relative to the access port body or move the access port body relative to the needle. Communication may be electrical and/or mechanical, such as that provided by magnetic fields, electrical signals, mechanical linkages or forces, provided by levers, springs, etc. Furthermore, in instances where the body may move relative to the needle, communication may be considered indirect. It may also be appreciated that the actuator may be located outside of the housing body, located at least partially within the housing body or located completely within the housing body.

In other embodiments of the present disclosure, an indwelling access port 20, such as indwelling access port 20*h*, disclosed herein may also be used during a hemodialysis and/or hemofiltration procedure. As shown in FIG. 9*c*, each of needles 110 may be coupled to fluid infusion and/or extraction apparatus 42 (which may be understood to be part of medical device 10), such as a dialysis apparatus 45, by hollow tubular fluid infusion and/or extraction member 47, such as a cylindrical tubing segment. As shown, the shaft 112 of each needle 110 may be configured to mate with tubular fluid infusion and/or extraction member 47, particularly with the outer diameter of the shaft 112 approximating the inner diameter of the lumen 48 of the tubular fluid infusion and/or extraction member 47. With the extracorporeal circuit as shown, extracorporeal separation of blood may be performed by blood flowing from the host 58 through indwelling catheter 30*h*, needle 110, and tubular fluid infusion and/or extraction member 47 and into to fluid infusion and/or extraction apparatus 42 where it is treated, particularly by removing waste products such as creatinine, urea and free water from the blood. Thereafter, the cleaned blood is returned to the host 58 by flowing through the other tubular fluid infusion and/or extraction member 47, the other needle 110 and indwelling catheter 30*h*. Blood flow in either direction may be assisted by pump 46 of the fluid infusion and/or extraction apparatus 45.

Medical device 10, including indwelling access port 20, may comprise a closed system (drug) transfer device. A closed system (drug) transfer device may be understood as a (drug) transfer device that inhibits a transfer of environmental contaminants into a system and an escape of hazardous drug or vapor concentrations outside the system.

Referring now to FIGS. 9*d*-9*f*, in certain embodiments of indwelling access port 20, such as indwelling access port 20*h*, the distal end portion 114 of each lumen 113 of each needle 110 may include a self-closing seal 280 such as a "self healing" silicone septum, which may be accessed upon removal of the needle tip 114. Similar to the prior embodiment, each of needles 110 may be coupled to fluid infusion and/or extraction apparatus 42 (which may be understood to be part of medical device 10), such as a dialysis apparatus 45, by tubular fluid infusion and/or extraction member 47. As shown, the shaft 112 of each needle 110 may be configured to mate with tubular fluid infusion and/or extraction member 47, particularly with the outer diameter of the shaft 112 approximating the inner diameter of the lumen 48 of the hollow tubing 47.

As shown, a distal end portion of each lumen 48 of each tubular fluid infusion and/or extraction member 47 may include a self-closing seal 49 such as a "self healing" silicone septum. Furthermore, each lumen 48 may contain a pointed tip (hypodermic) needle 50 for delivery of fluid from fluid source 43 to host 58 and/or extraction of fluid from host 58 to fluid receptacle 44.

During operation, the distal end portion 114 of needle shaft 112 is received into the distal end portion of lumen 48 of tubular fluid infusion and/or extraction member 47 such that a seal is formed between self closing seals 280 and 49. In the foregoing manner, a closed system transfer device is formed between access port 20*h* and fluid infusion and/or extraction apparatus 42.

As shown in FIG. 9*f*, pointed open tip hollow needles 50 may be extended through self-closing seals 280 and 49 after the two self-closing seals 280 and 49 have made contact with each other to form an extracorporeal circuit.

In certain embodiments, it may become desirable to clean indwelling catheter 30, such as indwelling catheter 30*h* to remove a build-up (e.g. of coagulum, fibrin or other biological materials). Referring now to FIGS. 9*g*-9*i*, there is shown fluid infusion and/or extraction apparatus 42 may further comprise a cleaning apparatus 74. Cleaning apparatus 74 may comprise a multi-lumen catheter 75 which comprises a catheter body 76, having a fluid infusion lumen 77*a*, a fluid extraction lumen 77*b* and a centrally disposed drive lumen 77c which contains a cylindrical flexible rotatable drive shaft 78 to rotate cleaning head 79.

During operation, rotating drive 80 of cleaning apparatus 74 may rotate flexible drive shaft 78 which in turn rotates cleaning head 79, which may comprise a brush. Cleaning head 79 may then remove biological materials from the inside of lumen 145 of catheter body 144 by rotating against the inner surface 147 of catheter body 144 which defines lumen 145. Cleaning head may also be used to clean the lumen 113 of needle 110 of access port 20h, as well as any other portion of the fluid flow passage.

Before, during or after use of cleaning head 79, fluid from fluid source 43 may flow through fluid infusion lumen 77a and into lumen 145 of catheter 30h to flush the cleaning site. The fluid may be delivered with the aid of pump 46, which may comprise a peristaltic pump.

The fluid may be constrained in the lumen 145 of catheter 30h by a valve 148 located at the distal end of the catheter 30h, such as a one-way valve (e.g. duckbill valve) or a two-way valve. The valve 148 may also prevent introduction of air into the blood stream of the patient and a subsequent air embolism.

The fluid may be extracted from the lumen 145 of catheter 30h through fluid extraction lumen 77b to fluid receptacle 44. Fluid extraction may take place simultaneous with fluid delivery, or after fluid delivery has stopped, or intermittently alternating between repeated fluid delivery and repeated fluid extraction. Fluid extraction may be assisted by pump 46 and/or a vacuum 52 and/or gravity.

The fluid used for cleaning access port 20h and catheter 30h may be normal (physiologic) saline. Also, it should be understood that the method of infusing the fluid passage of access port 20h and catheter 30h with fluid via catheter 75, as well as extracting fluid from the fluid passage of access port 20h and catheter 30h with catheter 75, may be similarly used to infuse and extract the locking fluid from the access port 20h and catheter 30h.

Referring now to FIGS. 10a-10f, there is shown another embodiment of a medical device 10 according to the present disclosure, which comprises implantable (subcutaneous), indwelling access port 20i and at least one implantable (subcutaneous), indwelling catheter 30i coupled to the access port 20i. More particularly, access port 20i is shown coupled with two catheters 30i.

Similar to the prior embodiment, medical device 10, including indwelling access port 20i, may comprise a closed system (drug) transfer device. However, in contrast to the prior embodiment, the closed system of the present embodiment is created in a different manner.

With the prior embodiment of FIGS. 9d-9f, fluid infusion and/or extraction apparatus 42 is coupled with the needles 110 after the needles 110 have pierced through tissue 60. Moreover, the removable needle tips 111 are also removed before fluid infusion and/or extraction apparatus 42 is coupled with the needles 110. Such may be accomplished, at least in part, by the presence of self-closing seals 280 within the needles 110. However, in the present embodiment, self-closing seals 280 have been eliminated.

Referring now to FIG. 10a, in order to provide a closed system, fluid infusion and/or extraction apparatus 42 comprises an elongated tubular (cylindrical) housing member 51. At the end of the tubular housing is located a round disc shaped self-closing seal (e.g. self-healing septum) 53.

Within tubular housing member 51 are located needle tip holders 54, which are configured to removably hold the needle tips 111 during an installation of the needle tips 111 on the needle shafts 112, or removal of the needle tips 111 from the needle shafts 112, particularly when the screw threads of the needle shafts 112 and screw threads of needle tips 111 are disengaged during installation or removal of needle tips 111. In at least one embodiment, the needle tip holders 54 may be located at the distal end of needle tip (tubular) support members 56.

Needle tip holders 54 may comprise needle tip receptacles 54a, which be configured to hold needle tips 111 within a mating portion 54b thereof in a variety of ways. In at least one embodiment, at least a portion of the needle tip holders 54, and more particularly the mating portions 54b of the needle tip receptacles 54a, may form a friction fit (which also may be known as an interference fit or pressure grip fit) connection with the needle tips 111. A friction fit connection may be understood herein as a connection formed between two components which solely relies upon friction to inhibit separation of the components, for example by one of the components being pressed into the other component such that at least one of the components is compressed (deformed) against one another.

In order to provide a friction fit connection, a portion of the needle tip receptacles 54a, and more particularly the mating portions 54b, may be formed with a smaller dimension than the mating portion of the needle tips 111 to form the friction fit connection. In such instance, needle tip holders 54, and more particularly the mating portions 54b of needle tip receptacles 54a may be formed of an elastically compressible/deformable material, such as rubber, which may deform (as to enlarge) when the needle tips 111 are located therein to hold the needle tips 111.

Alternatively, or in combination with a friction fit connection, the needle tip holders 54 may retain needle tips 111 with a positive mechanical connection. A positive mechanical engagement connection may be understood herein as a connection formed between the components which does not rely solely on friction to inhibit separation of the components and which includes a mechanical interlock to inhibit separation of the components (e.g. overlapping surfaces).

In such instance, needle tip holders 54 may again be formed of an elastically compressible/deformable material, such as rubber. In addition, a distal end of the needle tip holders 54 may be provided with an elastically compressible/deformable annular ring 54c, which deforms outward when needle tips 111 are being inserted into and removed from needle tip receptacles 54a. The positive mechanical connection may be formed when the needle tips 111 are fully seated in the needle tip receptacles 54a and the elastically compressible/deformable annular rings 54c may return to their initial (pre-deformation) orientation, which mechanically holds the needle tips 111 in the needle tip receptacles 54a.

Alternatively, or in combination with at least one or both of the above, needle tip holders 54 may be formed of a material which is porous to vacuum drawn through the lumens of needle tip holder (tubular) support members 56 from vacuum 52 such that the needle tips 111 may be removably retained in the needle tip holders 54 by vacuum force.

Alternatively, or in combination of at least one or all of the above, needle tip holders 54 may be formed of a material which is magnetic such that the needle tips 111, which may be made of a ferromagnetic material, may be removably retained in the needle tip holders 54 by magnetic force.

As set forth herein, needle tips 111 and needle shafts 112 may be joined by threaded engagement. In order to help facilitate engagement and disengagement of the threads, needle tip holder (tubular) support members 56 form part of a rotational driver which may rotate the needle tip holder (tubular) support members 56/tip holders 54 in a clockwise or counter-clockwise direction which, when coupled to needle tips 111, may correspondingly rotate the needle tips 111 to install or remove the needle tips 111, respectively.

Moreover, as best shown in FIGS. 10*a* and 10*c*, the internal sidewall of the mating portions 54*b* of the needle tip receptacles 54*a* and the external sidewall of mating portion 111*b* of the needle tips 911 may each comprise a plurality of planar mating sections 54*d* and 111*d*, respectively. The plurality of the planar sections 111*d* of the mating portion 111*b* of the needle tips 911 may be arranged around a periphery of mating portion 111*b* to form a polygonal shape. As shown, the plurality of the planar sections 111*d* of the mating portion 111*b* of the needle tips 111 may more particularly form a six-sided (male) polygon, i.e. a hexagon. Similarly, the plurality of the planar sections 54*d* of the mating portion 54*b* of the needle tip receptacles 54*a* may more particularly form a six-sided (female) polygon, i.e. hexagon, which may also be referred to as a socket.

Once the needle tip holders 54 couple with the needle tips 111, the rotational driver for each needle tip holder (tubular) support members 56/tip holders 54 may be rotated counter-clockwise to remove needle tips 111 from shafts 112. As shown in FIG. 10*d*, once the needle tips 111 disengage from the shafts 112, the needle tip holder (tubular) support members 56/tip holders 54 may be retracted away from the shaft 112.

At this time, as shown by FIGS. 10*b*, the two needle tip holder (tubular) support members 56/tip holders 54 and the two tubular fluid infusion and/or extraction members 47 may be rotated approximately 90 degrees (e.g. clockwise) such that the two tubular fluid infusion and/or extraction members 47 are aligned with the needle shafts 112 as shown in FIGS. 10*e* and 10*f*. As shown by FIG. 10*g*, the two tubular fluid infusion and/or extraction members 47 may then be extended such that the two needles 110 pass or extend through self-closing seals 49 and into lumens 48 of the tubular fluid infusion and/or extraction members 47 to form an extracorporeal circuit.

Once fluid infusion and/or extraction is complete, the two tubular fluid infusion and/or extraction members 47 may then be retracted. As shown by FIG. 10*f*, the two needle tip holder (tubular) support members 56/tip holders 54 and the two tubular fluid infusion and/or extraction members 47 may be rotated approximately 90 degrees (e.g. counter-clockwise) such that the two needle tip holder (tubular) support members 56/tip holders 54 are realigned with the needle shafts 912 as shown in FIG. 10*c*. The two needle tip holder (tubular) support members 56/tip holders 54 may then be extended as shown in FIG. 10*c*. The rotational driver for each needle tip holder (tubular) support members 56/tip holders 54 may be rotated clockwise to engage the screw threads and install needle tips 111 to shafts 112. Thereafter, the two needle tip holder (tubular) support members 56/tip holders 54 may be retracted, and the fluid infusion and/or extraction apparatus 42 may be subsequently removed.

Referring now to FIGS. 11*a*-11*d*, there is shown another embodiment of a medical device 10 according to the present disclosure, which comprises implantable (subcutaneous), indwelling access port 20*j* and at least one implantable (subcutaneous), indwelling catheter 30*j* coupled to the access port 20*j*. More particularly, access port 20*j* is shown coupled with two catheters 30*j*.

Similar to the prior embodiments, medical device 10, including indwelling access port 20*j*, may comprise a closed system (drug) transfer device. However, in contrast to the prior embodiments, the closed system of the present embodiment is created in a different manner, particularly with needles 110 have a pointed open tip 111 rather than a pointed closed tip. Further, since the pointed open tip is formed unitary (as one piece) with the needle shaft 112. As such the needle tip 111 is permanent and not removable.

Referring now to FIGS. 11*e* and 11*d*, fluid infusion and/or extraction apparatus 42 comprises an outer tubular housing member 51 which contains hollow tubing 47. As shown, similar to the prior embodiment, a distal end portion of each lumen 48 of each hollow tubing 47 may include a self-closing seal 49 such as a "self healing" silicone septum. Furthermore, The distal end of tubular housing member 51 includes an annular sealing element 53.

As shown in FIG. 11*e*, prior to extension of needles 110 through the tissue (skin) surface 62, annular sealing element 53 seals against the skin surface to provide a closed system, a system in which environmental contaminants are inhibited from entering the system and hazardous drug or vapor concentrations are inhibited from escaping from the system.

As shown in FIG. 11*d*, when fluid infusion and/or extraction apparatus 42 is pushed down on tissue 60, the surface 62 of tissue 60 deforms inward and the elastically deforming a portion 251 of the first body member 250 is compressed such that needles 110 extend through the tissue (skin) surface 62, penetrate self-closing seals 49, and enter lumens 48 of each hollow tubing 47 to form an extracorporeal circuit.

Referring now to FIGS. 12*a*-12*b*, there is shown another embodiment of a medical device 10 according to the present disclosure, which comprises implantable (subcutaneous), indwelling access port 20*k*. While an indwelling catheter may be coupled to the indwelling access port 20*k* in a manner similar to prior embodiments, the catheter is not shown.

Similar to prior embodiments, medical device 10 including indwelling access port 20*k*, may comprise a closed system (drug) transfer device. However, in contrast to the prior embodiments, the closed system of the present embodiment is created in a different manner, particularly with indwelling access port 20*k* only having a single needle 110.

Fluid infusion and/or extraction apparatus 42 comprises a multi-port housing 82 having a first port 83, a second port 84 and a third port 85. First port 83 may be referred to as a fluid infusion and/or fluid extraction port, while the second port 84 may be referred to as a needle tip removal and/or installation port, and the third port 85 may be referred to as a needle holding port. All three ports 83, 84, 85 are in fluid communication via the segments of a Y-shaped (tubular) passage 85 within the housing 82.

During operation, needle 110 is received by needle holding port 85 and into passage 86. Multi-port housing 82 may include a self-closing seal 49 which seals against the shaft 112 of needle 110. Multi-port housing 82 may further comprises stabilizing ring 87, particularly in the form of an annular ring, which surrounds the needle holding port 85, and configured to overlie and rest on the surface 62 of tissue 60. Stabilizing ring 87 may be surrounded by a rotatable collar 88 which co-operates with the stabilizing ring 87 to clamp down on the needle shaft 112 in a known manner, particularly by rotating clockwise to grasp the needle shaft 112 and rotating counter-clockwise to release the needle shaft 112.

Needle tip 111 may be removed from the needle shaft 112 by extending first needle tip holder support member 56 from needle tip removal and/or installation port 84 within passage 86 towards the needle tip 111 such that needle tip holder 54 couples with the needle tip 111. Once needle tip holder 54 couples with the needle tip 111, the needle tip 111 may be removed from the needle shaft 112 in a manner as previously described (e.g. counter-clockwise rotation, pulling force, etc.). Once the needle tip 111 disengages from the shaft 112, the needle tip holder support member 56/tip holder 54 may be retracted away from the shaft 112 and back to the entrance of the needle tip removal and/or installation port 84 as shown in FIG. 12b.

Thereafter, once needle lumen 113 is exposed, a treatment fluid may be delivered from fluid source 43 (e.g. drug delivery for a chemotherapy procedure) coupled to fluid infusion and/or fluid extraction port 83 and/or extracted from host 58 to fluid receptacle 44 (e.g. phlebotomy procedure) coupled to fluid infusion and/or fluid extraction port 83. As shown, fluid source 43 may be a syringe, or an intravenous (IV) bag.

After a fluid infusion treatment and/or a fluid extraction treatment, access port 20k and catheter 30, may be flushed with saline and locked with an antimicrobial and/or an anticoagulant locking fluid, which may be referred to as a catheter lock, to inhibit development of clots and microorganisms within the port 20k or the catheter 30.

Thereafter, the first (original) needle tip 111 may be replaced by once again extending first needle tip holder support member 56 from needle tip removal and/or installation port 84 within passage 86 towards the needle tip 111. The needle tip 111 may then engage with the needle shaft 112 in a manner as previously described (e.g. clockwise rotation, pushing force, etc.). Once the needle tip 111 engages with the shaft 112, the needle tip holder support member 56/tip holder 54 may be retracted away from the shaft 112 and back to the entrance of the needle tip removal and/or installation port 84 as shown in FIG. 12b.

Alternatively, rather than reinstalling the original needle tip 111, a new sterilized needle tip 111 may be installed on needle shaft 112. As shown, multi-port housing 82 may further comprise a second needle tip holder 54 to hold the new sterilized needle tip 111. In order to align the new sterilized needle tip 111 with needle tip removal and/or installation port 84, the needle tip holders 54 for both needle tips 111, original and new, may be retained on a circular rotatable positioning member 90 disposed in a circular recess 91 of a platform member 92 which overlies the needle tip removal and/or installation port 84. The needle tip holder 54 containing the new needle tip 111 may then be rotated on the circular rotatable positioning member 90 disposed in the circular recess 91 of the platform member 92 in the approximately 180 degrees such that the original (used) needle tip 111 switches position with the new, sterilized needle tip 111 and the new, sterilized needle tip 111 is now aligned with the needle tip removal and/or installation port 84. The second needle tip holders 54 may then be operated in the same manner as the first needle tip holder 54 to engage the needle tip 111 with the needle shaft 112.

In other embodiments of the present disclosure, an indwelling access port 20, such as indwelling access port 20a, disclosed herein may also be used during a chemotherapy procedure. During a chemotherapy procedure, fluid source 32 may comprise one or more chemotherapeutic agents which are administered through the indwelling access port 20a to the host 58, with the aid of pump 46.

In other embodiments of the present disclosure, the indwelling access ports 20 and indwelling catheters 30 disclosed herein may also be used during an apheresis procedure. Apheresis may generally be understood as procedure in which blood of a host (e.g. patient, donor) is removed from the host, passed through an apheresis apparatus with separates out at least one component from the blood and then returns the remainder of the blood to the circulation of the host. An access port with one needle or two needles may be utilized depending on the type of apheresis procedure. For example, an access port with two needles (e.g. 20h) may be suitable for an apheresis procedure which makes use of continuous flow centrifugation (CFC), which ordinarily requires two venipunctures provided by two separate needles. As such, rather than the two needles each being directly inserted into a venous blood vessel, the distal ends of two indwelling catheters coupled to the indwelling access port, and more particularly needle as shown in FIGS. 9a and 9b, may each be inserted directly into a venous blood vessel.

Continuous flow centrifugation (CFC) may be understood to involved simultaneously collecting the blood from the host, spinning/processing the blood in a centrifuge to separate the components of the blood and remove one or more components from the blood and returning the unused component of the blood to the host without the component(s) which have been removed.

Alternatively, an access port with one needle may be suitable for an apheresis procedure which makes use of intermittent flow centrifugation (IFC), which ordinarily requires one venipuncture. In contrast to continuous flow centrifugation (CFC), intermittent flow centrifugation (IFC) works in cycles, i.e. collecting blood from the host, spinning/processing the blood in a centrifuge to separate the components of the blood and remove one or more components from the blood, and then returning the unused components of the blood to the host without the component(s) which have been removed in a bolus.

The apheresis may more particularly comprise plasmapheresis (separation and removal of plasma from blood); erythrocytapheresis (for separation and removal of erythrocytes (red blood cells) from blood); plateletpheresis (for separation and removal of blood platelets, while returning red blood cells (RBCs), white blood cells (WBCs), and plasma); and leukapheresis (for separation and removal of leukocytes (white blood cells) from blood, such as neutrophil granulocytes, eosinophil granulocytes, basophil granulocytes, lymphocytes (natural killer cells, T-cells and B-cells) and monocytes.

In other embodiments of the present disclosure, an indwelling access port 20, such as indwelling access port 20a, disclosed herein may also be used with the catheter 30a during a parenteral nutrition procedure, and more particularly a total parenteral nutrition procedure. Parenteral nutrition may be understood as feeding the host 58 intravenously, and in doing so bypassing the usual processes of eating and digestion. Parenteral nutrition may be divided into central parenteral nutrition (CPN) and peripheral parenteral nutrition (PPN). Such may also be referred to as central venous nutrition (CVN) and peripheral venous nutrition (PVN). Central parenteral nutrition (CPN), or as central venous nutrition (CVN) is administered through primary veins such as the subclavian vain, jugular vein and femoral veins. Peripheral parenteral nutrition (PPN), or peripheral venous nutrition (PVN) is administered through secondary (peripheral) veins in the arm. Such may be further referred to as total parenteral nutrition, either when no significant nutrition is obtained by the host 58 through other routes. During a parenteral nutrition procedure, fluid source 32 may comprise a nutritional formulae that contain nutrients such as glucose, amino acids, lipids and added vitamins and dietary minerals to be administered to the host 58 through the indwelling access port 20a to the host 58, with the aid of pump 46.

Parenteral nutrition may be required for a host 58 who do not have a functioning gastrointestinal tract, or who have disorders requiring complete bowel rest, including bowel obstruction, short bowel syndrome, gastroschisis, prolonged diarrhea, fistula, Crohn's disease and ulcerative colitis, as well as certain pediatric GI disorders including congenital GI anomalies and necrotizing enterocolitis. Parenteral nutrition may also be required for hosts who may not be able to feed themselves, such as hosts who may be in a coma In other embodiments of the present disclosure, an indwelling access port 20, such as indwelling access port 20a, disclosed herein may also be used with the catheter 30a being inserted into a body cavity 70 other than the peritoneal cavity. For example, an indwelling access port 20, such as indwelling access port 20a, disclosed herein may also be used with the catheter 30a being inserted into the stomach for long-term enteral nutrition, with the catheter 30a operating as a gastric feeding tube (G-tube). Catheter 30a may also be inserted into the jejunum and thus operate as a jejunal feeding tube (J-tube), or be inserted into both the stomach and jejunum and thus operate as a gastrojejunal feeding tube (GJ-tube).

In other embodiments of the present disclosure, an indwelling access port 20, such as indwelling access port 20a, disclosed herein may also be used during infusion of other cancer treatments (i.e. other than chemotherapy). For example an indwelling access port 20, such as indwelling access port 20a, disclosed herein may also be used with the catheter 30a during a CAR-T treatment. This immunotherapy uses the hosts's own T cells to specifically attack cancer. The T cells are collected from the host's blood using apheresis, then genetically engineered to produce special receptors on their surface known as chimeric antigen receptors or "CARs". CAR proteins allow T cells to recognize a specific antigen on cancer cells.

The engineered CAR-T cells are grown in the laboratory until they number in the billions, then infused into the patient. The T cells multiply in the patient's body and, with guidance from their engineered receptors, recognize and kill cancer cells that harbor the antigen on their surfaces.

However, reintroduction of CAR-T cells is problematic using small gauge needles (e.g. 20-21 gauge). Reinfusion using small gauge needles can damage or kill (lyse) up to 50% of the re-injected CAR-T cells. This cellular destruction is caused simply by pushing too many cells through the small gauge needles, particularly in targeted tumor or brain applications. As a result, indwelling access port 20, such as indwelling access port 20a may make use of larger gauge needles (e.g. 14-17 gauge) to re-infuse cells through a large bore, alleviating cell destruction (which may be understood as lysis occurring due to mechanical pressure disruption of cell membranes cause by external pressure applied thereto). Stated another way, the use of small gauge needles may reduce the shear rate/pressure placed on the CAR-T cells during introduction, thus reducing the level of cellular destruction.

In other embodiments of the present disclosure, an indwelling access port 20, such as indwelling access port 20a, disclosed herein may also be used with the catheter 30a being inserted to blood vessel 68 to treat hemochromatosis. Hemochromatosis, or iron overload, indicates accumulation of iron in the body from any cause. In order to treat hemochromatosis, blood may be removed from the host via phlebotomy.

An indwelling access port 20, such as indwelling access port 20a, disclosed herein may also be used with the catheter 30a being inserted to blood vessel 68 to deliver blood to the body. For example, indwelling access port 20a, disclosed herein may also be used with the catheter 30a being inserted to blood vessel 68 to treat sickle cell (anemia) disease. Sickle cell disease changes normal, round red blood cells into cells that can be shaped like crescent moons, a shape which is associated with the crescent-shaped blade of a sickle. In order to treat sickle cell disease, blood may be delivered to the host via transfusion. A blood transfusion lowers the amount of hemoglobin S red blood cells in the body. When there are fewer sickled hemoglobin S cells in the bloodstream, they are less likely to build up and block blood vessels. The transfusion my also take place immediately after a phlebotomy to remove blood and sickle shaped red blood cells from the host.

An indwelling access port 20, such as indwelling access port 20a, disclosed herein may also be used with the catheter 30a being inserted to blood vessel 68 to deliver blood to the body also to treat beta thalassemia via transfusion. Beta thalassemia is a blood disorder that reduces the production of hemoglobin.

In light of the foregoing, it should be understood that an indwelling access port 20, such as indwelling access port 20a, disclosed herein may also be used with the catheter 30a for a transfusion to treat any disease treatable thereby.

The foregoing description of several methods and embodiments has been presented for purposes of illustration. It is not intended to be exhaustive or to limit the claims to the precise steps and/or forms disclosed, and obviously many modifications and variations are possible in light of the above teaching. It is intended that the scope of the invention be defined by the claims appended hereto.

What is claimed is:

1. A medical system, comprising:
   an implantable access port configured to be implanted into a subject, the access port including an implantable access port body and at least one implantable access port needle;
   wherein the access port body is compressible to a compressed position and expandable to an expanded position;
   wherein the at least one implantable access port needle comprises a first needle and a second needle;
   wherein the first needle comprises a first needle shaft with a first needle lumen and the second needle comprises a second needle shaft with a second needle lumen;
   wherein the first needle and the second needle are concealed inside the access port body when the access port body is in the expanded position and are exposed outside the access port body when the access port body is in the compressed position;
   wherein the first needle and the second needle are arranged within the access port body to penetrate outwardly through skin of the subject from within the subject when the access port is implanted in the subject;
   a transfer device configured to transfer fluid to and fluid from the subject through the access port when coupled with the first needle and the second needle, respectively; and
   wherein the transfer device includes a first fluid flow passage configured to couple with the first needle lumen of the first needle to transfer the fluid to the subject through the access port and a second fluid flow passage configured to couple with the second needle lumen of the second needle to transfer the fluid from the subject through the access port;

wherein the transfer device comprises a tubular housing which is sealable against the skin of the subject prior to the first needle and the second needle penetrating outwardly through the skin of the subject, and into which the first needle and the second needle are disposable subsequent to the first needle and the second needle penetrating outwardly through the skin of the subject; and wherein the tubular housing is operable to compress the access port body to the compressed position when the access port is implanted in the subject.

2. The medical system of claim 1, wherein:
the transfer device forms a closed treatment system with the access port, wherein the closed treatment system inhibits transfer of environmental contaminants into the closed treatment system and escape of a hazardous material outside the closed treatment system.

3. The medical system of claim 1, wherein:
the first needle includes a first needle tip which is removable from the first needle shaft;
the second needle includes a second needle tip which is removable from the second needle shaft; and
the transfer device includes a first needle tip holder configured to hold the first needle tip, and a second needle tip holder configured to hold the second needle tip.

4. The medical system of claim 3, wherein:
the first needle tip holder is configured to form an interference fit with the first needle tip and/or the second needle tip holder is configured to form an interference fit with the second needle tip.

5. The medical system of claim 3, wherein:
the first needle tip holder is configured to form a positive mechanical engagement with the first needle tip and/or the second needle tip holder is configured to form a positive mechanical engagement with the second needle tip.

6. The medical system of claim 1, wherein:
the first needle includes a first needle tip which is removable from the first needle shaft;
the second needle includes a second needle tip which is removable from the second needle shaft; and
the transfer device is configured to remove the first needle tip from the first needle shaft and configured to remove the second needle tip from the second needle shaft.

7. The medical system of claim 6, wherein:
the transfer device is configured to remove the first needle tip by rotating the first needle tip and/or configured to remove the second needle tip by rotating the second needle tip.

8. The medical system of claim 6, wherein:
the transfer device is configured to remove the first needle tip by applying a pulling force to the first needle tip and/or configured to remove the second needle tip by applying a pulling force to the second needle tip.

9. The medical system of claim 1, wherein:
the first needle includes a first needle tip which is connectable on the first needle shaft;
the second needle includes a second needle tip which is connectable on the second needle shaft; and
the transfer device is configured to connect the first needle tip on the first needle shaft and configured to connect the second needle tip on the second needle shaft.

10. The medical system of claim 9, wherein:
the transfer device is configured to connect the first needle tip by rotating the first needle tip and/or configured to connect the second needle tip by rotating the second needle tip.

11. The medical system of claim 9, wherein:
the transfer device is configured to connect the first needle tip by applying a pushing force to the first needle tip and/or configured to connect the second needle tip by applying a pushing force to the second needle tip.

12. The medical system of claim 1, wherein:
the first needle includes a first needle first tip which is removable from the first needle shaft and the second needle included a second needle first tip which is removable from the second needle shaft;
the transfer device is configured to remove the first needle first tip from the first needle shaft and configured to remove the second needle first tip from the second needle shaft; and
the transfer device is configured to connect a first needle second tip on the first needle shaft and configured to connect a second needle second tip on the second needle shaft.

13. The medical system of claim 1, wherein:
the transfer device is configured to form a fluid-tight seal against the first needle and configured to form a fluid-tight seal against the second needle.

14. The medical system of claim 1, wherein:
the first fluid flow passage comprises a fluid infusion passage and the second fluid flow passage comprises a fluid extraction passage.

15. The medical system of claim 1, wherein:
the first fluid flow passage is configured to receive the first needle therein when the first fluid flow passage is in fluid communication with the first needle lumen and/or the second fluid flow passage is configured to receive the second needle therein when the second fluid flow passage is in fluid communication with the second needle lumen.

16. The medical system of claim 1, wherein:
the transfer device includes a fluid infusion port, and a fluid extraction port.

17. The medical system of claim 16, wherein:
the first fluid flow passage is in fluid communication with the fluid infusion port; the second fluid flow passage is in fluid communication with the fluid extraction port.

18. The medical system of claim 1, wherein:
the first needle shaft is configured to fit within the first fluid flow passage when the first fluid flow passage is in fluid communication with the first needle lumen and/or the second needle shaft is configured to fit within the second fluid flow passage when the second fluid flow passage is in fluid communication with the second needle lumen.

19. The medical system of claim 1, wherein:
the first needle includes a self-closing seal which seals the first needle lumen against fluid flow through the first needle lumen;
the second needle includes a self-closing seal which seals the second needle lumen against fluid flow through the second needle lumen.

20. The medical system of claim 19, wherein:
the transfer device is configured to extend through the first needle self-closing seal when the first fluid flow passage is in fluid communication with the first needle lumen and/or configured to extend through the second needle self-closing seal when the second fluid flow passage is in fluid communication with the second needle lumen.

\* \* \* \* \*